(12) United States Patent
Clarke et al.

(10) Patent No.: US 12,152,276 B2
(45) Date of Patent: Nov. 26, 2024

(54) COUPLING METHOD

(71) Applicant: Oxford Nanopore Technologies PLC, Oxford (GB)

(72) Inventors: James Anthony Clarke, Oxford (GB); James White, Oxford (GB); John Milton, Oxford (GB); Clive Gavin Brown, Cambridge (GB)

(73) Assignee: Oxford Nanopore Technologies PLC, Oxford (GB)

( * ) Notice: Subject to any disclaimer, the term of this patent is extended or adjusted under 35 U.S.C. 154(b) by 962 days.

(21) Appl. No.: 17/094,571

(22) Filed: Nov. 10, 2020

(65) Prior Publication Data

US 2021/0180124 A1 Jun. 17, 2021

Related U.S. Application Data

(63) Continuation of application No. 17/064,633, filed on Oct. 7, 2020, now Pat. No. 11,959,135, which is a continuation of application No. 16/428,845, filed on May 31, 2019, now Pat. No. 11,136,623, which is a continuation of application No. 16/243,118, filed on Jan. 9, 2019, now Pat. No. 11,041,194, which is a continuation of application No. 14/122,573, filed as application No. PCT/GB2012/051191 on May 25, 2012, now Pat. No. 10,246,741.

(60) Provisional application No. 61/599,246, filed on Feb. 15, 2012, provisional application No. 61/490,860, filed on May 27, 2011.

(51) Int. Cl.
| | |
|---|---|
| *C12Q 1/6869* | (2018.01) |
| *B82Y 15/00* | (2011.01) |
| *G01N 27/447* | (2006.01) |
| *G01N 33/487* | (2006.01) |

(52) U.S. Cl.
CPC ............ *C12Q 1/6869* (2013.01); *B82Y 15/00* (2013.01); *G01N 27/44743* (2013.01); *G01N 33/48721* (2013.01)

(58) Field of Classification Search
None
See application file for complete search history.

(56) References Cited

U.S. PATENT DOCUMENTS

| | | | |
|---|---|---|---|
| 5,576,204 A | 11/1996 | Blanco et al. | |
| 5,712,126 A | 1/1998 | Weissman et al. | |
| (Continued) | | | |

FOREIGN PATENT DOCUMENTS

| | | |
|---|---|---|
| AU | 2006/336262 A1 | 7/2007 |
| CN | 101356288 A | 1/2009 |
| (Continued) | | |

OTHER PUBLICATIONS

Chandler, Emily L. et al., "Membrane Surface Dynamics of DNA-Threaded Nanopores Revealed by Simultaneous Single-Molecule Optical and Ensemble Electrical Recording," Langmuir, vol. 20:898-905 (2004). (Year: 2004).*

(Continued)

*Primary Examiner* — Matthew D Krcha
(74) *Attorney, Agent, or Firm* — Wolf, Greenfield & Sacks, P.C.

(57) ABSTRACT

The invention relates to a new method of determining the presence, absence or characteristics of an analyte. The analyte is coupled to a membrane. The invention also relates to nucleic acid sequencing.

17 Claims, 25 Drawing Sheets

Specification includes a Sequence Listing.

(56) References Cited

U.S. PATENT DOCUMENTS

| | | |
|---|---|---|
| 5,840,083 A | 11/1998 | Braach-Maksvytis |
| 6,417,009 B1 | 7/2002 | Raguse et al. |
| 6,723,814 B2 | 4/2004 | Meier et al. |
| 8,828,208 B2 | 9/2014 | Canas et al. |
| 9,057,102 B2 | 6/2015 | Turner et al. |
| 9,222,082 B2 | 12/2015 | Jayasinghe et al. |
| 9,447,152 B2 | 9/2016 | Clarke et al. |
| 9,546,400 B2 | 1/2017 | Turner et al. |
| 9,556,480 B2 | 1/2017 | Turner et al. |
| 9,678,056 B2 | 6/2017 | Turner et al. |
| 9,738,929 B2 | 8/2017 | Turner et al. |
| 10,246,741 B2 | 4/2019 | Clarke et al. |
| 10,337,060 B2 | 7/2019 | Crawford et al. |
| 10,760,114 B2 | 9/2020 | Brown et al. |
| 10,774,378 B2 | 9/2020 | Clarke et al. |
| 11,041,194 B2 | 6/2021 | Clarke et al. |
| 11,136,623 B2 | 10/2021 | Clarke et al. |
| 11,236,385 B2 | 2/2022 | Crawford et al. |
| 11,613,771 B2 | 3/2023 | Brown et al. |
| 11,649,490 B2 | 5/2023 | Clarke et al. |
| 11,946,102 B2 | 4/2024 | Clarke et al. |
| 11,959,135 B2 | 4/2024 | Clarke et al. |
| 2002/0192769 A1 | 12/2002 | Park et al. |
| 2009/0269277 A1 | 10/2009 | Chang et al. |
| 2010/0331194 A1 | 12/2010 | Turner et al. |
| 2011/0108423 A1 | 5/2011 | Van Der Zaag et al. |
| 2011/0229877 A1 | 9/2011 | Jayasinghe et al. |
| 2012/0100530 A1 | 4/2012 | Moysey et al. |
| 2013/0146456 A1 | 6/2013 | Gundlach et al. |
| 2013/0296194 A1 | 11/2013 | Jacobson et al. |
| 2014/0134618 A1 | 5/2014 | Kokoris et al. |
| 2014/0186823 A1 | 7/2014 | Clarke et al. |
| 2014/0235462 A1 | 8/2014 | Kosteroglou et al. |
| 2014/0262784 A1 | 9/2014 | Clarke et al. |
| 2017/0022546 A1 | 1/2017 | Bashir et al. |
| 2017/0022557 A1 | 1/2017 | Clarke et al. |
| 2017/0204457 A1 | 7/2017 | Crawford et al. |
| 2017/0253910 A1 | 9/2017 | Brown et al. |
| 2019/0127682 A1 | 5/2019 | Aksimentiev et al. |
| 2019/0241949 A1 | 8/2019 | Clarke et al. |
| 2019/0382834 A1 | 12/2019 | Clarke et al. |
| 2020/0102608 A1 | 4/2020 | Crawford et al. |
| 2021/0087621 A1 | 3/2021 | Clarke et al. |
| 2021/0087623 A1 | 3/2021 | Clarke et al. |
| 2021/0095337 A1 | 4/2021 | Clarke et al. |
| 2021/0147904 A1 | 5/2021 | Brown et al. |
| 2023/0041418 A1 | 2/2023 | Brown et al. |
| 2023/0357821 A1 | 11/2023 | Brown et al. |
| 2023/0374583 A1 | 11/2023 | Clarke et al. |
| 2024/0124915 A9 | 4/2024 | Brown et al. |
| 2024/0158848 A1 | 5/2024 | Clarke et al. |

FOREIGN PATENT DOCUMENTS

| | | |
|---|---|---|
| CN | 102317310 A | 1/2012 |
| CN | 103695530 A | 4/2014 |
| CN | 103827320 A | 5/2014 |
| CN | 105723222 A | 6/2016 |
| EP | 2682460 A1 | 1/2014 |
| JP | 2009-519705 A1 | 5/2009 |
| JP | 2012-516146 A | 7/2012 |
| JP | 2014-519823 A | 8/2014 |
| WO | WO 2000/028312 A1 | 5/2000 |
| WO | WO 2000/078668 A1 | 12/2000 |
| WO | WO 2000/079257 A1 | 12/2000 |
| WO | WO 2001/032146 A2 | 5/2001 |
| WO | WO 2005/124888 A1 | 12/2005 |
| WO | WO 2006/100484 A2 | 9/2006 |
| WO | WO 2007/048459 A1 | 5/2007 |
| WO | WO 2007/057668 A1 | 5/2007 |
| WO | WO 2008/092760 A1 | 8/2008 |
| WO | WO 2008/102120 A1 | 8/2008 |
| WO | WO 2008/102121 A1 | 8/2008 |
| WO | WO 2008/124107 A1 | 10/2008 |
| WO | WO 2009/020682 A2 | 2/2009 |
| WO | WO 2009/035647 A1 | 3/2009 |
| WO | WO 2009/077734 A2 | 6/2009 |
| WO | WO 2009/132124 A2 | 10/2009 |
| WO | WO 2009/151788 A2 | 12/2009 |
| WO | WO 2010/004265 A1 | 1/2010 |
| WO | WO 2010/004273 A1 | 1/2010 |
| WO | WO 2010/034018 A2 | 3/2010 |
| WO | WO 2010/055307 A1 | 5/2010 |
| WO | WO 2010/086602 A1 | 8/2010 |
| WO | WO 2010/086603 A1 | 8/2010 |
| WO | WO 2010/086620 A1 | 8/2010 |
| WO | WO 2010/086622 A2 | 8/2010 |
| WO | WO 2010/122293 A1 | 10/2010 |
| WO | WO 2011/067559 A1 | 6/2011 |
| WO | WO 2012/005857 A1 | 1/2012 |
| WO | WO 2012/033524 A2 | 3/2012 |
| WO | WO 2012/107778 A2 | 8/2012 |
| WO | WO 2012/164270 A1 | 12/2012 |
| WO | WO 2013/014451 A1 | 1/2013 |
| WO | WO 2013/041878 A1 | 3/2013 |
| WO | WO 2013/057495 A2 | 4/2013 |
| WO | WO 2013/083983 A1 | 6/2013 |
| WO | WO 2013/098561 A1 | 7/2013 |
| WO | WO 2013/098562 A2 | 7/2013 |
| WO | WO 2013/119784 A1 | 8/2013 |
| WO | WO 2013/153359 A1 | 10/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/064443 A2 | 5/2014 |
| WO | WO 2014/064444 A1 | 5/2014 |
| WO | WO 2014/135838 A1 | 9/2014 |
| WO | WO 2015/022544 A1 | 2/2015 |
| WO | WO 2015/055981 A2 | 4/2015 |
| WO | WO 2015/061509 A1 | 4/2015 |
| WO | WO 2015/110777 A1 | 7/2015 |
| WO | WO 2015/124935 A1 | 8/2015 |
| WO | WO 2015/150786 A1 | 10/2015 |
| WO | WO 2015/150787 A1 | 10/2015 |
| WO | WO 2016/034591 A2 | 3/2016 |
| WO | WO 2016/055777 A2 | 4/2016 |
| WO | WO 2017/203268 A1 | 11/2017 |
| WO | WO 2019/150134 A1 | 8/2019 |

OTHER PUBLICATIONS

International Search Report and Written Opinion for Application No. PCT/GB2012/051191, mailed Sep. 10, 2012.

International Preliminary Report on Patentability for Application No. PCT/GB2012/051191, mailed Dec. 12, 2013.

[No Author Listed] Lambda Exonuclease product. 2017. Last accessed at https://www.neb.com/products/m0262-lambda-exonuclease on Feb. 8, 2017.

Albrecht, Nanobiotechnology: A new look for nanopore sensing. Nat Nanotechnol. Apr. 2011;6(4):195-6. doi: 10.1038/nnano.2011.52.

Ali et al., Sequence-specific recognition of DNA oligomer using peptide nucleic acid (PNA)—modified synthetic ion channels: PNA/DNA hybridization in nanoconfined environment. ACS Nano. Dec. 28, 2010;4(12):7267-74. doi: 10.1021/nn102119q. Epub Nov. 17, 2010.

Andersson et al., Detection of single ion channel activity on a chip using tethered bilayer membranes. Langmuir. Mar. 13, 2007;23(6):2924-7. Epub Feb. 8, 2007.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Avrantinis et al., Dissecting the streptavidin-biotin interaction by phage-displayed shotgun scanning. Chembiochem. Dec. 2, 2002;3(12):1229-34. doi: 10.1002/1439-7633(20021202)3:12<1229::AID-CBIC1229>3.0.CO;2-X.

Case 1:17-cv-00275-LPS Document 18. Notice of subsequent events relating to Oxford's motion to dismiss (D.I. 9). Oct. 18, 2017.

(56) References Cited

OTHER PUBLICATIONS

Case 1:17-cv-00275-LPS Document 19. Oxford Nanopore Technologies, Inc.'s response to Pacific Biosciences of California, Inc.'s notice of subsequent events. Oct. 24, 2017.
Case 1:17-cv-00275-RGA Document 10. Oxford's opening brief in support of its motion to dismiss PacBio's complaint for patent infringement. May 8, 2017.
Case 1:17-cv-00275-RGA Document 14. PacBio's response to Oxford's motion to dismiss. Jun. 5, 2017.
Case 1:17-cv-00275-RGA Document 16. Oxford's reply brief in support of its motion to dismiss PacBio's complaint for patent infringement. Jun. 26, 2017.
Case 1:17-cv-01353-LPS Document 13. First Amended Complaint for Patent Infringement. Nov. 30, 2017.
Case 1:17-cv-01353-LPS Document 15. Plaintiff's response to Oxford Nanopore Techologies, Inc.'s Motion to Dismiss and Request for Scheduling Conference. Nov. 30, 2017.
Case 1:17-cv-01353-RGA Document 10. Oxford's opening brief in support of its motion to partially dismiss Pacbio's complaint for patent infringement. Nov. 16, 2017.
Chandler et al., Membrane surface dynamics of DNA-threaded nanopores revealed by simultaneous single-molecule optical and ensemble electrical recording. Langmuir. Feb. 3, 2004;20(3):898-905.
Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.
Cockroft et al., A single-molecule nanopore device detects DNA polymerase activity with single-nucleotide resolution. J Am Chem Soc. Jan. 23, 2008;130(3):818-20. doi: 10.1021/ja077082c. Epub Jan. 1, 2008.
Dekker, Solid-state nanopores. Nat Nanotechnol. Apr. 2007;2(4):209-15. doi:10.1038/nnano.2007.27. Epub Mar. 4, 2007.
Feng et al., Nanopore-based fourth-generation DNA sequencing technology. Genomics Proteomics Bioinformatics. Feb. 2015;13(1):4-16. doi: 10.1016/j.gpb.2015.01.009. Epub Mar. 2, 2015. Review. Erratum in: Genomics Proteomics Bioinformatics. Dec. 2015;13(6):383. Genomics Proteomics Bioinformatics. Jun. 2015;13(3):200-201.
Gu et al., Interaction of the noncovalent molecular adapter, beta-cyclodextrin, with the staphylococcal alpha-hemolysin pore. Biophys J. Oct. 2000;79(4):1967-75.
Heredia et al., In vitro double transposition for DNA identification. Anal Biochem. Apr. 1, 2010;399(1):78-83. doi:10.1016/j.ab.2009.11.030. Epub Nov. 26, 2009.
Holden et al., Direct introduction of single protein channels and pores into lipid bilayers. J Am Chem Soc. May 11, 2005;127(18):6502-3.
Howorka et al., Nanopore analytics: sensing of single molecules. Chem Soc Rev. Aug. 2009;38(8):2360-84. doi: 10.1039/b813796j. Epub Jun. 15, 2009.
Howorka et al., Sequence-specific detection of individual DNA strands using engineered nanopores. Nat Biotechnol. Jul. 2001;19(7):636-9.
Ivanov et al., DNA tunneling detector embedded in a nanopore. Nano Lett. Jan. 12, 2011;11(1):279-85. doi: 10.1021/nl103873a. Epub Dec. 6, 2010.
Kasianowicz et al., Characterization of individual polynucleotide molecules using a membrane channel. Proc Natl Acad Sci U S A. Nov. 26, 1996;93(24):13770-3.
Keyser, Controlling molecular transport through nanopores. J R Soc Interface. Oct. 7, 2011;8(63):1369-78. doi: 10.1098/rsif.2011.0222.
Langecker et al., Synthetic lipid membrane channels formed by designed DNA nanostructures. Science. Nov. 16, 2012;338(6109):932-6. doi: 10.1126/science.1225624.
Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010.

Nikolov et al., Behavior of giant vesicles with anchored DNA molecules. Biophys J. Jun. 15, 2007;92(12):4356-68. Epub Mar. 23, 2007.
Ohvo et al., Cyclodextrin-mediated removal of sterols from monolayers:effects of sterol structure and phospholipids on desorption rate. Biochemistry. Jun. 18, 1996;35(24):8018-24.
Peng et al., Reverse DNA translocation through a solid-state nanopore by magnetic tweezers. Nanotechnology. May 6, 2009;20(18):185101. doi: 10.1088/0957-4484/20/18/185101. Epub Apr. 14, 2009.
Pfeiffer et al., Bivalent cholesterol-based coupling of oligonucleotides to lipid membrane assemblies. J Am Chem Soc. Aug. 25, 2004;126(33):10224-5.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
United States District Court for the District of Delaware Order. *Pacific Biosciences of California, Inc. v. Oxford Nanopore Technolgoies, Inc.* Civil Action No. 17-275-RGA. Nov. 9, 2017.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Wanunu et al., DNA translocation governed by interactions with solid-state nanopores. Biophys J. Nov. 15, 2008;95(10):4716-25. doi: 10.1529/biophysj.108.140475. Epub Aug. 15, 2008.
Wilson et al., Electronic control of DNA polymerase binding and unbinding to single DNA molecules. ACS Nano. Apr. 28, 2009;3(4):995-1003. doi: 10.1021/nn9000897.
Yoshina-Ishii et al., Arrays of mobile tethered vesicles on supported lipid bilayers. J Am Chem Soc. Apr. 2, 2003;125(13):3696-7.
Behzadi et al., A triblock terpolymer vs. blends of diblock copolymers for nanocapsules addressed by three independent stimuli. Polymer Chemistry. 2016;7(20):3434-43.
Booth et al., 3D-printed synthetic tissues. The Biochemist. Aug. 1, 2016;38(4):16-9. Author Manuscript, 11 pages.
Borgese, Getting membrane proteins on and off the shuttle bus between the endoplasmic reticulum and the Golgi complex. J Cell Sci. Apr. 15, 2016;129(8):1537-45. doi: 10.1242/jcs.183335. Epub Mar. 30, 2016.
Boulant et al., Dynamics of virus-receptor interactions in virus binding, signaling, and endocytosis. Viruses. Jun. 2, 2015;7(6):2794-815. doi: 10.3390/v7062747.
Chan et al., Adsorption and surface diffusion of DNA oligonucleotides at liquid/solid interfaces. Langmuir. Jan. 22, 1997;13(2):320-9.
Christensen et al., Effect of charge, topology and orientation of the electric field on the interaction of peptides with the $\alpha$-hemolysin pore. J Pept Sci. Nov. 2011;17(11):726-34. doi: 10.1002/psc.1393. Epub Jul. 18, 2011.
Gunnarsson et al., Affinity Capturing and Surface Enrichment of a Membrane Protein Embedded in a Continuous Supported Lipid Bilayer. ChemistryOpen. Aug. 22, 2016;5(5):445-449. doi: 10.1002/open.201600070. Supporting Information, 14 pages.
Heron et al., Simultaneous measurement of ionic current and fluorescence from single protein pores. J Am Chem Soc. Feb. 11, 2009;131(5):1652-3. doi: 10.1021/ja808128s.
Holyst et al., Reduction of dimensionality in a diffusion search process and kinetics of gene expression. Physica A: Statistical Mechanics and its Applications. Mar. 1, 2000;277(1-2):71-82.
Howorka et al., A protein pore with a single polymer chain tethered within the lumen. Journal of the American Chemical Society. Mar. 22, 2000;122(11):2411-6.
Laszlo et al., Decoding long nanopore sequencing reads of natural DNA. Nat Biotechnol. Aug. 2014;32(8):829-33. doi: 10.1038/nbt.2950. Epub Jun. 25, 2014.
Liu et al., Adding new chemistries to the genetic code. Annu Rev Biochem. 2010;79:413-44. doi: 10.1146/annurev.biochem.052308.105824.
Marx, Nanopores: a sequencer in your backpack. Nat Methods. Nov. 2015;12(11):1015-8. doi: 10.1038/nmeth.3625.

(56) References Cited

OTHER PUBLICATIONS

Mathe et al., Nanopore unzipping of individual DNA hairpin molecules. Biophys J. Nov. 2004;87(5):3205-12. doi: 10.1529/biophysj.104.047274. Epub Sep. 3, 2004.

Mayle et al., The intracellular trafficking pathway of transferrin. Biochim Biophys Acta. Mar. 2012;1820(3):264-81. doi: 10.1016/j.bbagen.2011.09.009. Epub Sep. 22, 2011. Author Manuscript, 44 pages.

Niedringhaus et al., Landscape of next-generation sequencing technologies. Anal Chem. Jun. 15, 2011;83(12):4327-41. doi: 10.1021/ac2010857. Epub May 25, 2011.

Pennisi, Genome sequencing. Search for pore-fection. Science. May 4, 2012;336(6081):534-7. doi: 10.1126/science.336.6081.534.

Rhee et al., Nanopore sequencing technology: nanopore preparations. Trends Biotechnol. Apr. 2007;25(4):174-81. doi: 10.1016/j.tibtech.2007.02.008. Epub Feb. 22, 2007.

Rhee et al., Nanopore sequencing technology: research trends and applications. Trends Biotechnol. Dec. 2006;24(12):580-6. doi: 10.1016/j.tibtech.2006.10.005. Epub Oct. 19, 2006.

Rusk, Nanopores read long genomic DNA. Nat Methods. Sep. 2014;11(9):887. doi: 10.1038/nmeth.3085.

Ryu et al., Continuity of Monolayer-Bilayer Junctions for Localization of Lipid Raft Microdomains in Model Membranes. Sci Rep. May 27, 2016;6:26823. doi: 10.1038/srep26823.

Saslowsky et al., Placental alkaline phosphatase is efficiently targeted to rafts in supported lipid bilayers. J Biol Chem. Jul. 26, 2002;277(30):26966-70. doi: 10.1074/jbc.M204669200. Epub May 14, 2002.

Shui et al., Nanopore-based proteolytic reactor for sensitive and comprehensive proteomic analyses. Anal Chem. Jul. 15, 2006;78(14):4811-9. doi: 10.1021/ac060116z.

Soni et al., Progress toward ultrafast DNA sequencing using solid-state nanopores. Clin Chem. Nov. 2007;53(11):1996-2001. doi: 10.1373/clinchem.2007.091231. Epub Sep. 21, 2007.

Tunca, Orthogonal multiple click reactions in synthetic polymer chemistry. Journal of Polymer Science Part A: Polymer Chemistry. Nov. 15, 2014;52(22):3147-65.

Watanabe et al., High-throughput formation of lipid bilayer membrane arrays with an asymmetric lipid composition. Sci Rep. Nov. 17, 2014;4:7076. doi: 10.1038/srep07076.

Yusko et al., Controlling protein translocation through nanopores with bio-inspired fluid walls. Nat Nanotechnol. 2011;6:253-60.

U.S. Appl. No. 17/064,628, filed Oct. 7, 2020, Clarke et al.
U.S. Appl. No. 17/064,633, filed Oct. 7. 2020, Clarke et al.
U.S. Appl. No. 16/993,601, filed Aug. 14, 2020, Clarke et al.
U.S. Appl. No. 16/902,306, filed Jun. 6, 2020, Brown et al.
PCT/GB2012/051191, Sep. 10. 2012, *International Search Report and Written Opinion.
PCT/GB2012/051191, Dec. 12, 2013, *International Preliminary Report on Patentability.

* cited by examiner

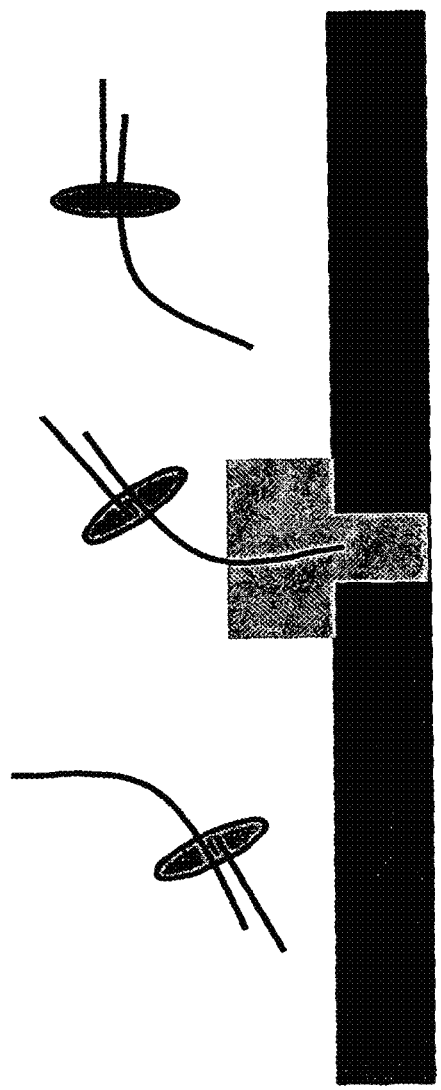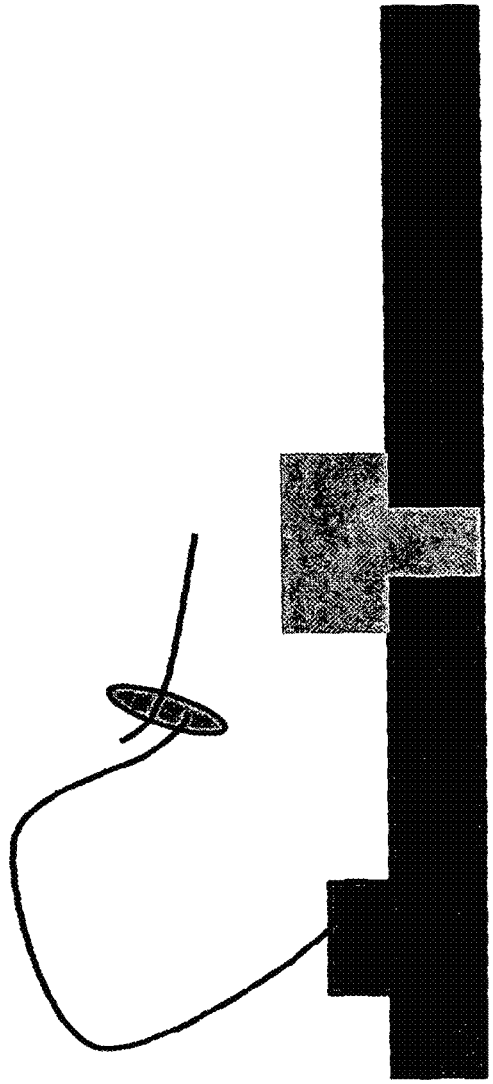

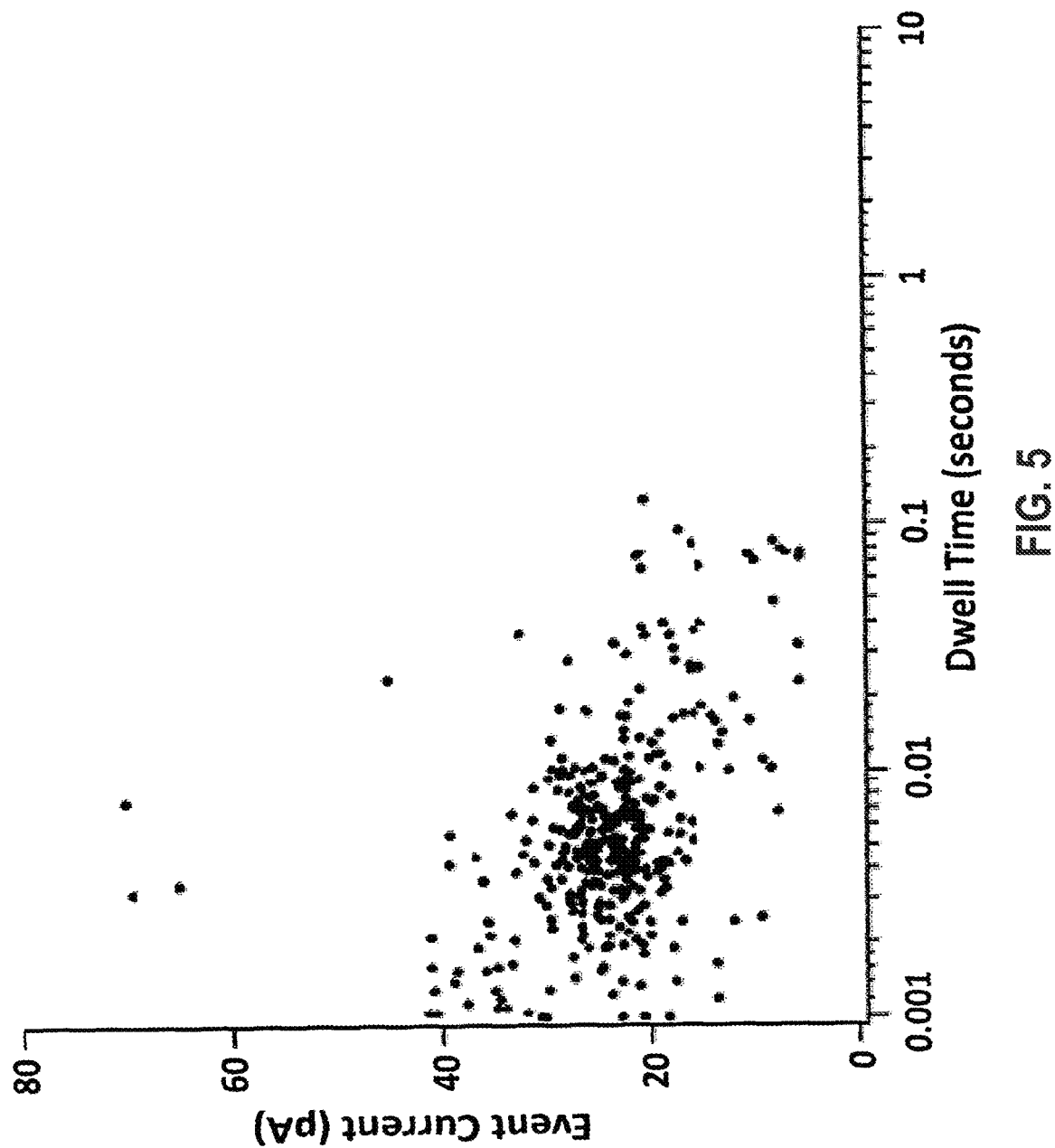

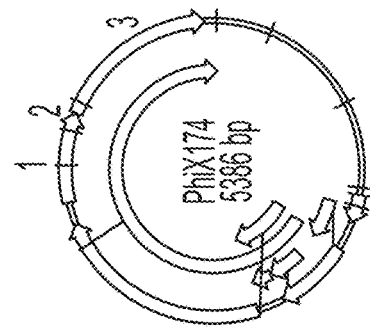
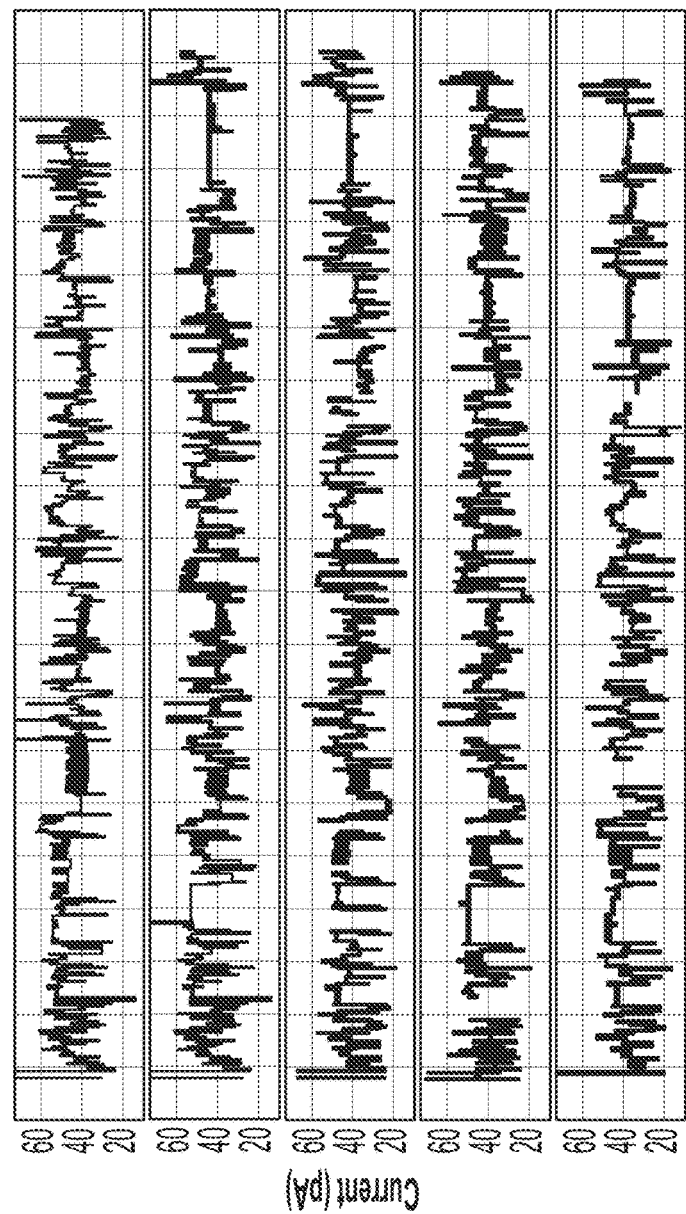
FIG. 15

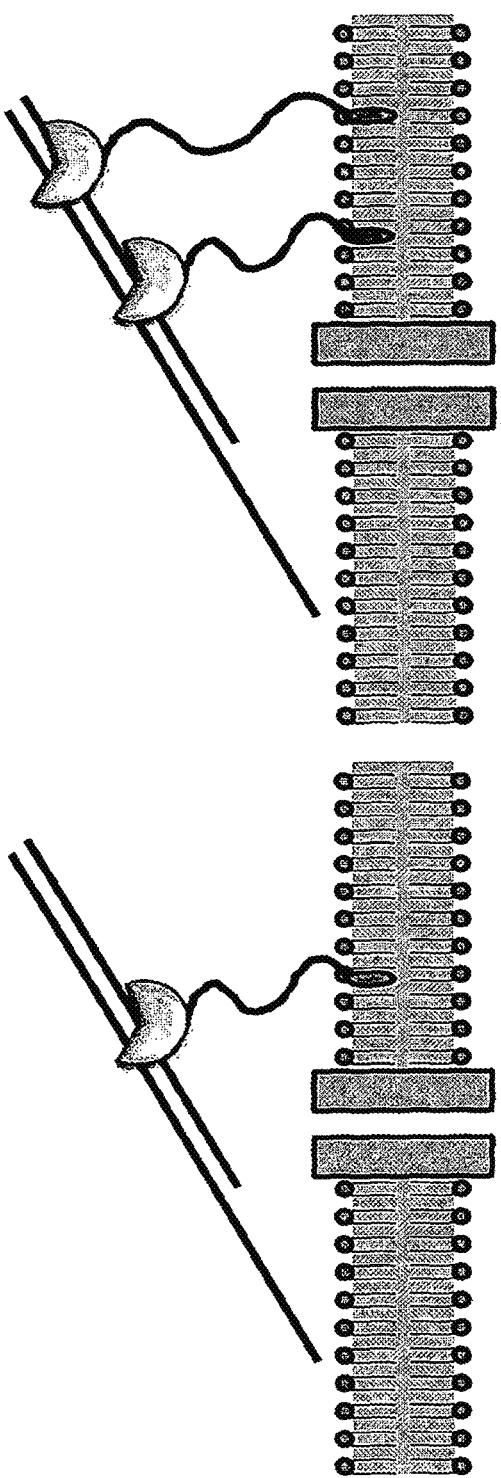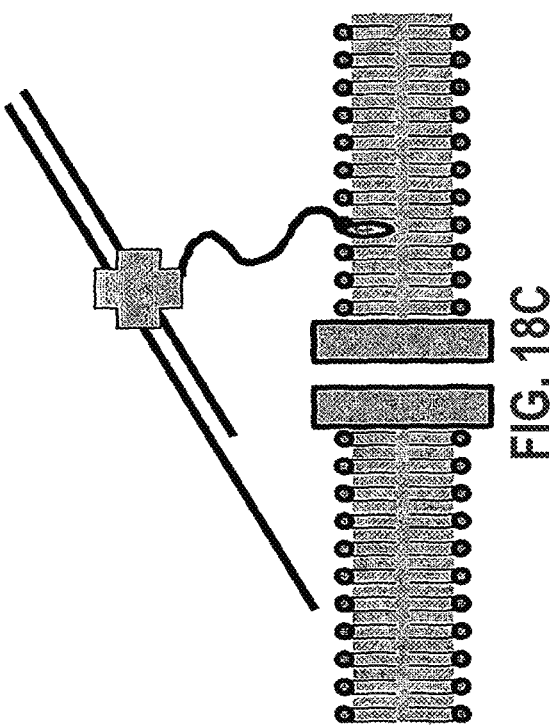

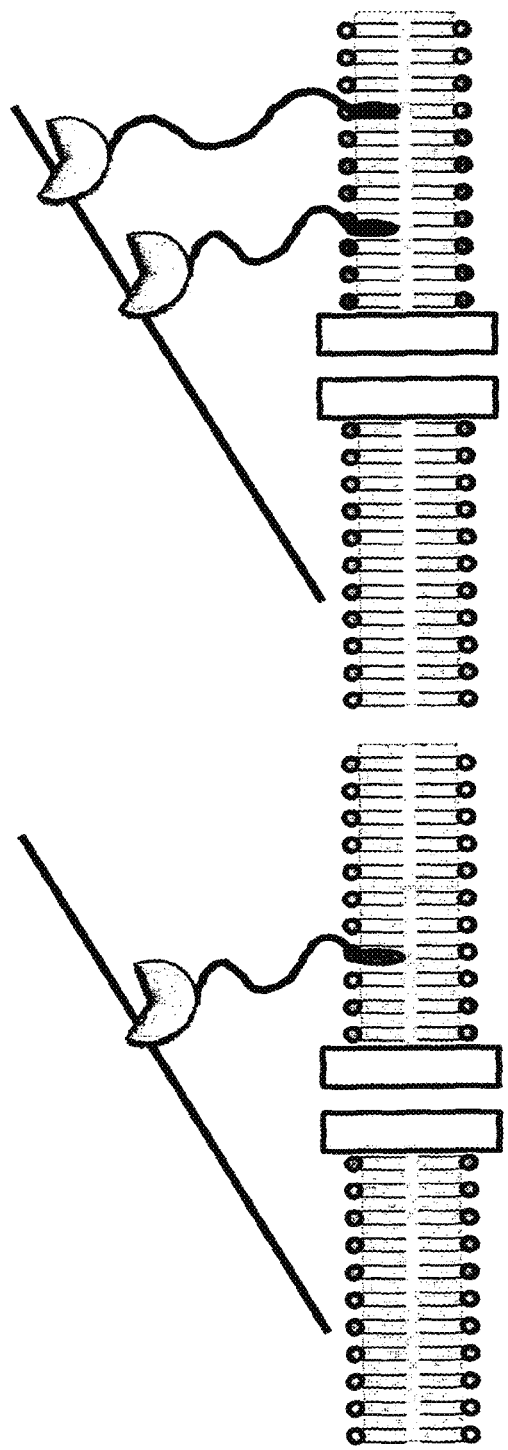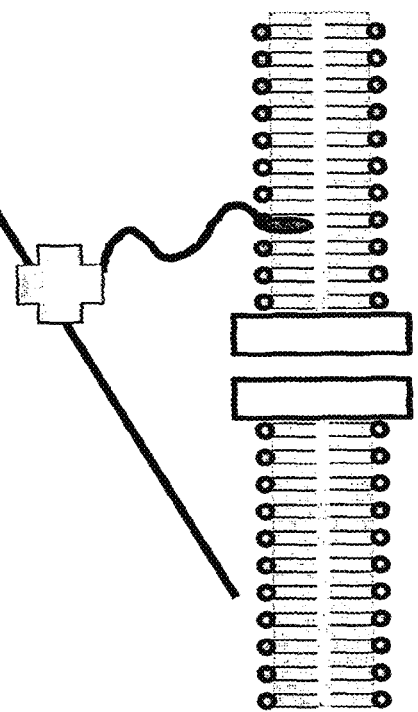
FIG. 19A
FIG. 19B
FIG. 19C

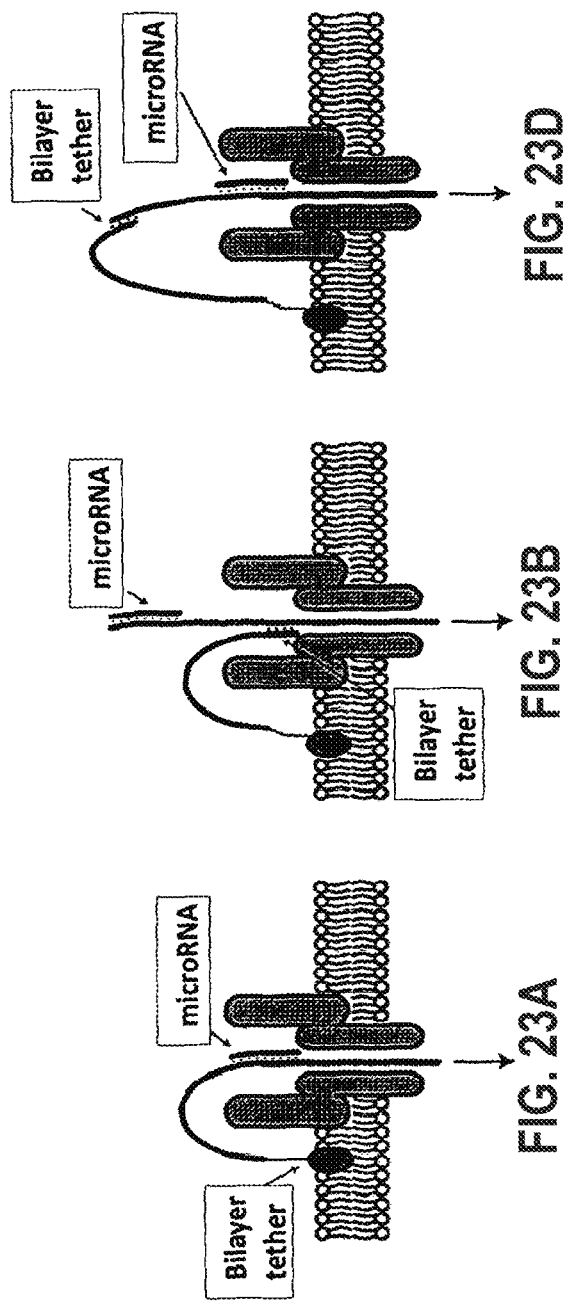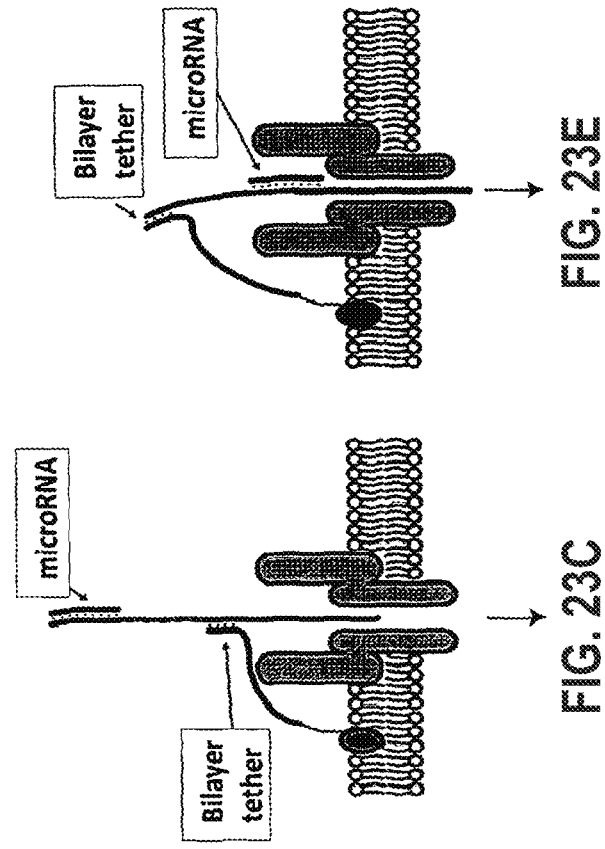

COUPLING METHOD

RELATED APPLICATIONS

This application is a continuation of U.S. application Ser. No. 17/064,633, filed Oct. 7, 2020, which is continuation of U.S. application Ser. No. 16/428,845, filed on May 31, 2019, which is a continuation of U.S. application Ser. No. 16/243,118, filed on Jan. 9, 2019, which is a continuation of U.S. application Ser. No. 14/122,573, filed Apr. 16, 2014, which is a national stage filing under U.S.C. § 371 of PCT International Application No. PCT/GB2012/051191, with an international filing date of May 25, 2012, which claims the benefit of the filing date under 35 U.S.C. § 119 of U.S. Provisional Application Ser. No. 61/599,246, filed Feb. 15, 2012, and claims the benefit of U.S. Application Ser. No. 61/490,860, filed May 27, 2011, the entire contents of each of which are incorporated herein by reference.

FIELD OF THE INVENTION

The invention relates to a new method of determining the presence, absence or characteristics of an analyte. The analyte is coupled to a membrane. The invention also relates to nucleic acid sequencing.

BACKGROUND OF THE INVENTION

There is currently a need for rapid and cheap nucleic acid (e.g. DNA or RNA) sequencing technologies across a wide range of applications. Existing technologies are slow and expensive mainly because they rely on amplification techniques to produce large volumes of nucleic acid and require a high quantity of specialist fluorescent chemicals for signal detection.

Nanopores have great potential as direct, electrical biosensors for polymers and a variety of small molecules. In particular, recent focus has been given to nanopores as a potential DNA sequencing technology. Two methods for DNA sequencing have been proposed; 'Exonuclease Sequencing', where bases are processively cleaved from the polynucleotide by an exonuclease and are then individually identified by the nanopore and also 'Strand Sequencing', where a single DNA strand is passed through the pore and nucleotides are directly identified. Strand Sequencing may involve the use of a DNA handling enzyme to control the movement of the polynucleotide through the nanopore.

When a potential is applied across a nanopore, there is a drop in the current flow when an analyte, such as a nucleotide, resides transiently in the barrel for a certain period of time. Nanopore detection of the analyte gives a current blockade of known signature and duration. The concentration of an analyte can then be determined by the number of blockade events per unit time to a single pore.

For nanopore applications, such as DNA Sequencing, efficient capture of analyte from solution is required. For instance, in order to give the DNA handling enzyme used in DNA Sequencing a sufficiently high duty cycle to obtain efficient sequencing, the number of interactions between enzyme and polynucleotide needs to be maximal, so that a new polynucleotide is bound as soon as the present one is finished. Therefore, in DNA Sequencing, it is preferred to have the polynucleotide at as high a concentration as is possible so that, as soon as an enzyme finishes processing one, the next is readily available to be bound. This becomes a particular problem as the concentration of polynucleotide, such as DNA, becomes limiting, e.g. DNA from cancer cell samples for epigenetics. The more dilute the sample then the longer between sequencing runs, up to the point where binding the first polynucleotide is so limiting that it is unfeasible.

The limits of nanopore detection have been estimated for various analytes. Capture of a 92-nucleotide synthetic piece of single strand DNA (ssDNA) by a protein nanopore (hemolysin) was determined to be at a frequency of 3.0±0.2 $s^{-1}$ $uM^{-1}$ (Maglia, Restrepo et al. 2008. *Proc Natl Acad Sci USA* 105(50): 19720-5). Capture could be increased ~10 fold by the addition of a ring of positive charges at the entrance to the hemolysin barrel (23.0±2 $s^{-1}$ $uM^{-1}$). To put this into context, 1 uM of 92 nucleotide ssDNA is equivalent to 31 ug of DNA required per single channel recording, assuming a cis chamber volume of 1 ml. The market leading genomic DNA purification kit from human blood (Qiagen's PAXgene Blood DNA Kit) currently gives expected yields of between 150-500 ug of genomic from 8.5 ml of human whole blood. Therefore, this disclosed increase in analyte detection is still well short of the step change required for ultra-sensitive detection and delivery.

SUMMARY OF THE INVENTION

The inventors have surprisingly demonstrated ultra low concentration analyte delivery by coupling the analyte to a membrane in which the relevant detector is present. This lowers by several orders of magnitude the amount of analyte required in order to be detected. The extent to which the amount of analyte needed is reduced could not have been predicted.

In particular, the inventors surprisingly report an increase in the capture of single stranded DNA by ~4 orders of magnitude over that previously reported. As both the detector and analyte are now on the same plane, then ~$10^3$ M $s^{-1}$ more interactions occur per second, as diffusion of both molecules is in two dimensions rather than three dimensions. This has dramatic implications on the sample preparation requirements that are of key concern for diagnostic devices such as next-generation sequencing systems.

In addition, coupling the analyte to a membrane has added advantages for various nanopore-enzyme sequencing applications. In Exonuclease Sequencing, when the DNA analyte is introduced the pore may become blocked permanently or temporarily, preventing the detection of individual nucleotides. When one end of the DNA analyte is localised away from the pore, for example by coupling or tethering to the membrane, surprisingly it was found that this temporary or permanent blocking is no longer observed. By occupying one end of the DNA by coupling it to the membrane it also acts to effectively increase the analyte concentration over the detector and so increase the sequencing systems duty cycle. This is discussed in more detail below.

Accordingly, the invention provides a method for determining the presence, absence or characteristics of an analyte, comprising (a) coupling the analyte to a membrane and (b) allowing the analyte to interact with a detector present in the membrane and thereby determining the presence, absence or characteristics of the analyte.

The invention also provides:
a method of sequencing an analyte which is a target polynucleotide, comprising:
  (a) coupling the target polynucleotide to a membrane;
  (b) allowing the target polynucleotide to interact with a detector present in the membrane, wherein the detector comprises a transmembrane pore and an exonuclease, such that the exonuclease digests an individual nucleotide from one end of the target polynucleotide;

(c) allowing the nucleotide to interact with the pore;

(d) measuring the current passing through the pore during the interaction and thereby determining the identity of the nucleotide; and (e) repeating steps (b) to (d) at the same end of the target polynucleotide and thereby determining the sequence of the target polynucleotide;

a method of sequencing an analyte which is a target polynucleotide, comprising:

(a) coupling the target polynucleotide to a membrane;

(b) allowing the target polynucleotide to interact with a detector present in the membrane, wherein the detector comprises a transmembrane pore, such that the target polynucleotide moves through the pore; and (c) measuring the current passing through the pore as the target polynucleotide moves with respect to the pore and thereby determining the sequence of the target polynucleotide;

a kit for sequencing an analyte which is a target polynucleotide comprising (a) a transmembrane pore, (b) a polynucleotide binding protein and (c) means to couple the target polynucleotide to a membrane; and an apparatus for sequencing an analyte which is a target polynucleotide, comprising (a) a membrane, (b) a plurality of transmembrane pores in the membrane. (c) a plurality of polynucleotide binding proteins and (d) a plurality of target polynucleotides coupled to the membrane.

DESCRIPTION OF THE FIGURES

FIG. 1A shows a nanopore with the direction of the current flow indicated by grey arrows. A predicted current trace is shown below. FIG. 1B shows a nanopore with an analyte translocating through the pore. The direction of analyte movement is indicated by arrow 1 and the direction of the current flow by the grey arrows. A predicted current trace is shown below showing how the current changes as the analyte translocates through the pore.

FIGS. 2A-2B show transient tethered ssDNA and how the current trace changes as the ssDNA translocates through the pore. FIGS. 2C-2D show stable tethered ssDNA and how the current trace changes as the ssDNA is captured by the pore.

FIGS. 4A-4B show the experimental setup for Example 2. Comparison between (1) a primer/template DNA analyte in solution (FIG. 4A) where the concentrations of material are in the high nanomolar range (400 nM DNA used and 800 nN enzyme used) and (2) a tethered system (FIG. 4B) where the amount of material is sub-nanomolar (1 nM DNA used and 5 nN enzyme used).

FIG. 5 shows KF binding times on top of the nanopore for non-tethered analyte (DNA) in the absence of KF (DNA concentration=400 nM).

FIG. 15 shows unzipping events from the 800 bp PhiX 174 amplified fragment. This 800 bp sequence corresponds to the sequence between points 1 and 3 in the plasmid map shown.

FIG. 17A shows tethering into a modified surface (tethering in a layer). FIG. 17B shows tethering to a modified surface (interaction with the surface). FIG. 17C shows tethering to a lipid monolayer on a modified surface. FIG. 17D shows tethering to a lipid bilayer on a modified surface.

FIGS. 18A-18C show methods for coupling double stranded polynucleotides to a lipid membrane. FIG. 18A shows a single tethered dsDNA binding protein interacting with dsDNA analyte. FIG. 18B shows multiple tethered dsDNA binding proteins interacting with a single dsDNA analyte. FIG. 18C shows a single tethered chemical group interacting with dsDNA analyte.

FIGS. 19A-19C show methods for coupling single stranded polynucleotide analytes to lipid membranes. FIG. 19A shows a single tethered ssDNA binding protein interacting with ssDNA. FIG. 19B shows multiple tethered ssDNA binding proteins interacting with a single ssDNA. FIG. 19C shows a single tethered chemical group interacting with ssDNA.

FIG. 20A) A DNA analyte (consisting of a ssDNA leader (grey region) attached to a dsDNA region) is coupled to the membrane using a tethered dsDNA binding protein, resulting in a concentration enhancement at the membrane surface. A polynucleotide binding protein capable of controlling polynucleotide movement is added to the cis compartment where it binds to the 4 bp overhang. FIG. 20B) Under an applied voltage, the DNA analyte is captured by the nanopore via the 5' leader section (grey region) on the DNA. FIG. 20C) Under the force of the applied field the DNA is pulled into the pore until the bound polynucleotide binding protein contacts the top of the pore and prevents further uncontrolled translocation. In this process the antisense strand is stripped from the DNA strand, therefore, resulting in the detachment of the dsDNA binding protein from the strand. FIG. 20D) In the presence of appropriate cofactors, the polynucleotide binding protein on top of the pore moves along the DNA and controls the translocation of the DNA through the pore. The movement of the polynucleotide binding protein, along the DNA in a 3' to 5' direction, pulls the threaded DNA out of the pore against the applied field back to the cis compartment. The last section of DNA to pass through the nanopore is the 5'-leader. The arrow indicates the direction of DNA movement.

FIG. 21A) A DNA analyte (consisting of a ssDNA leader (grey region) attached to a dsDNA region) is coupled to the membrane using a hybridised tether, resulting in a concentration enhancement at the membrane surface. A polynucleotide binding protein capable of controlling DNA movement is added to the cis compartment where it binds to the 4 bp overhang. FIG. 21B) Under an applied voltage, the DNA analyte is captured by the nanopore via the 5' leader section (grey region) on the DNA. FIG. 21C) Under the force of the applied field the DNA is pulled into the pore until the bound polynucleotide binding protein contacts the top of the pore and prevents further uncontrolled translocation. In this process the polynucleotide which is tethered to the membrane (dashed line) is stripped off to be sequenced (black strand with grey leader region). FIG. 21D) In the presence of appropriate cofactors, the polynucleotide binding protein on top of the pore moves along the DNA and controls the translocation of the DNA through the pore. The movement of the polynucleotide binding protein, along the DNA in a 3' to 5' direction, pulls the threaded DNA out of the pore against the applied field back to the cis compartment. The last section of DNA to pass through the nanopore is the 5'-leader. The arrow indicates the direction of DNA movement.

FIG. 22A) A DNA analyte (consisting of ssDNA (black line with the leader sequence shown in grey) hybridised to a ssDNA tether (dashed line)) is coupled to the membrane using a hybridised tether, resulting in a concentration enhancement at the membrane surface. A polynucleotide binding protein capable of controlling DNA movement is added to the cis compartment where it binds to the 4 bp overhang. FIG. 22B) Under an applied voltage, the DNA analyte is captured by the nanopore via the 5' leader section (grey region) on the DNA. FIG. 22C) Under the force of the applied field the DNA is pulled into the pore until the bound polynucleotide binding protein contacts the top of the pore and prevents further uncontrolled translocation. In this process the strand which is tethered to the membrane (dashed line) is stripped off the ssDNA strand to be sequenced (black strand with grey leader region). FIG. 22D) In the presence of appropriate cofactors, the polynucleotide binding protein on top of the pore moves along the DNA and controls the translocation of the DNA through the pore. The movement of the polynucleotide binding protein, along the DNA in a 3' to 5' direction, pulls the threaded DNA out of the pore against the applied field back to the cis compartment. The last section of DNA to pass through the nanopore is the 5'-leader. The arrow indicates the direction of DNA movement.

FIGS. 23A-23E show several methods of tethering a probe, which can be employed for the detection of microRNA, to a membrane. FIG. 23A) The probe can be permanently tethered to the membrane. In this instance the region of the probe that hybridises to the microRNA is in the middle of the probe. The barcoded region (dotted region) of the probe, which is used to identify the probe, is located at the opposite end of the strand to the tether. FIGS. 23B-23C) The probe can be transiently tethered to the membrane by internal hybridisation. In this example the region of the probe that hybridises to the microRNA is attached to one end of the strand. The barcoding region (dotted region), which is used to identify the probe, is located directly above the tether and below the microRNA hybridisation region. In FIG. 23C) the hybridisation region of the tether to the probe is inverted in its binding direction in comparison to FIG. 23B. FIGS. 23D-23E) The probe can be transiently tethered to the membrane by hybridisation to one end of the probe. In this example the region of the probe that hybridises to the microRNA is located in the middle of the strand. The barcoding region (dotted region), which is used to detect the presence or absence of the microRNA, is located below the microRNA hybridisation region at the opposite end of the probe to the tether. In FIG. 23E the hybridisation region of the tether to the probe is inverted in its binding direction in comparison to FIG. 23D.

DESCRIPTION OF THE SEQUENCE LISTING

Figure 1:
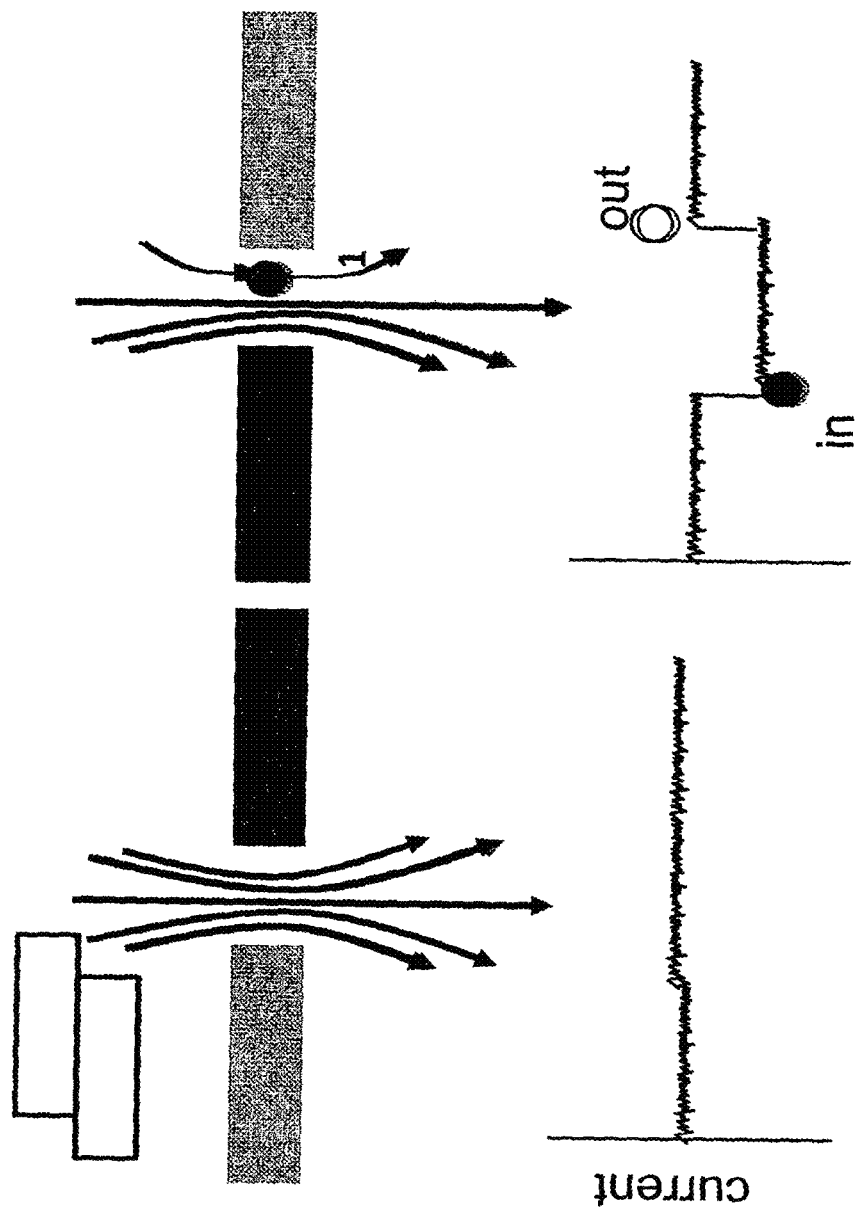
FIGS. 1A-1B show nanopore sensing of an analyte.

SEQ ID NO: 1 shows the codon optimised polynucleotide sequence encoding the NNN-RRK mutant MspA monomer.
SEQ ID NO: 2 (also referred to as "B1") shows the amino acid sequence of the mature form of the NNN-RRK mutant of the MspA monomer. The mutant lacks the signal sequence and includes the following mutations: D90N, D91N, D93N, D11812, D134R and E139K. These mutations allow DNA transition through the MspA pore.
SEQ ID NO: 3 shows the polynucleotide sequence encoding one subunit of α-hemolysin-M111R (α-HL-R).
SEQ ID NO: 4 shows the amino acid sequence of one subunit of α-HL-R.
SEQ ID NO: 5 shows the codon optimised polynucleotide sequence encoding the Phi29 DNA polymerase.
SEQ ID NO: 6 shows the amino acid sequence of the Phi29 DNA polymerase.
SEQ ID NO: 7 shows the codon optimised polynucleotide sequence derived from the sbcB gene from *E. coli*. It encodes the exonuclease I enzyme (EcoExo I) from *E. coli*.
SEQ ID NO: 8 shows the amino acid sequence of exonuclease I enzyme (EcoExo from *E. coli*.
SEQ ID NO: 9 shows the codon optimised polynucleotide sequence derived from the xthA gene from *E. coli*. It encodes the exonuclease III enzyme from *E. coli*.
SEQ ID NO: 10 shows the amino acid sequence of the exonuclease III enzyme from *E. coli*. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.
SEQ ID NO: 11 shows the codon optimised polynucleotide sequence derived from the recJ gene from *T. thermophilus*. It encodes the RecJ enzyme from *T. thermophilus* (TthRecJ-cd).
SEQ ID NO: 12 shows the amino acid sequence of the RecJ enzyme from *T. thermophilus* (TthRecJ-cd). This enzyme performs processive digestion of 5' monophosphate nucleosides from ssDNA in a 5'-3' direction. Enzyme initiation on a strand requires at least 4 nucleotides.
SEQ ID NO: 13 shows the codon optimised polynucleotide sequence derived from the bacteriophage lambda exo (redX) gene. It encodes the bacteriophage lambda exonuclease.
SEQ ID NO: 14 shows the amino acid sequence of the bacteriophage lambda exonuclease. The sequence is one of three identical subunits that assemble into a trimer. The enzyme performs highly processive digestion of nucleotides from one strand of dsDNA, in a 5'-3'direction (http://www.ncb.com/nebecomm/products/productM0262.asp). Enzyme initiation on a strand preferentially requires a 5' overhang of approximately 4 nucleotides with a 5' phosphate.
SEQ ID NOs: 15 to 17 show the amino acid sequences of the mature forms of the MspB, C and D mutants respectively. The mature forms lack the signal sequence.
SEQ ID NOs: 18 to 32 show the sequences used in the Examples.
SEQ ID NO: 33 shows the polynucleotide sequence encoding one subunit of α-HL-Q.
SEQ ID NO: 34 shows the amino acid sequence of one subunit of α-HL-Q.
SEQ ID NO: 35 shows the polynucleotide sequence encoding one subunit of α-HL-E287C-QC-D5FLAGH6.
SEQ ID NO: 36 shows the amino acid sequence of one subunit of α-HL-E287C-QC-D5FLAGH6.
SEQ ID NO: 37 shows the polynucleotide sequence encoding one subunit of α-henaolysin-E111N/K147N (α-HL-NN; Stoddart et al., PNAS, 2009; 106(19): 7702-7707).
SEQ ID NO: 38 shows the amino acid sequence of one subunit of α-HL-NN.
SEQ ID NO: 39 shows the sequence used in Example 5.
SEQ ID NO: 40 and 41 show the sequences used in Example 6.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "an analyte" includes two or more analytes, reference to "a detector" includes two or more such detectors, reference to "a pore" includes two or more such pores, reference to "a nucleic acid sequence" includes two or more such sequences, and the like.

All publications, patents and patent applications cited herein, whether supra or infra, are hereby incorporated by reference in their entirety.

Methods of the Invention

The invention provides a method for determining the presence, absence or characteristics of an analyte. The method comprises coupling the analyte to a membrane and allowing the analyte to interact with a detector present in the membrane. The presence, absence or characteristics of the analyte is thereby determined. In one embodiment, the invention provides a method for determining the presence or absence of an analyte, comprising (a) coupling the analyte to a membrane and (b) allowing the analyte to interact with a detector present in the membrane and thereby determining the presence or absence of the analyte.

As discussed above, coupling the analyte to a membrane containing the detector by several orders of magnitude the amount of analyte required. The method is of course advantageous for detecting analytes that are present at low concentrations. The method preferably allows the presence or characteristics of the analyte to be determined when the analyte is present at a concentration of from about 0.001 pM to about 1 nM, such as less than 0.01 pM, less than 0.1 pM, less than 1 pM, less than 10 pM or less than 100 pM.

The method of the invention is particularly advantageous for nucleic acid sequencing because, as discussed above, only small amounts of purified nucleic acid can be obtained from human blood. The method preferably allows estimating the sequence of, or allows sequencing of, a target polynucleotide that is present at a concentration of from about 0.001 pM to about 1 nM, such as less than 0.01 pM, less than 0.1 pM, less than 1 pM, less than 10 pM or less than 100 pM.

Coupling one end of a polynucleotide to the membrane (even temporarily) also means that the end will be prevented from interfering with the nanopore-based sequencing process. This is discussed in more detail below with reference to the Exonuclease Sequencing method of the invention.

The method of the invention may comprise determining or measuring one or more characteristics of an analyte, such as a polynucleotide. The method may involve determining or measuring two, three, four or five or more characteristics of the analyte, such as a polynucleotide. For polynucleotides, the one or more characteristics are preferably selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified. Any combination of (i) to (v) may be determined or measured in accordance with the invention. The method preferably comprises estimating the sequence of or sequencing a polynucleotide.

Analyte

The analyte can be any substance. Suitable analytes include, but are not limited to, metal ions, inorganic salts, polymers, such as a polymeric acids or bases, dyes, bleaches, pharmaceuticals, diagnostic agents, recreational drugs, explosives and environmental pollutants.

The analyte can be an analyte that is secreted from cells. Alternatively, the analyte can be an analyte that is present inside cells such that the analyte must be extracted from the cells before the invention can be carried out.

The analyte is preferably an amino acid, peptide, polypeptide, a protein or a polynucleotide. The amino acid, peptide, polypeptide or protein can be naturally-occurring or non-naturally-occurring. The polypeptide or protein can include within it synthetic or modified amino acids. A number of different types of modification to amino acids are known in the art. For the purposes of the invention, it is to be understood that the analyte can be modified by any method available in the art.

The protein can be an enzyme, antibody, hormone, growth factor or growth regulatory protein, such as a cytokine. The cytokine may be selected from an interleukin, preferably IFN-1, IL-2, IL-4, IL-5, IL-6, IL-10, IL-12 or IL-13, an interferon, preferably IL-γ or other cytokines such as TNF-α. The protein may be a bacterial protein, fungal protein, virus protein or parasite-derived protein. Before it is contacted with the pore or channel, the protein may be unfolded to form a polypeptide chain.

The analyte is most preferably a polynucleotide, such as a nucleic acid. Polynucleotides are discussed in more detail below. A polynucleotide may be coupled to the membrane at its 5' end or 3' end or at one or more intermediate points along the strand. The polynucleotide can be single stranded or double stranded as discussed below. The polynucleotide may be circular. The polynucleotide may be an aptamer, a probe which hybridises to microRNA or microRNA itself (Wang, Y. et al, Nature Nanotechnology, 2011, 6, 668-674).

When the analyte is a probe which hybridises to microRNA, the probe may be coupled permanently (FIG. 23A) or transiently (FIGS. 23B-C) to the membrane. The probe itself may be adapted to couple directly to the membrane or may hybridise to a complementary polynucleotide which has been adapted to couple to the membrane. The analyte may be a complex of microRNA hybridised to a probe where the probe has distinctive sequences or barcodes enabling it to be identified unambiguously.

When the analyte is an aptamer, the aptamer may be coupled permanently or transiently to the membrane. The aptamer itself may be adapted to couple directly to the membrane or may hybridise to a complementary polynucleotide which has been adapted to couple to the membrane. The aptamer may be bound or unbound to a protein analyte and the ultimate purpose of detecting the aptamer may be to detect the presence, absence or characteristics of a protein analyte to which it binds.

The analyte is present in any suitable sample. The invention is typically carried out on a sample that is known to contain or suspected to contain the analyte. The invention may be carried out on a sample that contains one or more analytes whose identity is unknown. Alternatively, the invention may be carried out on a sample to confirm the identity of one or more analytes whose presence in the sample is known or expected.

The sample may be a biological sample. The invention may be carried out in vitro on a sample obtained from or extracted from any organism or microorganism. The organism or microorganism is typically archaean, prokaryotic or eukaryotic and typically belongs to one the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

Membrane

Any membrane may be used in accordance with the invention. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units that are polymerized together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer.

Archaebacterial bipolar tetraether lipids are naturally occurring lipids that are constructed such that the lipid forms a monolayer membrane. These lipids are generally found in extremophiles that survive in harsh biological environments, thermophiles, halophiles and acidophiles. Their stability is believed to derive from the fused nature of the final bilayer. It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompass a range of phase behaviours from vesicles through to laminar membranes. Membranes formed from these triblock copolymers hold several advantages over biological lipid membranes. Because the triblock copolymer is synthesized, the exact construction can be carefully controlled to provide the correct chain lengths and properties required to form membranes and to interact with pores and other proteins.

Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customize polymer based membranes for a wide range of applications.

In a preferred embodiment, the invention provides a method for determining the presence, absence or characteristics of an analyte, comprising (a) coupling the analyte to a membrane comprising a triblock copolymer, optionally wherein the membrane is modified to facilitate the coupling, and (b) allowing the analyte to interact with a detector present in the membrane and thereby determining the presence, absence- or characteristics of the analyte. As discussed above, a triblock copolymer is a polymer formed from three different monomer sub-units.

The amphiphilic molecules may be chemically-modified or functionalised to facilitate coupling of the analyte.

The amphiphilic layer may be a monolayer or a bilayer. The amphiphilic layer is typically planar. The amphiphilic layer may be curved.

Amphiphilic membranes are typically naturally mobile, essentially acting as two dimensional fluids with lipid diffusion rates of approximately $10^{-8}$ cm s−1. This means that the detector and coupled analyte can typically move within an amphiphilic membrane.

The membrane is preferably a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has evaporated, the solution/air interfaces on either side of the aperture are physically moved up and down past the aperture until a bilayer is formed. Planar lipid bilayers may be formed across an aperture in a membrane or across an opening into a recess.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

Tip-dipping bilayer formation entails touching the aperture surface (for example, a pipette tip) onto the surface of a test solution that is carrying a monolayer of lipid. Again, the lipid monolayer is first generated at the solution/air interface by allowing a drop of lipid dissolved in organic solvent to evaporate at the solution surface. The bilayer is then formed by the Langmuir-Schaefer process and requires mechanical automation to move the aperture relative to the solution surface.

For painted bilayers, a drop of lipid dissolved in organic solvent is applied directly to the aperture, which is submerged in an aqueous test solution. The lipid solution is spread thinly over the aperture using a paintbrush or an equivalent. Thinning of the solvent results in formation of a lipid bilayer. However, complete removal of the solvent from the bilayer is difficult and consequently the bilayer formed by this method is less stable and more prone to noise during electrochemical measurement.

Patch-clamping is commonly used in the study of biological cell membranes. The cell membrane is clamped to the end of a pipette by suction and a patch of the membrane becomes attached over the aperture. The method has been adapted for producing lipid bilayers by clamping liposomes which then burst to leave a lipid bilayer sealing over the aperture of the pipette. The method requires stable, giant and unilamellar liposomes and the fabrication of small apertures in materials having a glass surface.

Liposomes can be formed by sonication, extrusion or the Mozafari method (Colas et al. (2007) Micron 38:841-847).

In a preferred embodiment, the lipid bilayer is formed as described in International Application No. PCT/GB08/004127 (published as WO 2009/077734). Advantageously in this method, the lipid bilayer is formed from dried lipids. In a most preferred embodiment, the lipid bilayer is formed across an opening as described in WO2009/077734 (PCT/GB08/004127).

A lipid bilayer is formed from two opposing layers of lipids. The two layers of lipids are arranged such that their hydrophobic tail groups face towards each other to form a hydrophobic interior. The hydrophilic head groups of the lipids face outwards towards the aqueous environment on each side of the bilayer. The bilayer may be present in a number of lipid phases including, but not limited to, the liquid disordered phase (fluid lamellar), liquid ordered phase, solid ordered phase (lamellar gel phase, interdigitated gel phase) and planar bilayer crystals (lamellar sub-gel phase, lamellar crystalline phase).

Any lipid composition that forms a lipid bilayer may be used. The lipid composition is chosen such that a lipid bilayer having the required properties, such surface charge, ability to support membrane proteins, packing density or mechanical properties, is formed. The lipid composition can comprise one or more different lipids. For instance, the lipid composition can contain up to 100 lipids. The lipid composition preferably contains 1 to 10 lipids. The lipid composition may comprise naturally-occurring lipids and/or artificial lipids.

The lipids typically comprise a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradeconic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester.

The lipids can also be chemically-modified. The head group or the tail croup of the lipids may be chemically-modified. Suitable lipids whose head groups have been chemically-modified include, but are not limited to, PEG-modified lipids, such as 1,2-Diacyl-sn-Glycero-3-Phosphoethanolamine-N-[Methoxy(Polyethylene glycol)-2000]; functionalised PEG Lipids, such as 1,2-Distearoyl-sn-Glycero-3 Phosphoethanolamine-N-[Biotinyl(Polyethylene Glycol)2000]; and lipids modified for conjugation, such as 1,2-Dioleoyl-sn-Glycero-3-Phosphoethanolamine-N-(succinyl) and 1,2-Dipalmitoyl-sn-Glycero-3-Phosphoethanolamine-N-(Biotinyl). Suitable lipids whose tail groups have been chemically-modified include, but are not limited to, polymerisable lipids, such as 1,2-bis(10,12-tricosadiynoyl)-sn-Glycero-3-Phosphocholine; fluorinated lipids, such as 1-Palmitoyl-2-(16-Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine. The lipids may be chemically-modified or functionalised to facilitate coupling of the analyte.

The amphiphilic layer, for example the lipid composition, typically comprises one or more additives that will affect the properties of the layer. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lyso-phospholipids, such as 1-Acyl-2-Hydroxy-sn-Glycero-3-Phosphocholine; and ceramides.

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as Si3N4, Al2O3, and SiO, organic and inorganic polymers such as polyamide, plastics such as Teflon® or elastomers such as two-component addition-cure silicone rubber, and glasses. The solid state layer may be formed from graphene. Suitable graphene layers are disclosed in International Application No. PCT/US2008/010637 (published as WO 2009/035647).

Coupling

The analyte may be coupled to the membrane using any known method. If the membrane is an amphiphilic layer, such as a lipid bilayer, the analyte is preferably coupled to the membrane via a polypeptide present in the membrane or a hydrophobic anchor present in the membrane. The hydrophobic anchor is preferably a lipid, fatty acid, sterol, carbon nanotube, polypeptide, protein or amino acid, for example cholesterol, palmitate or tocopherol. In preferred embodiments, the analyte is not coupled to the membrane via the detector.

The components of the membrane, such as the amphiphilic molecules or lipids, may be chemically-modified or functionalised to facilitate coupling of the analyte to the membrane either directly or via one or more linkers. Examples of suitable chemical modifications and suitable ways of functionalising the components of the membrane are discussed in more detail below. Any proportion of the membrane components may be functionalised, for example at least 0.01%, at least 0.1%, at least 1%, at least 10%, at least 25%, at least 50% or 100%.

The analyte may be coupled directly to the membrane. The analyte may be coupled directly to the membrane at one or more, such as 2, 3, 4 or more, points.

The analyte is preferably coupled to the membrane via a linker. The analyte may be coupled to the membrane via one or more, such as 2, 3, 4 or more, linkers. One linker may couple more than one, such as 2, 3, 4 or more, analytes to the membrane.

The analyte may be coupled to the membrane directly at one or more points and via one or more linkers.

Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. If the analyte is itself a polynucleotide, it may hybridize to a complementary sequence on the circular polynucleotide linker.

Functionalised linkers and the ways in which they can couple molecules are known in the art. For instance, linkers functionalised with maleimide groups will react with and attach to cysteine residues in proteins. In the context of this invention, the protein may be present in the membrane, may be the analyte itself or may be used to bind to the analyte. This is discussed in more detail below.

Crosslinkage of analytes can be avoided using a "lock and key" arrangement. Only one end of each linker may react together to form a longer linker and the other ends of the linker each react with the analyte or membrane respectively. Such linkers are described in International Application No. PCT/GB10/000132 (published as WO 2010/086602).

The use of a linker is preferred in the sequencing embodiments discussed below. If a polynucleotide analyte is permanently coupled directly to the membrane, then some sequence data will be lost as the sequencing run cannot continue to the end of the polynucleotide due to the distance between the membrane and the detector. If a linker is used, then the polynucleotide analyte can be processed to completion. The coupling may be permanent or stable. In other words, the coupling may be such that the analyte remains coupled to the membrane during the method. The coupling may be transient. In other words, the coupling may be such that the analyte decouples from the membrane during the method. For certain applications, such as aptamer detection, the transient nature of the coupling is preferred. If a permanent or stable linker is attached directly to either the 5' or 3' end of a polynucleotide and the linker is shorter than the distance between the bilayer and the nanopore's channel or the polynucleotide binding protein's active site, then some sequence data will be lost as the sequencing run cannot continue to the end of the polynucleotide. If the coupling is transient, then when the coupled end randomly becomes free of the bilayer, then the polynucleotide can be processed to completion. Chemical groups that form permanent/stable or transient links with the membrane are discussed in more detail below. The analyte may be transiently coupled to an amphiphilic layer or lipid bilayer using cholesterol or a fatty acyl chain. Any fatty acyl chain having a length of from 6 to 30 carbon atom, such as hexadecanoic acid, may be used.

In preferred embodiments, a polynucleotide analyte, such as a nucleic acid, is coupled to an amphiphilic layer such as a lipid bilayer. Coupling of nucleic acids to synthetic lipid bilayers has been carried out previously with various different tethering strategies. These are summarised in Table 3 below.

TABLE 3

| Attachment group | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |

TABLE 3-continued

| Attachment group | Type of coupling | Reference |
|---|---|---|
| Biotin | Stable | Nikolov, V., R. Lipowsky, et al. (2007). "Behavior of giant vesicles with anchored DNA molecules." *Biophys J* 92(12): 4356-68 |
| Cholestrol | Transient | Pfeiffer, I. and F. Hook (2004). "Bivalent cholesterol-based coupling of oligonucletides to lipid membrane assemblies." *J Am Chem Soc* 126(33): 10224-5 |
| Surfactant (eg. Lipid, Palmitate, etc) | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Synthetic polynucleotide analytes or linkers may be functionalised using a modified phosphoramidite in the synthesis reaction, which is easily compatible for the direct addition of suitable coupling moieties, such as cholesterol, tocopherol or palmitate, as well as for reactive groups, such as thiol, cholesterol, lipid and biotin groups. These different attachment chemistries give a suite of options for attachment to target polynucleotides. Each different modification group tethers the polynucleotide in a slightly different way and coupling is not always permanent so giving different dwell times for the analyte to the bilayer. The advantages of transient coupling are discussed above.

Coupling of polynucleotides to a linker or to a functionalised membrane can also be achieved by a number of other means provided that a complementary reactive group or a tether can be added to the target polynucleotide. The addition of reactive groups to either end of DNA has been reported previously. A thiol group can be added to the 5' of ssDNA or dsDNA using T4 polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). An azide group could be added to the 5'-phosphate of ssDNA or dsDNA using T4 polynucleotide kinase and γ-[2-Azidoethyl]-ATP or γ-[6-Azidohexyl]-ATP. Using thiol or Click chemistry a tether, containing either a thiol, iodoacetamide OPSS or maleimide group (reactive to thiols) or a DIBO (dibenzocyclooxtyne) or alkyne group (reactive to azides), can be covalently attached to the analyte. A more diverse selection of chemical groups, such as biotin. thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82). Example 3 below describes how DNA can be coupled to a lipid bilayer using streptavidin/biotin. Streptavidin/biotin coupling may be used for any other analyte. It may also be possible that tethers could be directly added to target polynucleotides using terminal transferase with suitably modified nucleotides (e.g. cholesterol or palmitate).

Alternatively, the reactive group or tether could be considered to be the addition of a short piece of polynucleotide, such as DNA, complementary to one already coupled to the bilayer, so that attachment can be achieved via hybridisation. In this case, the reactive group may be a single strand or double strand polynucleotide. The reactive group may be ligated to a single strand or double strand polynucleotide analyte. Ligation of short pieces of ssDNA have been reported using T4 RNA ligase I (Troutt, A. B., M. G.

McHeyzer-Williams, et al. (1992). "Ligation-anchored PCR: a simple amplification technique with single-sided specificity." Proc Natl Acad Sci USA 89(20): 9823-5). Alternatively, either ssDNA or dsDNA could be ligated to native analyte dsDNA and then the two strands separated by thermal or chemical denaturation. To native dsDNA, it is possible to add either a piece of ssDNA to one or both of the ends of the duplex, or dsDNA to one or both ends. For addition of single stranded nucleic acids to the native DNA this can be achieved using T4 RNA ligase I as for ligation to other regions of single stranded nucleic acids. For addition of dsDNA to native duplex DNA then ligation can be "blunt-ended", with complementary 3' dA/dT tails on the native DNA and adapter respectively (as is routinely done for many sample prep applications to prevent concatemer or dimer formation) or using "sticky-ends" generated by restriction digestion of the native DNA and ligation of compatible adapters. Then, when the duplex is melted, each single strand will have either a 5' or 3' modification if ssDNA was used for ligation or a modification at the 5' end, the 3' end or both if dsDNA was used for ligation. If the polynucleotide is a synthetic strand, the coupling chemistry can be incorporated during the chemical synthesis of the polynucleotide. For instance, the polynucleotide can be synthesised using a primer having a reactive group attached to it.

Adenylated nucleic acids (AppDNA) are intermediates in ligation reactions, where an adenosine-monophostate is attached to the 5'-phosphate of the nucleic acid. Various kits are available for generation of this intermediate, such as the 5' DNA Adenylation Kit from NEB. By substituting ATP in the reaction for a modified nucleotide triphosphate, then addition of reactive groups (such as thiols, amines, biotin, azides, etc) to the 5' of DNA should be possible. It may also be possible that tethers could be directly added to target polynucleotides using a 5' DNA adenylation kit with suitably modified nucleotides (e.g. cholesterol or palmitate).

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. By using an antisense primer single or multiple nucleotides can be added to 3' end of single or double stranded DNA by employing a polymerase. Examples of polymerases which could be used include, but are not limited to, Terminal Transferase, Klenow and *E. coli* Poly(A) polymerase). By substituting ATP in the reaction for a modified nucleotide triphosphate then reactive groups, such as a cholesterol, thiol, amine, azide, biotin or lipid, can be incorporated into the DNA. Therefore, each copy of the target amplified DNA will contain a reactive group for coupling.

Ideally, the analyte is coupled to the membrane without having to functionalise the analyte. This can be achieved by anchoring a binding group, such as a polynucleotide binding protein or a chemical group, to the membrane and allowing the binding group to interact with the analyte or by functionalizing the membrane. The binding group may be coupled to the membrane by any of the methods described herein. In particular, the binding group may be coupled to the membrane using one or more linkers, such as maleimide functionalised linkers.

In this embodiment, the analyte is typically RNA, DNA, PNA, TNA or LNA and may be double or single stranded. This embodiment is particularly suited to genomic DNA analytes.

The binding group can be any group that interacts with single or double stranded nucleic acids, specific nucleotide sequences within the analyte or patterns of modified nucleotides within the analyte, or any other ligand that is present on the polynucleotide.

Suitable binding proteins include *E. coli single stranded binding protein, P5* single stranded binding protein, T4 gp32 single stranded binding protein, the TOPO V dsDNA binding region, human histone proteins, *E. coli* HU DNA binding protein and other archaeal, prokaryotic or eukaryotic single- or double-stranded nucleic acid binding proteins, including those listed below.

The specific nucleotide sequences could be sequences recognised by transcription factors, ribosomes, endonucleases, topoisomerases or replication initiation factors. The patterns of modified nucleotides could be patterns of methylation or damage.

The chemical group can be any group which intercalates with or interacts with a polynucleotide analyte. The group may intercalate or interact with the polynucleotide analyte via electrostatic, hydrogen bonding or Van der Waals interactions. Such groups include a lysine monomer, poly-lysine (which will interact with ssDNA or dsDNA), ethidium bromide (which will intercalate with dsDNA), universal bases or universal nucleotides (which can hybridise with any polynucleotide analyte) and osmium complexes (which can react to methylated bases). A polynucleotide analyte may therefore be coupled to the membrane using one or more universal nucleotides attached to the membrane. Each universal nucleotide residue may be attached to the membrane using one or more linkers. Examples of universal bases include inosine, 3-nitropyrrole, 5-nitroindole, 4-nitroindole, 6-nitroindole, 3,4-dihydro-pyrimido[4,5-c][1,2]oxazin-7-one (dP), 2-dimethylaminomethyleneamino-6-methyoxyaminopurine (dK), deoxy inosine, deoxy nebularine.

In this embodiment at least 1%, at least 10%, at least 25%, at least 50% or 100% of the membrane components may be functionalized.

Where the binding group is a protein, it may be able to anchor directly into the membrane without further functonalisation, for example if it already has an external hydrophobic region which is compatible with the membrane. Examples of such proteins include transmembrane proteins. Alternatively the protein may be expressed with a genetically fused hydrophobic region which is compatible with the membrane. Such hydrophobic protein regions are know in the art.

The binding group is preferably mixed with the analyte before contacting with the membrane, but the binding group may be contacted with the membrane and subsequently contacted with the analyte.

In another aspect the analyte may be functionalised, using methods described above, so that it can be recognised by a specific binding group. Specifically the analyte may be functionalised with a ligand such as biotin (for binding to streptavidin), amylose (for binding to maltose binding protein or a fusion protein), Ni-NTA (for binding to poly-histidine or poly-histidine tagged proteins) or a peptides (such as an antigen).

According to a further aspect, the binding group may be used to couple polynucleotide analyte to the membrane when the analyte has bound to a polynucleotide adapter. Specifically the analyte binds to an adaptor which comprises a leader sequence designed to preferentially thread into a detector such as a nanopore. Such a leader sequence may comprise a homopolymeric polynucleotide or an abasic region. The adaptor typically is designed to hybridise to a linker and to ligate to or hybridise to the analyte. This creates competition between the analyte and the adaptor to enter the detector. If the linker comprises a binding group, the greater length of the analyte compared to the adapter means that several linkers can bind to the analyte simultaneously, thus increasing the concentration of analyte relative to that of the adapter.

Any of the methods discussed above for coupling polynucleotides to amphiphilic layers, such as lipid bilayers, can of course be applied to other analyte and membrane combinations. In some embodiments, an amino acid, peptide, polypeptide or protein is coupled to a lipid bilayer. Various methodologies for the chemical attachment of such analytes are available. An example of a molecule used in chemical attachment is EDC (1-ethyl-3-[3-dimethylaminopropyl]carbodiimide hydrochloride). Reactive groups can also be added to the 5' of DNA using commercially available kits (Thermo Pierce, Part No. 22980). Suitable methods include, but are not limited to, transient affinity attachment using histidine residues and Ni-NTA, as well as more robust covalent attachment by reactive cysteines, lysines or non natural amino acids.

Detector

The detector can be any structure that provides a readable signal in response to the presence, the absence or the characteristics of the analyte. The detector can be any structure that provides a readable signal in response to the presence or the absence of the analyte. Suitable detectors are known in the art. They include, but are not limited to transmembrane pores, tunnelling electrodes, classis electrodes, nanotubes, FETs (field-effect transistors) and optical detectors, such as atomic force microscopes (AFMs) and scanning tunneling microscopes (STMs).

In preferred embodiments, the detector detects the analyte using electrical means. Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

In other preferred embodiments, the detector does not detect the analyte using fluorescent means.

The detector preferably comprises a transmembrane pore. A transmembrane pore is a structure that permits hydrated ions driven by an applied potential to flow from one side of the membrane to the other side of the membrane.

The transmembrane pore is preferably a transmembrane protein pore. A transmembrane protein pore is a polypeptide or a collection of polypeptides that permits hydrated ions, such as analyte, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits analyte such as nucleotides to flow from one side of the membrane, such as a lipid bilayer, to the other. The transmembrane protein pore preferably allows a polynucleotide or nucleic acid, such as DNA or RNA, to be move through the pore.

The transmembrane protein pore may be a monomer or an oligomer. The pore is preferably made up of several repeating subunits, such as 6, 7 or 8 subunits. The pore is more preferably a heptameric or octameric pore.

The transmembrane protein pore typically comprises a barrel or channel through which the ions may flow. The subunits of the pore typically surround a central axis and contribute strands to a transmembrane 13 barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids. The nucleotide detection can be facilitated with an adaptor. This is discussed in more detail below.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and α outer membrane proteins, such as WZA and ClyA toxin. The transmembrane pore may be derived from Msp or from α-hemolysin (α-HL).

For Strand Sequencing, the transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. The pore may also comprise one or more constructs which comprise two or more covalently attached monomers derived from Msp. Suitable pores are disclosed in International Application No. PCT/GB2012/050301 (claiming priority from U.S. Provisional Application No. 61/441,718). Preferably the pore is derived from MspA or a homolog or paralog thereof.

A monomer derived from Msp comprises the sequence shown in SEQ ID NO: 2 or a variant thereof. SEQ ID NO: 2 is the NNN-RRK mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into a lipid bilayer along with other appropriate subunits and its ability to oligomerise to form a pore may be determined. Methods are known in the art for inserting subunits into membranes, such as lipid bilayers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H.

Bayley. J. Am. Chem. Soc. 2005, 127, 6502-6503 and International Application No. PCT/GB2006/001057 (published as WO 2006/100484).

Preferred variants are disclosed in International Application No. PCT/GB2012/050301 (claiming priority from U.S. Provisional Application No. 61/441,718). Particularly preferred variants include, but are not limited to, those comprising the following substitution(s): L88N; L88S; L88Q; L88T; D90S; D90Q; D90Y; I105L; I105S; Q126R; G75S; G77S; G75S, G77S, L88N and Q126R; G75S, G77S, L88N, D90Q and Q1.26R; D90Q and Q126R; L88N, D90Q and Q126R; L88S and D90Q; L88N and D90Q; E59R; G75Q; G75N; G75S; G75T; G77Q; G77N; G77S; G77T; I78L; S81N; T83N; N86S; N86T; I87F; I87V; I871L; L88N; L88S; L88Y; L88F; L88V; L88Q; L88T; I89F; I89V; I89L; N90S; N90Q; N90L; N90Y; N91S; N91Q; N91L; N91M; N91I; N91A; N91V; N91G; G92A; G92S; N93S; N93A; N93T; I94L; T95V; A96R; A96D; A96V; A96N; A96S; A96T; P97S; P98S; F99S; G100S; L101F; N102K; N102S; N102T; S103A; S103Q; S103N; S103G; S103T; V104I; I105Y; I105L; I105A; I105Q; I105N; I105S; I105T; T106F; T106I; T106V; T106S; N108P; N108S; D90Q and I105A; D90S and G92S; L88T and D90S; I87Q and D90S; I89Y and D90S; L88N and I89F; L88N and I89Y; D90S and G92A; D90S and I94N; D90S and V104I; L88D and I105K; L88N and Q126R; L88N, D90Q and D91R; L88N, D90Q and D91S; L88N, D90Q and I105V; D90Q, D93S and I105A; N91Y; N90Y and N91G; N90G and N91Y; N90G and N91G; I05G; N90R; N91R; N90R and N91R; N90K; N91K; N90K and N91K; N90Q and N91G; N90G and N91Q; N90Q and N91Q; R118N; N91C; N90C; N90W; N91W; N90K; N91K; N90R; N91R; N90S and N91S; N90Y and I105A; N90G and I105A; N90Q and I105A; N90S and I105A; L88A and I105A; L88S and I105S; L88N and I105N; N90G and N93G; N90G; N93G; N900 and N91A; I105K; I105R; I105V; I105P; I105W; L88R; L88A; L88G; L88N; N90R and I105A; N90S and I105A; L88A and I105A; L88S and I105S; L88N and I105N; L88C; S103C; and I105C.

In addition to the specific mutations discussed above, the variant may include other mutations. Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F. et al (1990) J Mol Biol 215:403-10. Software for performing BLAST analyses is publicly available through the National Center for Biotechnology Information (http://www.ncbi.nlm.nih.gov/).

SEQ ID NO: 2 is the NNN-RRK mutant of the MspA monomer. The variant may comprise any of the mutations in the MspB, C or D monomers compared with MspA. The mature forms of MspB, C and D are shown in SEQ ID NOs: 15 to 17. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 4 below. Where amino acids have similar polarity, this can also be determined by reference to the hydropathy scale for amino acid side chains in Table 5.

TABLE 4

Chemical properties of amino acids

| Ala | aliphatic, hydrophobic, neutral | Met | hydrophobic, neutral |
| --- | --- | --- | --- |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

TABLE 5

Hydropathy scale

| Side Chain | Hydropathy |
| --- | --- |
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |

TABLE 5-continued

Hydropathy scale

| Side Chain | Hydropathy |
|---|---|
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a 0-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomer derived from Msp may be labelled with a revealing label. The revealing label may be any suitable label which allows the pore to be detected. Suitable labels include, but are not limited to fluorescent molecules, radioisotopes. e.g. $^{125}$I, $^{35}$S, enzymes, antibodies, antigens, polynucleotides and ligands such as biotin.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with NaBH$_4$, amidination with methylacetimidate or acylation with acetic anhydride.

The monomer derived from Msp can be produced using standard methods known in the art. The monomer derived from Msp may be made synthetically or by recombinant means. For example, the pore may be synthesised by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed below.

For Exonuclease Sequencing, the transmembrane protein pore is preferably derived from α-hemolysin (α-HL). The wild type α-HL pore is formed of seven identical monomers or subunits (i.e. it is heptameric). The sequence of one monomer or subunit of α-hemolysin M113R is shown in SEQ ID NO: 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 21.3, 217, 21.8, 223 to 228, 236 to 242, 262 to 265, 272 to 274, 287 to 290 and 294 of SEQ ID NO: 4 form loop regions. Residues 113 and 147 of SEQ ID NO: 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homoheptamer) or different (heteroheptamer).

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into a lipid bilayer along with other appropriate subunits and its ability to oligomerise to form a pore may be determined. Methods are known in the art for inserting subunits into membranes, such as lipid bilayers. Suitable methods are discussed above.

The variant may include modifications that facilitate covalent attachment to or interaction with a nucleic acid binding protein. The variant preferably comprises one or more reactive cysteine residues that facilitate attachment to the nucleic acid binding protein. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (A8C, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with nucleotides or facilitate orientation of a molecular adaptor as discussed below. The variant may also contain modifications that facilitate covalent attachment of a molecular adaptor.

In particular, the variant preferably contains a glutamine at position 139 of SEQ ID NO: 4. The variant preferably has a cysteine at position 119, 121 or 135 of SEQ ID NO: 4. A variant of SEQ ID NO: 4 may have the wild-type methionine reintroduced at position 113.

Preferred variants of SEQ ID NO: 4 have a methionine at position 113 (R113M), a cysteine at position 135 (L135C) and a glutamine at position 139 (N139Q). Other preferred variants of SEQ ID NO: 4 have a methionine at position 113 (R113M) and a glutamine at position 139 (N139Q). One such variant is shown in SEQ ID NO: 34. A preferred transmembrane protein pore for use in Exonuclease Sequencing comprises (a) one monomer comprising a variant of SEQ ID NO: 4 having a methionine at position 113 (R113M), a cysteine at position 135 (L135C) and a glutamine at position 139 (N139Q) and (b) six monomers each comprising a variant of SEQ ID NO: 4 having a methionine at position 113 (RI13M) and a glutamine at position 139 (NI 39Q). The six monomers in (b) each preferably comprise the sequence shown in SEQ ID NO: 34.

The variant may be a naturally occurring variant which is expressed naturally by an organism, for instance by a *Staphylococcus* bacterium. Alternatively, the variant may be expressed in vitro or recombinantly by a bacterium such as *Escherichia coli*. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may be fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135, 113 and 1.39 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a subunit or variant.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of α-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form β-strands are discussed above. One. or more modifications can be made to the regions of SEQ ID NO: 4 that form β-strands as long as the resulting variant retains its ability to form a pore. Specific modifications that can be made to the β-strand regions of SEQ ID NO: 4 are discussed above.

A variant of SEQ ID NO: 4 preferably includes one or more modifications, such as substitutions, additions or deletions, within its α-helices and/or loop regions. Amino acids that form α-helices and loops are discussed above.

The variant may be modified to assist its identification or purification as discussed above.

A particularly preferred pore for use in Exonuclease Sequencing comprises one subunit shown in SEQ ID NO: 36 (i.e. α-HL-E287C-QC-D5FLAGH6) and six subunits shown in SEQ ID NO: 34 (i.e. α-HL-Q).

Pores derived from α-HL can be made as discussed above with reference to pores derived from Msp.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

In some embodiments, the transmembrane protein pore comprises a molecular adaptor that facilitates detection of the analyte. Pores for use in Exonuclease Sequencing typically comprise a molecular adaptor.

The molecular adaptor may directly facilitate detection of the analyte by mediating an interaction between the pore and the analyte. In such embodiments, the presence of the adaptor improves the host-guest chemistry of the pore and the analyte and thereby improves the ability of the pore to detect the analyte. The principles of host-guest chemistry are well-known in the art. The adaptor has an effect on the physical or chemical properties of the pore that improves its interaction with the analyte. The adaptor may alter the charge of the barrel or channel of the pore or specifically interact with or bind to the analyte thereby facilitating its interaction with the pore.

In other embodiments, the molecular adaptor indirectly facilitates detection of the analyte by mediating an interaction between the pore and a product, such as a fragment, formed from processing of the analyte. For instance, for Exonuclease Sequencing, the molecular adaptor facilitates an interaction between the pore and individual nucleotides digested from the polynucleotide analyte. In such embodiments, the presence of the adaptor improves the host-guest chemistry of the pore and the individual nucleotides and thereby improves the ability of the pore to detect the individual nucleotides. The adaptor has an effect on the physical or chemical properties of the pore that improves its interaction with the individual nucleotides. The adaptor may alter the charge of the barrel or channel of the pore or specifically interact with or bind to the individual nucleotides thereby facilitating their interaction with the pore.

The molecular adaptor is preferably a cyclic molecule such as a cyclodextrin, a species that is capable of hybridization, a DNA binder or interchelator, a peptide or peptide analogue, a synthetic polymer, an aromatic planar molecule, a small positively-charged molecule or a small molecule capable of hydrogen-bonding.

The adaptor may be cyclic. A cyclic adaptor preferably has the same symmetry as the pore. The adaptor preferably has eight-fold symmetry if the pore is derived from Msp since Msp typically has eight subunits around a central axis. The adaptor preferably has seven-fold symmetry if the pore is derived from α-HL since α-HL typically has seven subunits around a central axis. This is discussed in more detail below.

The adaptor typically interacts with the analyte via host-guest chemistry. The adaptor is typically capable of interacting with a nucleotide or polynucleotide. The adaptor comprises one or more chemical groups that are capable of interacting with the analyte, such as the nucleotide or polynucleotide. The one or more chemical groups preferably interact with the analyte, nucleotide or polynucleotide by non-covalent interactions, such as hydrophobic interactions, hydrogen bonding, Van der Waal's forces, π-cation interactions and/or electrostatic forces. The one or more chemical groups that are capable of interacting with the nucleotide or polynucleotide are preferably positively charged. The one or more chemical groups that are capable of interacting with the nucleotide or polynucleotide more preferably comprise amino groups. The amino groups can be attached to primary, secondary or tertiary carbon atoms. The adaptor even more preferably comprises a ring of amino groups, such as a ring of 6, 7 or 8 amino groups. The adaptor most preferably comprises a ring of seven or eight amino groups. A ring of protonated amino groups may interact with negatively charged phosphate groups in the nucleotide or polynucleotide.

The correct positioning of the adaptor within the pore can be facilitated by host-guest chemistry between the adaptor and the pore. The adaptor preferably comprises one or more chemical groups that are capable of interacting with one or more amino acids in the pore. The adaptor more preferably comprises one or more chemical groups that are capable of interacting with one or more amino acids in the pore via non-covalent interactions, such as hydrophobic interactions, hydrogen bonding, Van der Waal's forces, n-cation interactions and/or electrostatic forces. The chemical groups that are capable of interacting with one or more amino acids in the pore are typically hydroxyls or amines. The hydroxyl groups can be attached to primary, secondary or tertiary carbon atoms. The hydroxyl groups may form hydrogen bonds with uncharged amino acids in the pore. Any adaptor that facilitates the interaction between the pore and the nucleotide or polynucleotide can be used.

Suitable adaptors include, but are not limited to, cyclodextrins, cyclic peptides and cucurbiturils. The adaptor is preferably a cyclodextrin or a derivative thereof. The cyclodextrin or derivative thereof may be any of those disclosed in Eliseev, A. V., and Schneider, (1994) *J. Am. Chem. Soc.* 116, 6081-6088. The adaptor is more preferably heptakis-6-amino-β-cyclodextrin (am$_7$-βCD), 6-monodeoxy-6-monoamino-β-cyclodextrin (am$_1$-βCD) or heptakis-(6-deoxy-6-guanidino)-cyclodextrin (gu$_7$-βCD). The guanidino group in gu$_7$-βCD has a much higher pKa than the primary amines in am$_7$-βCD and so it more positively charged. This gu$_7$-βCD adaptor may be used to increase the dwell time of the nucleotide in the pore, to increase the accuracy of the residual current measured, as well as to increase the base detection rate at high temperatures or low data acquisition rates.

If a succinimidyl 3-(2-pyridyldithio)propionate (SPDP) crosslinker is used as discussed in more detail below, the adaptor is preferably heptakis(6-deoxy-6-amino)-6-N-mono (2-pyridyl)dithiopropanol-β-cyclodextrin (am$_6$amPDP$_1$-βCD).

More suitable adaptors include γ-cyclodextrins, which comprise 8 sugar units (and therefore have eight-fold symmetry). The γ-cyclodextrin may contain a linker molecule or may be modified to comprise all or more of the modified sugar units used in the β-cyclodextrin examples discussed above.

The molecular adaptor is preferably covalently attached to the pore. The adaptor can be covalently attached to the pore using any method known in the art. The adaptor is typically attached via chemical linkage. If the molecular adaptor is attached via cysteine linkage, the one or more cysteines have preferably been introduced to the mutant by substitution. As discussed above, monomers derived from Msp can comprise a cysteine residue at one or more of positions 88, 90, 91, 103 and 105. Each monomer in the pore may be chemically modified by attachment of a molecular adaptor to one or more, such as 2, 3, 4 or 5, of these cysteines. Alternatively, the monomer may be chemically modified by attachment of a molecule to one or more cysteines introduced at other positions. The molecular adaptor is preferably attached to one or more of positions 90, 91 and 103 of SEQ ID NO: 2.

For pores derived from α-HL, the correct orientation of the adaptor within the barrel or channel of the pore and the covalent attachment of adaptor to the pore can be facilitated using specific modifications to the pore. In particular, every subunit of the pore preferably has the glutamine at position 139 of SEQ ID NO: 2. One or more of the subunits of the pore may have an arginine at position 113 of SEQ ID NO: 2. One or more of the subunits of the pore may have a cysteine at position 119, 121 or 135 of SEQ ID NO: 2 to facilitate attachment of the molecular adaptor to the pore.

The reactivity of cysteine residues may be enhanced by modification of the adjacent residues. For instance, the basic groups of flanking arginine, histidine or lysine residues will change the pKa of the cysteines thiol group to that of the more reactive S⁻ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/GB09/001690 (published as WO 2010/004273), PCT/GB09/001679 (published as WO 2010/004265) or PCT/GB10/000133 (published as WO 2010/086603.

In a preferred embodiment, the detector comprises a polynucleotide binding protein. This allows the method of the invention to be used to sequence polynucleotides or nucleic acids. Polynucleotides are defined below. Examples of polynucleotide binding proteins include, but are not limited to, nucleic acid handling enzymes, such as nucleases, polymerases, topoisomerases, ligases and helicases, and non-catalytic binding proteins such as those classified by SCOP (Structural Classification of Proteins) under the Nucleic acid-binding protein superfamily (50249). The polynucleotide binding protein is preferably modified to remove and/or replace cysteine residues as described in International Application No. PCT/GB10/000133 (published as WO 2010/086603). A preferred polynucleotide binding protein is derived from Phi29 polymerase. The protein preferably comprises the sequence shown in SEQ ID NO: 6 or a variant thereof. This is discussed in more detail below. Other preferred polynucleotide binding proteins for use in the invention include exonuclease I from *E. coli* (SEQ ID NO: 8), exonuclease III enzyme from *E. coli* (SEQ ID NO: 10). RecJ from *T. thermophilus* (SEQ ID NO: 12) and bacteriophage lambda exonuclease (SEQ ID NO: 14) and variants thereof. Three identical subunits of SEQ ID NO: 14 interact to form a trimer exonuclease. The variant is preferably modified to facilitate attachment to the membrane protein and may be any of those discussed in International Application No. PCT/GB09/001679 (published as WO 2010/004265) or PCT/GB10/000133 (published as WO 2010/086603). The protein may be any of SEQ ID NOs: 8, 10, 12, 14, 16, 18, 20, 22, 24, 26, 28, 30, 32, 34, 36, 38, 40, 42, 44, 46, 48 and 50 described in International Application No. PCT/GB10/000133 (published as WO 2010/086603) or a variant thereof discussed in that International application. The polynucleotide binding protein may be attached to the pore in any manner and is preferably attached as described in International Application No. PCT/GB09/001679 (published as WO 2010/004265) or PCT/GB10/000133 (published as WO 2010/086603).

The detector preferably comprises a polynucleotide binding protein in addition to a transmembrane protein pore. Such detectors form modular sequencing systems that may be used in the methods of sequencing of the invention. The polynucleotide binding protein may be attached to the pore, but does not have to be.

In Exonuclease Sequencing, the target polynucleotide is allowed to interact with an exonuclease present in the detector. The exonuclease is typically attached to the pore in the detector. In Strand Sequencing, the detector typically comprises a polymerase in addition to the pore. The target polynucleotide is allowed to interact with the polymerase, such as Phi29 polymerase, present in the detector. The polymerase and pore are typically not attached together, but together form the detector.

For Exonuclease Sequencing, the exonuclease is preferably covalently attached to the transmembrane protein pore. The exonuclease can be covalently attached to the pore using any method known in the art. The pore and protein may be chemically fused or genetically fused. The pore and exonuclease are genetically fused if the whole construct is expressed from a single polynucleotide sequence. Genetic fusion of a pore to an exonuclease is discussed in International Application No. PCT/GB09/00.1679 (published as WO 2010/004265).

If the exonuclease is attached to the pore via cysteine linkage, the one or more cysteines have preferably been introduced to the pore by substitution. Pores derived from Msp can of course comprise cysteine residues at one or more of positions 10 to 15, 51 to 60, 136 to 139 and 168 to 172. These positions are present in loop regions which have low conservation amongst homologues indicating that mutations or insertions may be tolerated. They are therefore suitable for attaching an exonuclease. The reactivity of cysteine residues may be enhanced by modification as described above.

The exonuclease may be attached directly to the pore or via one or more linkers. The exonuclease may be attached to the pore-using the hybridization linkers described in International Application No. PCT/GB10/000132 (published as WO 2010/086602). Alternatively, peptide linkers may be used. Peptide linkers are amino acid sequences. The length, flexibility and hydrophilicity of the peptide linker are typically designed such that it does not to disturb the functions of the pore and the exonuclease. Preferred flexible peptide linkers are stretches of 2 to 20, such as 4, 6, 8, 10 or 16, serine and/or glycine amino acids. More preferred flexible linkers include $(SG)_1$, $(SG)_2$, $(SG)_3$, $(SG)_4$, $(SG)_5$ and $(SG)_8$ wherein S is serine and G is glycine. Preferred rigid linkers are stretches of 2 to 30, such as 4, 6, 8, 16 or 24, proline amino acids. More preferred rigid linkers include $(P)_{12}$ wherein P is proline.

The detector may comprise a transmembrane protein pore chemically modified with a molecular adaptor and an exonuclease. Such detectors are useful for Exonuclease Sequencing.

For Exonuclease Sequencing, the most preferred detector comprises (a) a pore derived from α-HL, (b) an exonuclease covalently attached to the pore and (c) a cyclodextrin or a derivative thereof. In this preferred embodiment, the pore preferably comprises one subunit shown in SEQ ID NO: 36 (i.e. α-HL-E287C-QC-D5FLAGH6) and six subunits shown in SEQ ID NO: 34 (i.e. α-HL-Q). The exonuclease is preferably exonuclease I from *E. coli* (SEQ ID NO: 8) or a variant thereof. The derivative of cyclodextrin is preferably heptakis-6-amino-β-cyclodextrin (am₇-βCD), 6-monodeoxy-6-monoamino-β-cyclodextrin (am₁-βCD) or heptakis-(6-deoxy-6-guanidino)-cyclodextrin (gu₇-βCD).

For Strand Sequencing, a preferred detector comprises (a) a pore derived from Msp and (b) a Phi29 polymerase. The pore and polymerase are not attached together. This preferred embodiment is discussed in more detail below.

The detector may be present as an individual or single detector. Alternatively, the detector may be present in a homologous or heterologous population of two or more detectors.

Polynucleotide

A polynucleotide, such as a nucleic acid, is a macromolecule comprising two or more nucleotides. The polynucleotide or nucleic acid bound by the protein may comprise any combination of any nucleotides. The nucleotides can be naturally occurring or artificial. The nucleotide can be oxidised or methylated. One or more nucleotides in the polynucleotide may be damaged. For instance, the polynucleotide may comprise a pyrimidine dimer. Such dimers are typically associated with damage by ultraviolet light and are the primary cause of skin melanomas.

A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The nucleotides are preferably selected from AMP, TMP, GMP, CMP, UMP, dAMP, dTMP, dGMP or dCMP.

A nucleotide may contain a sugar and at least one phosphate group (i.e. lack a nucleobase).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably double stranded. A single stranded polynucleotide may have one or more primers hybridised thereto and hence comprise one or more short regions of double stranded polynucleotide. The primers may be the same type of polynucleotide as the target polynucleotide or may be a different type of polynucleotide.

The polynucleotide can be a nucleic acid, such as deoxyribonucleic acid (DNA) or ribonucleic acid (RNA). The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The polynucleotide bound by the protein is preferably single stranded, such as cDNA, RNA, GNA, TNA or LNA. The polynucleotide bound by the protein is preferably double stranded, such as DNA. Proteins that bind single stranded polynucleotides may be used to sequence double stranded DNA as long as the double stranded DNA is dissociated into a single strand before it is bound by the protein.

If the Strand Sequencing method of the invention is used the polynucleotide analyte typically contains a portion that is double stranded even though generally only one strand is sequenced. In a primer/template setup, the template strand is typically sequenced (i.e. 5' threading into the pore). In any case, for Strand Sequencing, a double stranded polynucleotide preferably comprises a single stranded leader sequence. The leader sequence can be any length, but is typically 27 to 150 nucleotides in length, such as from 50 to 150 nucleotides in length. The addition of sections of single stranded polynucleotide to a double stranded polynucleotide can be performed in various ways. A chemical or enzymatic ligation can be done. In addition, the Nextera method by Epicentre is suitable. The inventors have developed a PCR method using a sense primer that, as usual contains a complementary section to the start of the target region of genomic DNA, but was additionally preceded with a 50 polyT section. To prevent the polymerase from extending the complementary strand opposite the polyT section and thereby create a blunt ended PCR product (as is normal), four abasic sites were added between the polyT section and the complementary priming section. These abasic sites will prevent the polymerase from extending beyond this region and so the polyT section will remain as 5' single stranded DNA on each of the amplified copies.

Nanopore Sensing

If the detector comprises a pore, the method of the invention preferably further comprises allowing the analyte to interact with the detector and measuring the current passing through the pore during the interaction and thereby determining the presence or absence or characteristics of the analyte. The analyte is present if the current flows through the pore in a manner specific for the analyte (i.e. if a distinctive current associated with the analyte is detected flowing through the pore). The analyte is absent if the current does not flow through the pore in a manner specific for the analyte. Similarly, the characteristics of the analyte can be determined using the current flowing through the pore during the interaction.

The invention therefore involves nanopore sensing of an analyte. The invention can be used to differentiate analytes of similar structure on the basis of the different effects they have on the current passing through the pore. The invention can also be used to measure the concentration of a particular analyte in a sample.

The invention may also be used in a sensor that uses many or thousands of pores in bulk sensing applications.

The method may be carried out using any suitable membrane (such as an amphiphilic layer or a lipid bilayer) system in which a pore is inserted into a membrane. The method is typically carried out using (i) an artificial membrane (such as an amphiphilic layer or a lipid bilayer) comprising a pore, (ii) an isolated, naturally-occurring lipid bilayer comprising a pore, or (iii) a cell having a pore inserted therein. The method is preferably carried out using an artificial membrane (such as an amphiphilic layer or a lipid bilayer). The membrane may comprise other transmembrane and/or intramembrane proteins as well as other molecules in addition to the pore. Suitable apparatus and conditions are discussed below with reference to the sequencing embodiments of the invention. The method of the invention is typically carried out vitro.

During the interaction between the analyte and the pore, the analyte affects the current flowing through the pore in a manner specific for that analyte. For example, a particular analyte will reduce the current flowing through the pore for a particular mean time period and to a particular extent. In other words, the current flowing through the pore is distinctive for a particular analyte. Control experiments may be carried out to determine the effect a particular analyte has on the current flowing through the pore. Results from carrying out the method of the invention on a test sample can then be compared with those derived from such a control experiment in order to identify a particular analyte in the sample, determine whether a particular analyte is present in the sample or determine the characteristics of the analyte. The frequency at which the current flowing through the pore is affected in a manner indicative of a particular analyte can be used to determine the concentration of that analyte in the sample.

Methods of Sequencing Polynucleotides

The present invention also provides methods of estimating the sequence of an analyte that is a target polynucleotide. The present invention also provides methods of sequencing an analyte that is a target polynucleotide. A polynucleotide is a macromolecule comprising two or more nucleotides. The nucleotides may be any of those discussed above, including methylated, oxidised and damaged nucleotides. The polynucleotide may be any of those discussed above and is preferably a nucleic acid.

These methods are possible because transmembrane protein pores can be used to differentiate nucleotides of similar structure on the basis of the different effects they have on the current passing through the pore. Individual nucleotides can be identified at the single molecule level from their current amplitude when they interact with the pore. The nucleotide is present in the pore (either individually or as part of a polynucleotide) if the current flows through the pore in a manner specific for the nucleotide (i.e. if a distinctive current associated with the nucleotide is detected flowing through the pore). Successive identification of the nucleotides in a target polynucleotide allows the sequence of the polynucleotide to be determined.

In one embodiment, the method comprises (a) coupling the target polynucleotide to a membrane; (b) allowing the target polynucleotide to interact with a detector present in the membrane, wherein the detector comprises a transmembrane pore and an exonuclease, such that the exonuclease digests an individual nucleotide from one end of the target polynucleotide; (c) allowing the nucleotide to interact with the pore; (d) measuring the current passing through the pore during the interaction and thereby determining the identity of the nucleotide; and (e) repeating steps (b) to (d) at the same end of the target polynucleotide and thereby determining the sequence of the target polynucleotide. In another embodiment, the method comprises (a) coupling the target polynucleotide to a membrane; (b) allowing the target polynucleotide to interact with a detector present in the membrane, wherein the detector comprises a transmembrane protein pore, a molecular adaptor that facilitates an interaction between the pore and one or more nucleotides and an exonuclease, such that the exonuclease digests an individual nucleotide from one end of the target polynucleotide; (c) allowing the nucleotide to interact with the adaptor; (d) measuring the current passing through the pore during the interaction and thereby determining the identity of the nucleotide; and (e) repeating steps (b) to (d) at the same end of the target polynucleotide and thereby determining the sequence of the target polynucleotide. Hence, the method involves nanopore sensing of a proportion of the nucleotides in a target polynucleotide in a successive manner in order to sequence the target polynucleotide. Individual nucleotides are described above and below. This is Exonuclease Sequencing.

In another embodiment, the method comprises: (a) coupling the target polynucleotide to a membrane; (b) allowing the target polynucleotide to interact with a detector present in the membrane, wherein the detector comprises a transmembrane pore, such that the target polynucleotide moves through the pore; and (c) measuring the current passing through the pore as the target polynucleotide moves with respect to the pore and thereby determining the sequence of the target polynucleotide. In another embodiment, the method comprises (a) coupling the target polynucleotide to a membrane; (b) allowing the target polynucleotide to interact with a detector present in the membrane, wherein the detector comprises a transmembrane protein pore and a polynucleotide binding protein, preferably a polymerase, such that the protein controls the movement of the target polynucleotide through the pore and a proportion of the nucleotides in the target polynucleotide interacts with the pore; and (c) measuring the current passing through the pore during each interaction and thereby determining the sequence of the target polynucleotide. Hence, the method involves nanopore sensing of a proportion of the nucleotides in a target polynucleotide as the nucleotides individually pass through the barrel or channel in order to sequence the target polynucleotide. This is Strand Sequencing.

These methods of the invention are particularly suited for sequencing target polynucleotides, such as nucleic acids, because the coupling of the nucleic acid sequences to the membrane lowers by several orders of magnitude the amount of polynucleotide required. The concentrations at which target polynucleotides can be sequenced using the invention are discussed above.

The whole or only part of the target polynucleotide may be sequenced using this method. The polynucleotide can be any length. For example, the polynucleotide can be at least 10, at least 50, at least 100, at least 150, at least 200, at least 250, at least 300, at least 400 or at least 500 nucleotides in length. The polynucleotide can be 1000 or more nucleotides or 5000 or more nucleotides in length. The polynucleotide can be naturally occurring or artificial. For instance, the method may be used to verify the sequence of a manufactured oligonucleotide. The methods are typically carried out in vitro.

The nucleotides (either digested from the target polynucleotide or present in the polynucleotide) may interact with the pore on either side of the membrane. The nucleotides may interact with the pore in any manner and at any site. As discussed above, the nucleotides preferably reversibly bind to the pore via or in conjunction with the adaptor. The nucleotides most preferably reversibly bind to the pore via or in conjunction with the adaptor as they pass through the pore across the membrane. The nucleotides can also reversibly bind to the barrel or channel of the pore via or in conjunction with the adaptor as they pass through the pore across the membrane.

During the interaction between a nucleotide and the pore, the nucleotide affects the current flowing through the pore in a manner specific for that nucleotide. For example, a particular nucleotide will reduce the current flowing through the pore for a particular mean time period and to a particular extent. In other words, the current flowing through the pore is distinctive for a particular nucleotide. Control experiments may be carried out to determine the effect a particular nucleotide has on the current flowing through the pore. Results from carrying out the method of the invention on a test sample can then be compared with those derived from such a control experiment in order to determine the sequence of the target polynucleotide.

The sequencing methods may be carried out using any suitable membrane/pore system in which a pore is present in or inserted into a membrane. The methods are typically carried out using a membrane comprising naturally-occurring or synthetic lipids. The membrane is typically formed in vitro. The methods are preferably not carried out using an isolated, naturally occurring membrane comprising a pore, or a cell expressing a pore. The methods are preferably carried out using an artificial membrane. The membrane may comprise other transmembrane and/or intramembrane proteins as well as other molecules in addition to the pore.

The membrane forms a barrier to the flow of ions, nucleotides and polynucleotides. The membrane is preferably an amphiphilic layer such as a lipid bilayer. Lipid bilayers suitable for use in accordance with the invention are described above.

The sequencing methods of the invention are typically carried out in vitro.

The sequencing methods may be carried out using any apparatus that is suitable for investigating a membrane/pore system in which a pore is present in or inserted into a membrane. The method may be carried out using any apparatus that is suitable for nanopore sensing. For example, the apparatus comprises a chamber comprising an aqueous solution and a barrier that separates the chamber into two sections. The barrier has an aperture in which the membrane containing the pore is formed. The analyte may be coupled to the membrane in either of the two sections of the chamber.

The sequencing methods may be carried out using the apparatus described in International Application No. PCT/GB08/000562.

The methods of the invention involve measuring the current passing through the pore during interaction with the nucleotide or as the target polynucleotide moves with respect to the pore. Therefore the apparatus also comprises an electrical circuit capable of applying a potential and measuring an electrical signal across the membrane and pore. The methods may be carried out using a patch clamp or a voltage clamp. The methods preferably involve the use of a voltage clamp.

The sequencing methods of the invention involve the measuring of a current passing through the pore during interaction with the nucleotide or as the target polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 160 mV to 240 mV. It is possible to increase discrimination between different nucleotides by a pore by using an increased applied potential.

The sequencing methods are typically carried out in the presence of any alkali metal chloride salt. In the exemplary apparatus discussed above, the salt is present in the aqueous solution in the chamber. Potassium chloride. (KCl), sodium chloride (NaCl) or caesium chloride (CsCl) is typically used. KCl is preferred. The salt concentration is typically from 0.1 to 2.5M, from 0.3 to 1.9M, from 0.5 to 1.8M, from 0.7 to 1.7M, from 0.9 to 1.6M or from 1M to 1.4M. The salt concentration is preferably from 150 mM to 1M. High salt concentrations provide a high signal to noise ratio and allow for currents indicative of the presence of a nucleotide to be identified against the background of normal current fluctuations. Lower salt concentrations may be used if nucleotide detection is carried out in the presence of an enzyme, such as when sequencing polynucleotides. This is discussed in more detail below.

The methods are typically carried out in the presence of a buffer. In the exemplary apparatus discussed above, the buffer is present in the aqueous solution in the chamber. Any buffer may be used in the method of the invention. One suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods are typically carried out at from 0° C. to 100° C. from 15° C. to 95° C., from 16° C. to 90° C., from 17° C. to 85° C., from 18° C. to 80° C., 19° C. to 70° C., or from 20° C. to 60° C. The methods may be carried out at room temperature. The methods are preferably carried out at a temperature that supports enzyme function, such as about 37° C.

As mentioned above, good nucleotide discrimination can be achieved at low salt concentrations if the temperature is increased. In addition to increasing the solution temperature, there are a number of other strategies that can be employed to increase the conductance of the solution, while maintaining conditions that are suitable for enzyme activity. One such strategy is to use the lipid bilayer to divide two different concentrations of salt solution, a low salt concentration of salt on the enzyme side and a higher concentration on the opposite side. One example of this approach is to use 200 mM of KCl on the cis side of the membrane and 500 mM KCl in the trans chamber. At these conditions, the conductance through the pore is expected to be roughly equivalent to 400 mM KCl under normal conditions, and the enzyme only experiences 200 mM if placed on the cis side. Another possible benefit of using asymmetric salt conditions is the osmotic gradient induced across the pore. This net flow of water could be used to pull nucleotides into the pore for detection. A similar effect can be achieved using a neutral osmolyte, such as sucrose, glycerol or PEG. Another possibility is to use a solution with relatively low levels of KCl and rely on an additional charge carrying species that is less disruptive to enzyme activity.

The target polynucleotide being analysed can be combined with known protecting chemistries to protect the polynucleotide from being acted upon by the binding protein or exonuclease while in the bulk solution. The pore can then be used to remove the protecting chemistry. This can be achieved either by using protecting groups that are unhybridised by the pore, binding protein or enzyme under an applied potential (WO 2008/124107) or by using protecting chemistries that are removed by the binding protein or enzyme when held in close proximity to the pore (J Am Chem Soc. 2010 Dec. 22; 132(50):17961-72).

Exonuclease Sequencing

In one embodiment, the method of sequencing an analyte which is a target polynucleotide involves allowing the target polynucleotide to interact with an exonuclease enzyme. Any of the exonuclease enzymes discussed above may be used in the method. The exonuclease releases individual nucleotides from one end of the target polynucleotide. The enzyme may be covalently attached to the pore as discussed above.

An individual nucleotide is a single nucleotide. An individual nucleotide is one which is not bound to another nucleotide or polynucleotide by a nucleotide bond. A nucleotide bond involves one of the phosphate groups of a nucleotide being bound to the sugar group of another nucleotide.

An individual nucleotide is typically one which is not bound by a nucleotide bond to another polynucleotide of at least 5, at least 10, at least 20, at least 50, at least 100, at least 200, at least 500, at least 1000 or at least 5000 nucleotides. For example, the individual nucleotide has been digested from a target polynucleotide, such as a DNA or RNA strand. The individual nucleotide may be any of those discussed above.

Exonucleases are enzymes that typically latch onto one end of a polynucleotide and digest the polynucleotide one nucleotide at a time from that end. The exonuclease can digest the polynucleotide in the 5' to 3' direction or 3' to 5' direction. The end of the polynucleotide to which the exonuclease binds is typically determined through the choice of enzyme used and/or using methods known in the art. Hydroxyl groups or cap structures at either end of the polynucleotide may typically be used to prevent or facilitate the binding of the exonuclease to a particular end of the polynucleotide.

The method involves allowing the polynucleotide to interact with the exonuclease so that the nucleotides are digested from the end of the polynucleotide at a rate that allows identification of a proportion of nucleotides as discussed above. Methods for doing this are well known in the art. For example, Edman degradation is used to successively digest single amino acids from the end of polypeptide such that they may be identified using High Performance Liquid Chromatography (HPLC). A homologous method may be used in the present invention.

The rate at which the exonuclease functions is typically slower than the optimal rate of a wild-type exonuclease. A suitable rate of activity of the exonuclease in the method of sequencing involves digestion of from 0.5 to 1000 nucleotides per second, from 0.6 to 500 nucleotides per second, 03 to 200 nucleotides per second, from 0.8 to 100 nucleotides per second, from 0.9 to 50 nucleotides per second or 1 to 20 or 10 nucleotides per second. The rate is preferably 1, 10, 100, 500 or 1000 nucleotides per second. A suitable rate of exonuclease activity can be achieved in various ways. For example, variant exonucleases with a reduced optimal rate of activity may be used in accordance with the invention.

The Exonuclease Sequencing methods of the invention have additional advantages beyond the reduction in the amount of polynucleotide needed. The inventors have studied the presentation of single stranded DNA in solution to an Exonuclease-Nanopore ("X-Pore")/membrane system under potential. When DNA analyte is introduced into the system, the pore may become blocked permanently or temporarily, preventing the detection of individual nucleotides. When one end of the DNA analyte is localised away from the pore, for example by coupling to the membrane, surprisingly it was found that this blocking is no longer observed. It also increases the number of potential DNA threading events for the enzyme due to the increased effective concentration of being in the same plane as the analyte. This acts to lower the binding time between analytes and increase sequencing throughput.

Strand Sequencing

Strand Sequencing involves the controlled and stepwise translocation of polynucleotides through a pore. A polynucleotide is a macromolecule comprising two or more nucleotides. The polynucleotide bound by the protein may comprise any combination of any nucleotides. The nucleotides may be any of those discussed above.

The Strand Sequencing method of the invention typically uses a polynucleotide binding protein to control the movement of the target polynucleotide through the pore. Examples of such proteins are given above. The polynucleotide binding protein is preferably a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the target polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases, translocases and topoisomerases, such as gyrases. Suitable enzymes include, but are not limited to, exonuclease I from *E. coli* (SEQ ID NO: 8), exonuclease III enzyme from *E. coli* (SEQ ID NO: 10), RecJ from *T. thermophilus* (SEQ ID NO: 12) and bacteriophage lambda exonuclease (SEQ ID NO: 14) and variants thereof. Three subunits comprising the sequence shown in SEQ ID NO: 14 or a variant thereof interact to form a trimer exonuclease. The enzyme is most preferably derived from Phi29 DNA polymerase. An enzyme derived from Phi29 polymerase comprises the sequence shown in SEQ ID NO: 6 or a variant thereof.

According to one embodiment the polynucleotide binding protein is coupled or tethered to the membrane and is able both to bind to analyte polynucleotide and then to control translocation of the analyte through the pore. In this embodiment, the analyte polynucleotide may be coupled to the membrane via the polynucleotide binding protein. The analyte polynucleotide and the polynucleotide binding protein may both be coupled to the membrane, preferably by different coupling methods. The polynucleotide binding protein is preferably a helicase.

A variant of SEQ ID NOs: 6, 8, 10, 12 or 14 is an enzyme that has an amino acid sequence which varies from that of SEQ ID NO: 6, 8, 10, 12 or 14 and which retains polynucleotide binding ability. The variant may include modifications that facilitate binding of the polynucleotide and/or facilitate its activity at high salt concentrations and/or room temperature.

Over the entire length of the amino acid sequence of SEQ ID NO: 6, 8, 10, 12 or 14, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 6, 8, 10, 12 or 14 over the entire sequence. There may be at least 80%, for example at least 85%, 90% or 95%, amino acid identity over a stretch of 200 or more, for example 230, 250, 270 or 280 or more, contiguous amino acids ("hard homology"). Homology is determined as described above. The variant may differ from the wild-type sequence in any of the ways discussed above with reference to SEQ ID NO: 2. The enzyme may be covalently attached to the pore as discussed above.

The enzyme is not required to be in as close a proximity to the pore lumen as for individual nucleotide sequencing as there is no potential for disorder in the series in which nucleotides reach the sensing moiety of the pore.

The two strategies for strand DNA sequencing are the translocation of the DNA through the nanopore, both cis to trans and trans to cis, either with or against an applied potential. One of the most advantageous mechanisms for strand sequencing is the controlled translocation of single strand DNA through the nanopore under an applied potential. Exonucleases that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential. Alternatively, the single strand DNA dependent polymerases can act as molecular brake slowing down the movement of a polynucleotide through the pore.

In the most preferred embodiment, Strand Sequencing is carried out using a pore derived from Msp and a Phi29 DNA polymerase. The method may comprise (a) coupling the target polynucleotide to a membrane; (b) allowing the target polynucleotide to interact with a detector in the membrane, which detector comprises a pore derived from Msp and a Phi29 DNA polymerase, such that the polymerase controls the movement of the target polynucleotide through the pore; and (c) measuring the current passing through the pore as the target polynucleotide moves with respect to the pore and thereby determining the sequence of the target polynucleotide, wherein steps (b) and (c) are carried out with a voltage applied across the pore. The method may comprise (a) coupling the target polynucleotide to a membrane; (b) allowing the target polynucleotide to interact with a detector in the membrane, which detector comprises a pore derived from Msp and a Phi29 DNA polymerase, such that the polymerase controls the movement of the target polynucleotide through the pore and a proportion of the nucleotides in the target polynucleotide interacts with the pore; and (c) measuring the current passing through the pore during each interaction and thereby determining the sequence of the target polynucleotide, wherein steps (b) and (c) are carried out with a voltage applied across the pore. When the target polynucleotide is contacted with a Phi29 DNA polymerase and a pore derived from Msp, the target polynucleotide firstly forms a complex with the Phi29 DNA polymerase. When the voltage is applied across the pore, the target polynucleotide/Phi29 DNA polymerase complex forms a complex with the pore and controls the movement of the target polynucleotide through the pore.

These Msp/Phi29 embodiments have three unexpected advantages. First, the target polynucleotide moves through the pore at a rate that is commercially viable yet allows effective sequencing. The target polynucleotide moves through the Msp pore more quickly than it does through a hemolysin pore. Second, an increased current range is observed as the polynucleotide moves through the pore allowing the sequence to be determined more easily. Third, a decreased current variance is observed when the specific pore and polymerase are used together thereby increasing the signal-to-noise ratio.

Any polynucleotide described above may be sequenced. At least a portion of the polynucleotide is preferably double stranded.

The pore may be any of the pores discussed above. The pore may comprise eight monomers comprising the sequence shown in SEQ ID NO: 2 or a variant thereof.

Wild-type Phi29 DNA polymerase has polymerase and exonuclease activity. It may also unzip double stranded polynucleotides under the correct conditions. Hence, the enzyme, may work in three modes. This is discussed in more detail below.

The Phi29 DNA polymerase may comprise the sequence shown in SEQ ID NO: 6 or a variant thereof. A variant of SEQ ID NOs: 6 is an enzyme that has an amino acid sequence which varies from that of SEQ ID NO: 6 and which retains polynucleotide binding activity. The variant must work in at least one of the three modes discussed below. Preferably, the variant works in all three modes. The variant may include modifications that facilitate handling of the polynucleotide and/or facilitate its activity at high salt concentrations and/or room temperature.

Over the entire length of the amino acid sequence of SEQ ID NO: 6, a variant will preferably be at least 40% homologous to that sequence based on amino acid identity. More preferably, the variant polypeptide may be at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology is determined as described above. The variant may differ from the wild-type sequence in any of the ways discussed above with reference to SEQ ID NO: 2. The enzyme may be covalently attached to the pore as discussed above.

Any of the systems, apparatus or conditions discussed above may be used in accordance with this preferred embodiment. The salt concentration is typically from 0.15M to 0.6M. The salt is preferably KCl.

The method may be carried out in one of three preferred ways based on the three modes of the Phi29 DNA polymerase. Each way includes a method of proof-reading the sequence. First, the method is preferably carried out using the Phi29 DNA polymerase as a polymerase. In this embodiment, steps (b) and (c) are carried out in the presence of free nucleotides and an enzyme cofactor such that the polymerase moves the target polynucleotide through the pore against the field resulting from the applied voltage. The target polynucleotide moves in the 5' to 3' direction. The free nucleotides may be one or more of any of the individual nucleotides discussed above. The enzyme cofactor is a factor that allows the Phi29 DNA polymerase to function either as a polymerase or an exonuclease. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$. The method preferably further comprises (d) removing the free nucleotides such that the polymerase moves the target polynucleotide through the pore with the field resulting from the applied voltage (i.e. in the 3' and 5' direction) and a proportion of the nucleotides in the target polynucleotide interacts with the pore and (e) measuring the current passing through the pore during each interaction and thereby proof reading the sequence of the target polynucleotide obtained in step (c), wherein steps (d) and (e) are also carried out with a voltage applied across the pore.

Second, the method is preferably carried out using the Phi29 DNA polymerase as an exonuclease. In this embodiment, wherein steps (b) and (c) are carried out in the absence of free nucleotides and the presence of an enzyme cofactor such that the polymerase moves the target polynucleotide through the pore with the field resulting from the applied voltage. The target polynucleotide moves in the 3' to 5' direction. The method preferably further comprises (d) adding free nucleotides such that the polymerase moves the target polynucleotide through the pore against the field resulting from the applied voltage (i.e. in the 5' to 3' direction) and a proportion of the nucleotides in the target polynucleotide interacts with the pore and (e) measuring the current passing through the pore during each interaction and thereby proof reading the sequence of the target polynucleotide obtained in step (c), wherein steps (d) and (e) are also carried out with a voltage applied across the pore.

Third, the method is preferably carried out using the Phi29 DNA polymerase in unzipping mode. In this embodiment, steps (b) and (c) are carried out in the absence of free nucleotides and the absence of an enzyme cofactor such that the polymerase controls the movement of the target polynucleotide through the pore with the field resulting from the applied voltage (as it is unzipped). In this embodiment, the polymerase acts like a brake preventing the target polynucleotide from moving through the pore too quickly under the influence of the applied voltage. The method preferably further comprises (d) lowering the voltage applied across the pore such that the target polynucleotide moves through the pore in the opposite direction to that in steps (b) and (c) (i.e. as it re-anneals) and a proportion of the nucleotides in the target polynucleotide interacts with the pore and (e) measuring the current passing through the pore during each interaction and thereby proof reading the sequence of the target polynucleotide obtained in step (c), wherein steps (d) and (e) are also carried out with a voltage applied across the pore.

Kits

The present invention also provides kits for sequencing an analyte which is a target polynucleotide. The kit comprises (a) a transmembrane pore, such as a transmembrane protein pore, (h) a polynucleotide binding protein and (c) means to couple the target polynucleotide to a membrane. In a preferred embodiment, the polynucleotide binding protein is an exonuclease and the kit further comprises a molecular adaptor that facilitates an interaction between the pore and one or more nucleotides in the target polynucleotide. Such a kit may be used for Exonuclease Sequencing. In another preferred embodiment, the kit comprises the components of a membrane, such as the phospholipids needed to form a lipid bilayer.

The means to couple the target polynucleotide to a membrane preferably comprises a reactive group. Suitable groups include, but are not limited to, thiol, cholesterol, lipid and biotin groups. Any of the embodiments discussed above with reference to the methods of the invention are equally applicable to the kits of the invention.

The kits of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

Apparatus

The invention also provides an apparatus for sequencing an analyte which is a target polynucleotide. The apparatus comprises (a) a membrane, (h) a plurality of transmembrane pores in the membrane, (c) a plurality of polynucleotide binding proteins and (d) a plurality of target polynucleotides coupled to the membrane. The plurality of polynucleotide binding proteins may be in the membrane. The apparatus may be any conventional apparatus for analyte analysis, such as an array or a chip. In a preferred embodiment, the polynucleotide binding protein is an exonuclease and the apparatus comprises a molecular adaptor that facilitates an interaction between the pore and one or more nucleotides in the target polynucleotide. Such an apparatus may be used for Exonuclease Sequencing. Any of the embodiments discussed above with reference to the methods of the invention are equally applicable to the kits of the invention. The apparatus preferably comprises:

a sensor device that is capable of supporting the membrane and plurality of pores and being operable to perform polynucleotide sequencing using the pores and proteins; and at least one reservoir far holding material for performing the sequencing.

The apparatus preferably comprises:

a sensor device that is capable of supporting the membrane and plurality of pores and being operable to perform polynucleotide sequencing using the pores and proteins;

at least one reservoir for holding material for performing the sequencing;

a fluidics system configured to controllably supply material from the at least one reservoir to the sensor device; and one or more, such as a plurality, of containers for receiving respective samples, the fluidics system being configured to supply the samples selectively from the one or more containers to the sensor device. The apparatus may be any of those described in International Application No. PCT/GB08/004127 (published as WO 2009/077734), PCT/GB10/000789 (published as WO 2010/122293), International Application No. PCT/GB10/002206 (not yet published) or International Application No. PCT/US99/25679 (published as WO 00/28312).

The following Examples illustrate the invention:

Example 1

Exonuclease Sequencing 1.1 Materials and Methods
1.1.1 Materials and Oligonucleotides Oligonucleotides were purchased from either ADTBio or IDTDNA. Details of the exact sequences and modifications can be found in the Table below (SEQ ID NOs 18 to 21).

| Name | Modification 5' | Internal | 3' | Length (nt) | Sequence | SEQ ID NO: | Supplier Code |
|------|-----------------|----------|-----|-------------|----------|------------|---------------|
| ONLA 0692 | Chol-TEG | — | — | 70 | TTTTTTTTTTTTTTTTTTTTTTTTTTTTTT TTTTTTTTTTTTTTTTTTTTTTTTTTTTTT TTTTTT | 18 | ATDBio A8691 |
| ONLA 0692 | Chol-TEG | — | — | 70 | AAAAAAAAAAAAAAAAAAAAAAAAAAAAAA AAAAAAAAAAAAAAAAAAAAAAAAAAAAAA AAAAAAAAAAAA | 19 | ATDBio A887 |
| ONLA 0683 | Chol-TEG | — | — | 70 | CCCCCCCCCCCCCCCCCCCCCCCCCCCCCC CCCCCCCCCCCCCCCCCCCCCCCCCCCCCC CCCCCCCCCCCCCC | 20 | ATDBio A8874 |
| ONLA 0693 | Strep-Btn: ssDNA | — | — | 70 | TTTTTTTTTTTTTTTTTTTTTTTTTTTTTT TTTTTTTTTTTTTTTTTTTTTTTTTTTTTT TTTTTT | 18 | IDT 60739014 |
| ONLA 0694 | Strep-Btn: ssDNA | — | — | 70 | TGTGTTCTATGTCTTATTCTTACTTCGTTA TTCTTGTCTCTATTCTGTTTATGTTTCTTG TTTGTTAGCA | 21 | IDT 60739013 |
| ONLA 0706 | — | — | — | 70 | TTTTTTTTTTTTTTTTTTTTTTTTTTTTTT TTTTTTTTTTTTTTTTTTTTTTTTTTTTTT TTTTTT | 18 | IDT 60692267 |

Recombinant Streptavidin, expressed in *E. coli*, was purchased from Sigma Aldrich (S0677). The synthetic lipids 1,2-diphytanoyl-sn-glycero-3-phosphocholine (16:0 4ME PC) and 1,2-dipalmitoyl-sn-glycero-3-phosphoethanolamine-N-cap biotinyl (16:0 Cap Biotinyl PE) were purchased from Avanti Polar Lipids.

1.1.2 HPLC Purification of Mono-Substituted Streptavidin.

1 uM of 5'-biotin modified DNA was mixed with 10 uM of streptavidin in 25 mM Tris.HCl, 400 mM KCl, 10 mM MgCl2, pH 7.5 and incubated for 30 mins at 22° C. Mono-substituted Strep:DNA conjugates were separated using an Agilent 1200 analytical LC system comprising a binary pump, column oven maintained at 23° C., UV detector with 13 ul flow cell, with both sample compartment and fractions maintained at 4° C. The column was an Agilent BioMonolith QA run at 1 ml min$^{-1}$, and samples were separated on a gradient from 30 mM-1.1 M NaCl in 100 mM Tris pH 8.5. Quantification of purified mono-substituted Strep:DNA conjugates was carried out using densitometry following gel electrophoresis using a series of DNA standards to create a standard curve.

1.1.3 Single Channel Recordings from Planar Lipid Bilayers

Bilayers were formed by apposition of two monolayers of either 100% 16:0 4ME PC or 95% 16:0 4ME PC, 5% 16:0 Cap Biotinyl PE. Bilayers were formed across a 60-150 μm diameter aperture in Teflon film (25 μm thickness from Goodfellow, Malvern, PA), which divided a chamber into two buffer compartments (cis and trans) each with a volume of 1 ml. Bilayers were formed across the aperture by consecutively raising the buffer level in each compartment until a high resistance seal was observed (≥10 GΩ). Unless otherwise stated, DNA and protein were added to the cis compartment, which was connected to ground. No reagents were added to the trans compartment, which was connected to the head-stage of the amplifier. Unless stated otherwise, experiments were carried out in 25 mM Tris.HCl, 400 mM KCl, 10 mM MgCl2, pH 7.5, at 22° C.

1.2 Results 1.2.1 Single Molecule Detection of Tethered Analytes

Figure 2:
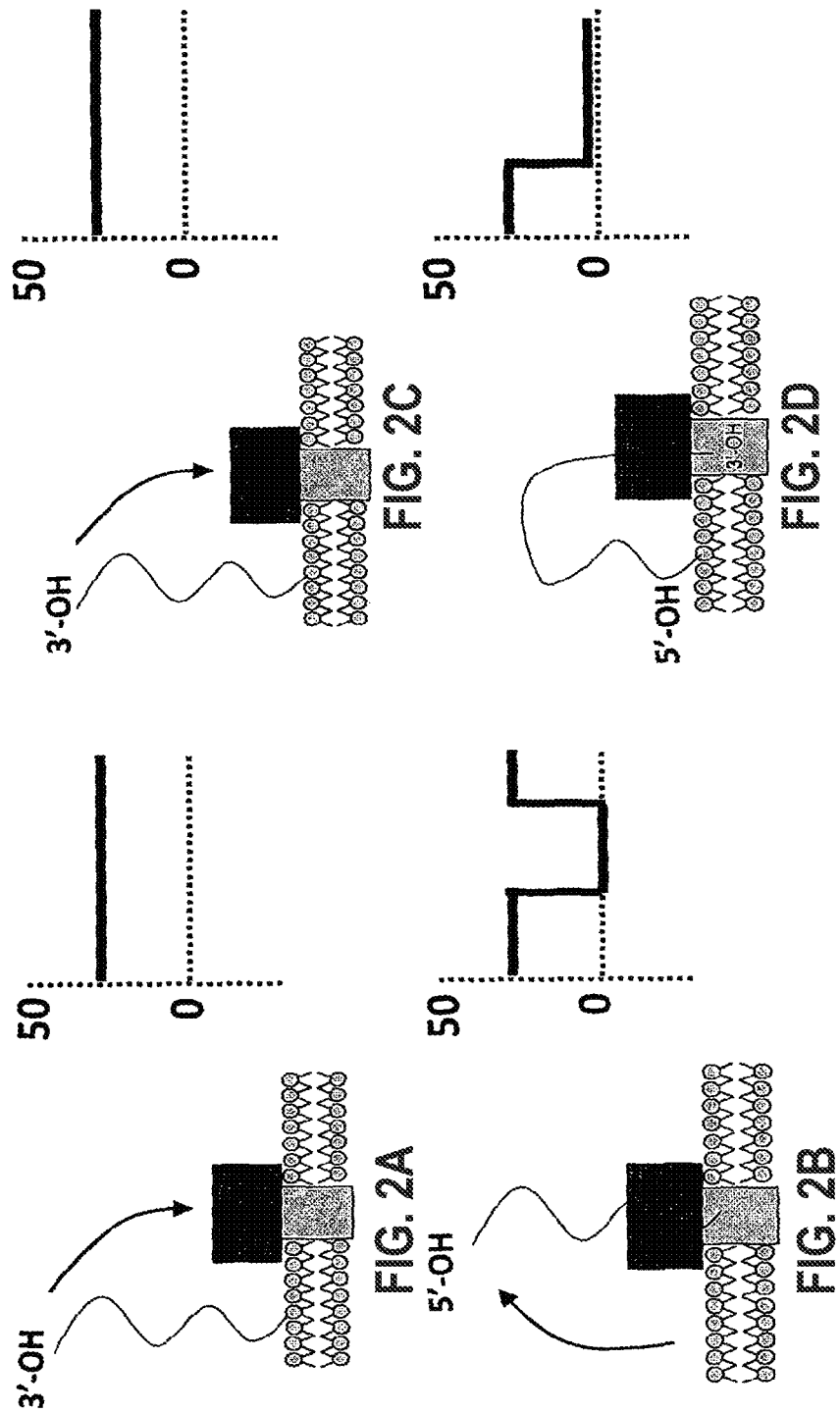
FIGS. 2A-2D show a method for tethering DNA nanopore interactions.

Nanopore detection rates for single stranded DNA free in solution can be determined by measuring the number of DNA translocations (events) through the nanopore per second. A DNA translocation can be identified by a signature transient current blockade in the digital recording. For tethered analytes the number of interactions can similarly be calculated provided the DNA is only transiently tethered to the bilayer, such as via a cholesterol group. As the free end of the DNA enters the nanopore it will reside in the barrel until the tethered end becomes free of the bilayer and so the molecule can translocate (FIGS. 2A and 2B). If the tethering is more stable then the block will be permanent (FIGS. 2C and 2D).

A 50% mix of cholesterol modified PolyA and PolyC (ONLA0682 and ONLA0683 respectively) were assayed at 10, 100 and 1000 pM final concentration to establish the effect of Chol-DNA on the event rate and dwell time (Table below). This was compared to the event rate for free single stranded DNA.

| | Free Analyte | Tethered Analyte | | |
|---|---|---|---|---|
| | 100 nM | 10 pM | 100 pM | 1000 pM |
| Event Rate s$^{-1}$ 120 mV | 0.01 | 0.015 | 0.045 | 2.5 |
| 160 mV | 0.74 | 0.15 | 1.05 | 26 |

Rates increase with voltage at all concentrations (Table above) and of course event rates are higher at higher concentrations. At the lower concentrations and voltages the event rates are too low to really be considered meaningful. That is, it is likely that most, if not all, of the events at those conditions are just the occasional false-positive. It is somewhat surprising however that at higher current levels a significant number of DNA events are seen with only 10 pM of DNA. In spite of the DNA concentration being at least 100 times lower, the event rates are much higher with cholesterol modified DNA. It is somewhat surprising that at the higher current levels (≥160 mV) a significant number of DNA events are still seen with only 10 pM of DNA and these DNA events occur at a frequency similar to 100 nM of unmodified ssDNA. It can be estimated that tethering of the DNA improves the detection of the DNA analyte by 3-4 orders of magnitude. For certain applications the transient nature of the tethering might be preferred. If a stable tethering molecule were attached directly to either the 5' or 3'-end of the DNA then some sequence data will be lost as the sequencing run cannot continue to the end of the DNA, due to the distance between the bilayer and the enzymes active site. If the tethering is more transient then when the tethered end randomly becomes free of the bilayer then the enzyme can process the DNA to completion.

1.3 Conclusions

We have demonstrated here the potential to improve the detection efficiency of a nanopore detector for an analyte by approximately 3-4 orders of magnitude. The rapid pore blocking suggests that this tethered analyte is still available for proteins both from solution and in the bilayer (such as an enzyme or a nanopore construct respectively) and so has the potential as either a delivery mechanism to the pore itself or to a nanopore-enzyme construct.

Various means of analyte attachment to the lipid bilayer are available and most have been reported for the tethering of ssDNA, as functional chemistry can be easily incorporated during oligonucleotide synthesis. In the preferred means a ddNTP modified with a biotin can be incorporated to the 3'-end of ssDNA using terminal transferase. By mixing with streptavidin the analyte DNA can then be added to a single pore in a lipid bilayer containing 1-5% Biotin PE where it will become tethered. Alternatively if the sequence is known then the DNA can be hybridised to complementary synthetic DNA already modified at one end to be lipophilic.

Another advantage of tethering the analyte is that you have control over one end of the DNA. It can be seen above that DNA will rapidly block the pore if one end is held in close proximity, in the above case this is the bilayer. If a DNA handling enzyme, such as an exonuclease, is attached to the nanopore then it will bind one end of the DNA and again localise it to the pore and so the other end will rapidly block. If DNA is immobilised however then when the enzyme binds to one end then both are now occupied and unavailable for the pore.

The need for low analyte requirement DNA sequencing is for applications such as single cell sequencing for epigenetics and also screening from low volume biological samples. The current Illumina Genome analyser system requires 100 ng to 1 ug DNA for a sequencing library prep. A single 128 channel chip for nanopore sequencing could use ~0.5 ng DNA without the need for amplification; based on 1000 mer fragment generation and read length at 10 pM concentration.

2. Example 2

Strand Sequencing

In addition to the work for attaching ssDNA to the lipid membrane for Exonuclease Sequencing, the technique can also be adapted to a Strand Sequencing approach. In Strand Sequencing, a portion of a polynucleotide strand is threaded through the nanopore under an applied potential. The strand is typically DNA or RNA, for example single stranded or double stranded DNA. Preferably the strand is single stranded DNA (ssDNA). The base residues comprised in the strand interact with the nanopore and a signal is generated that is characteristic of each residue. The strand is moved through the pore, causing variation to the signal. The signal can be used to infer the sequence of the DNA strand.

One embodiment of Strand Sequencing uses a protein pore embedded in a lipid membrane. Electrodes are placed either side of the lipid membrane in an electrolyte and a potential is applied across the system. Under the potential the polynucleotide translocates the pore. The current through the protein pore can be measured and used to recognise bases as they pass through the trans-membrane barrel of the pore. Typically the protein pore will be a bacterial membrane protein, such as a porin or a toxin. Preferably the pore is a hemolysin, a gramicidin or an MspA.

The rate that DNA translocates through a pore may be too fast to allow accurate identification of each base, therefore it may be desirable to slow the translocation. One method for slowing the translocation of a DNA strand is to use a DNA handling protein, such as a DNA polymerase. The DNA handling protein may be attached to the pore, for example by covalent bonding, either directly or via linker groups. Typically the DNA handling protein is attached to the pore for exonuclease sequencing applications. Commonly for strand sequencing applications the DNA handling protein is not attached to the pore.

For a Strand Sequencing approach, it is desirable to have a DNA handling protein that has a very long binding time on top of the nanopore. A long binding time allows for many nucleotides to be processed through the DNA handling protein and thus through the nanopore. For a polymerase, a typical rate of processing may be around 20 nucleotides a second. A binding time of 10 minutes would allow the movement of 12,000 nucleotides. A binding time of one minute would allow 120 nucleotides to be processed.

Using this approach, a long binding time is also related to the read length. Currently, a read length of around 100 nucleotides would be sufficient to rival existing technologies, although longer read lengths are desirable, for example a read length of 200, 500 or 1000 nucleotides. Preferred read lengths are at least 5000 nucleotides, more preferably 10000 or 50000 nucleotides. One advantage of a long read length is that it greatly reduces the complexity of the bioinformatics needed to analyse sequencing information.

Typically a DNA handling protein is a DNA polymerase. Preferred DNA handling proteins include Phi29 DNA polymerase.

2.1 Materials and Methods

Bilayers were formed by apposition of two monolayers of either 100% DPhPC or 99% DPhPC, 1% 16:0 Cap Biotinyl PE. Bilayers were formed across a 60-150 µm diameter aperture in Teflon film (25 µm thickness from Goodfellow, Malvern, PA), which divided a chamber into two buffer compartments (cis and trans) each with a volume of 1 ml. Bilayers were formed across the aperture by consecutively raising the buffer level in each compartment until a high resistance seal was observed (≥10 GΩ). Unless otherwise stated, DNA and protein were added to the cis compartment, which was connected to ground. No reagents were added to the trans compartment, which was connected to the headstage of the amplifier. Experiments were carried out with 400 mM KCl, 25 mM Tris.HCl, 10 uM EDTA, pH 7.5. The hemolysin mutant used was HL-(E111N/K147N)7 (SEQ ID NO: 38).

1 uM of 5'-biotin modified DNA (StrandDNA1) was mixed with 10 uM of streptavidin in 25 mM Tris.HCl, 400 mM KCl, 10 mM MgCl2, pH 7.5 and incubated for 30 mins at 22° C. Mono-substituted Strep:DNA conjugates were separated using an Agilent 1200 analytical LC system comprising a binary pump, column oven maintained at 23° C., UV detector with 13 ul flow cell, with both sample compartment and fractions maintained at 4° C. The column was an Agilent BioMonolith QA run at 1 ml min-1, and samples were separated on a gradient from 30 mM-1.1 M NaCl in 100 mM Tris pH 8.5. Quantification of purified mono-substituted Strep:DNA conjugates was carried out using densitometry following gel electrophoresis using a series of DNA standards to create a standard curve. To form StrandDNA3, the DNA-streptavidin complex was hybrisided with a 5× excess of StrandDNA2 by heating to 50° C. for 10 minutes on a PCR heating block. The temperature was reduced to 23° C. at a rate of 2 degrees a minute.

For membrane tethering runs, the bilayer was formed with 99% DPhPC. 1% 16:0Cap Biotinyl PE. Once the bilayer was formed, 1 nM of StrandDNA3 was added to the cis chamber and mixed well. A control section was recorded for 5 minutes at +180 mV to obtain DNA binding events to the nanopore. After the control section was recorded, 5 nM of KF (exo minus) (NEB) was added and the signal was recorded for 5 minutes at +180 mV.

For runs where the analyte is in solution, the bilayer was formed with 100% DPhPC.StrandDNA6 was produced by hybridising StrandDNA4 and StrandDNA5 at equimolar concentrations. Hybridisation was performed by heating to 50° C. on a PCR block for 10 minutes, then cooling to 23° C. at 2° C./min. Once the bilayer is formed, 400 nM of StrandDNA6 was added to the cis chamber and mixed well. A control section was recorded for 5 minutes at +180 mV to obtain DNA binding events to the nanopore. After the control section was recorded, 800 nM of KF (exo minus) (NEB) was added and the signal was recorded for 5 minutes at +180 mV.

The open-pore level was visually estimated, and DNA translocation events were defined to be occasions when the data dropped below a threshold placed at about 5 sigma below the pore level (where sigma is the standard deviation of the noise). Any obvious artifacts were manually removed from the data before event detection was performed. Shown in the figures is the mean current level of each event in pA (vertical axis) vs the length of the event in seconds (horizontal axis). Note that the horizontal axis is displayed using a logarithmic scale, since the event lengths range from less than a millisecond to as much as 10 seconds. In all four cases there were also numerous very short events (less than 1 ms) which have been excluded. This is because they are too short for their current levels to be reliably estimated, and because they do not serve to distinguish between the different conditions shown.

```
                                           (SEQ ID NO: 22)
StrandDNA1: 5'-Biotin-TTTTTTTTTTTTTTTTTTTTTTTTTT

TTTTTTTTTTTTTTTTTTTTTTTTTTTTTTTTTTTTTTGGCTACGA

CCTGCATGAGAATGC-3

(SEQ ID NO: 23)
StrandDNA2: 5'-CTCACCTATCCTTCCACTCACCCCCAAAAACCC

CCCAAAAAACCCCCAAAAAAGCA TTCTCATGCAGGTCGTAGCC-3'

(SEQ ID NO's: 22 and 23)
StrandDNA3: StrandDNA1 hybridised to StrandDNA2

(SEQ ID NO: 24)
StrandDNA4: 5'-AACCCCCAAAAACCCCCAAAAACCCCCAAAAACCC

CCAAAAACCCCCAAAAACCCCCAA AAACCCCCAAAAACCCCCATAGAGA

CAAGAATAACGAAGTA-3'
```

```
                                           (SEQ ID NO: 25)
StrandDNA5: 5'-TACTTCGTTATTCTTGTCTCTAT-3

(SEQ ID NO's: 24 and 25)
StrandDNA6: StrandDNA4 hybridised to StrandDNA5
```

2.2 Results

Figure 3:
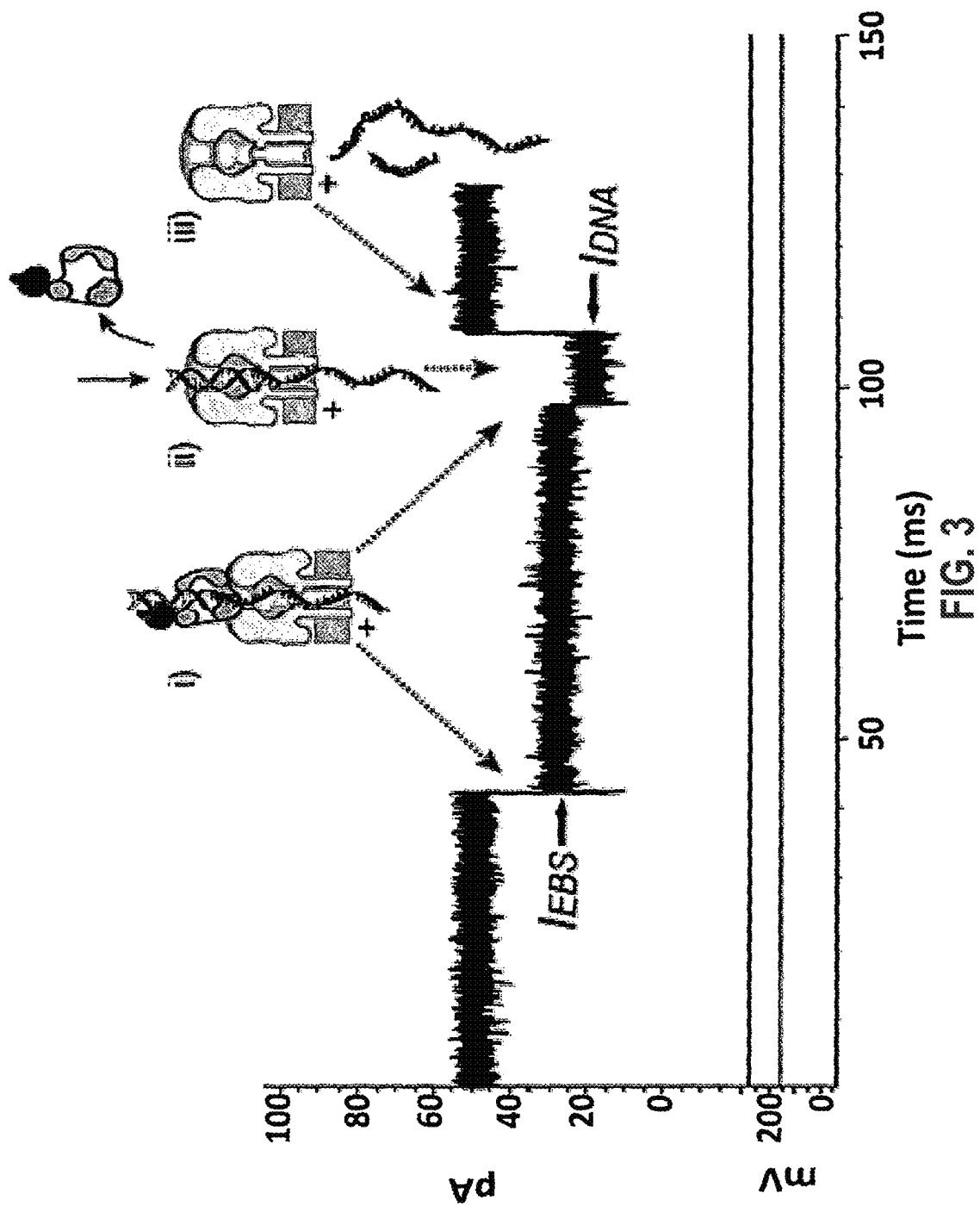
FIG. 3 shows capture of a DNA-enzyme complex, followed by dissociation of the DNA and the enzyme, and subsequent DNA de-hybridisation.

An experiment has been devised that allows a DNA handling protein to be assessed for its ability to hold onto DNA under the application of a potential. In this experiment, a DNA-enzyme complex is pulled into the nanopore resulting in a characteristic current level. When the DNA-enzyme complex dissociates, the DNA is pulled deeper into the nanopore resulting in a second current level. The DNA then completely translocates through the nanopore resulting in an open pore and resetting the system to its original state. The kinetics of the DNA-enzyme binding can be assessed by examining the duration of the enzyme-bound state over multiple repeats of this process (FIG. 3).

In recent work, a polymerase has been used to control the translocation of a DNA strand. To run such an experiment, the DNA concentration is ideally 100-1000 nM to be captured by the nanopore. As the enzyme binds to the DNA, it is preferable for the enzyme concentration to be at a similar molarity to the DNA, or in excess to the DNA. It is common for enzyme concentrations to be used at double the DNA concentration to ensure that a large proportion (preferably all) of the DNA forms an enzyme-DNA complex. This places a high demand on the quantity of material required. It is therefore desirable be have a system that uses less DNA and hence, less enzyme.

One method of achieving this is to tether the DNA to the lipid membrane. As presented, the rate of DNA insertion can be greatly increased by enhancing the interaction between DNA and membrane. This can produce rates that are comparable to those when the DNA is free in solution, but using 1.000 to 10,000 times less material. By using a lower concentration of DNA, the concentration of enzyme used can be greatly reduced (see FIG. 4).

A suitable DNA handling protein is the Klenow Fragment (KF) (N. A. Wilson, R. Abu-Schmays, B. Gyarfas, H. Wang, K. R. Lieberman. M. Akeson and W. B. Dunbar (2009). Electronic Control of DNA Polymerase Binding and Unbinding to Single DNA Molecules. *ACS Nano* 3, 995-1003). The Klenow fragment is a large protein fragment produced when DNA polymerase I from *E. coli* is enzymatically cleaved by the protease subtilisin. It retains the 5'-3' polymerase activity and the 3'→5' exonuclease activity for removal of precoding nucleotides and proofreading, but loses its 5'→3' exonuclease activity. The KF can also be genetically engineered to remove the remaining 3'→5' exonuclease activity. This DNA handling protein typically binds to the DNA at the interface between single stranded and double stranded DNA (primer/template junction) and can catalyse the replication of the DNA strand through the addition of nucleotides. Klenow fragment has been investigated for Strand Sequencing approaches but has been found to have binding times of 1-100 ms when pulled on top of a nanopore by the application of a potential.

Figure 6:
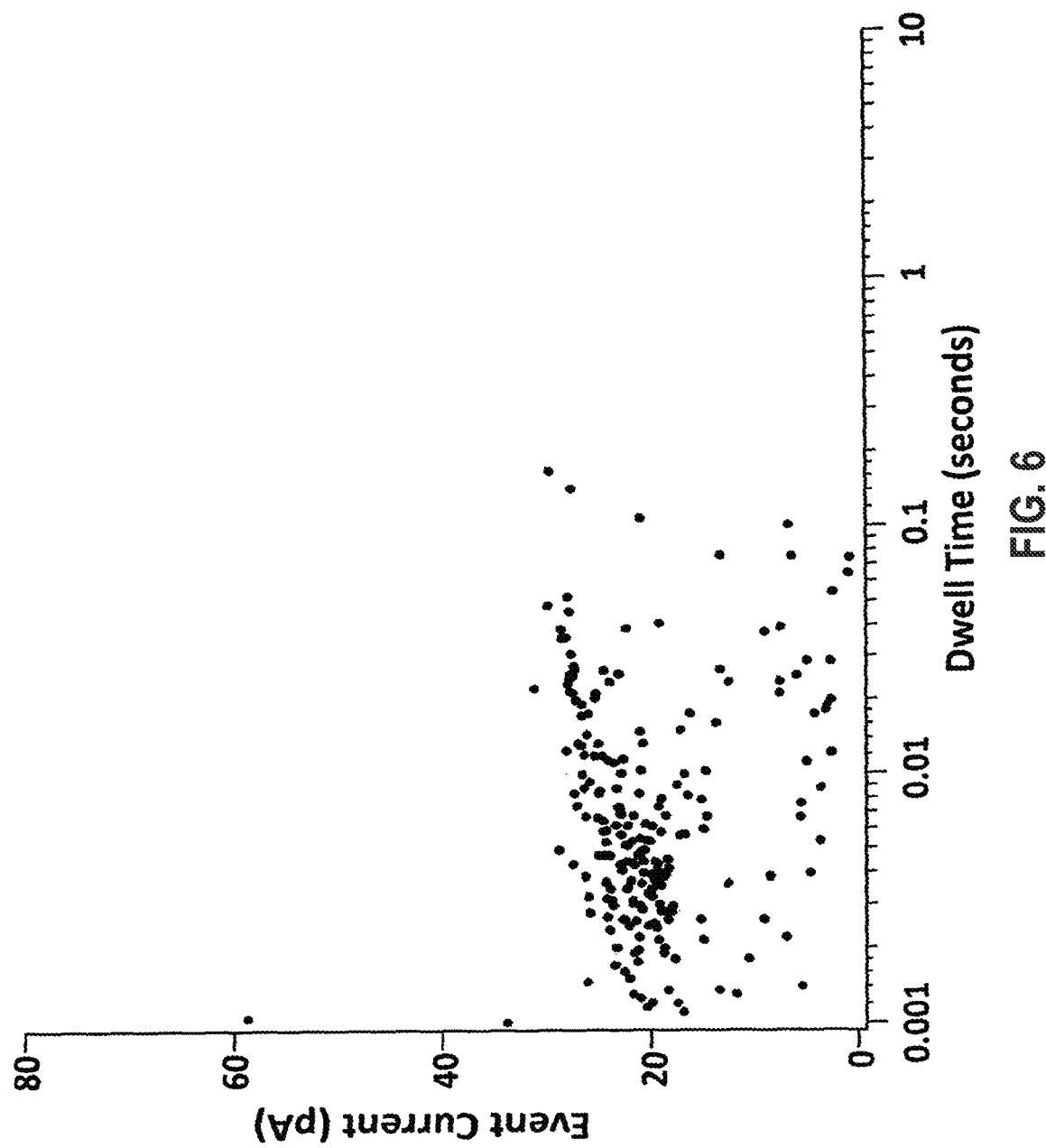
FIG. 6 shows KF binding times on top of the nanopore for non-tethered analyte (DNA) in the presence of KF (DNA concentration=400 nM, KF concentration=800 nM). KF binding was 1-100 ms.
Figure 7:
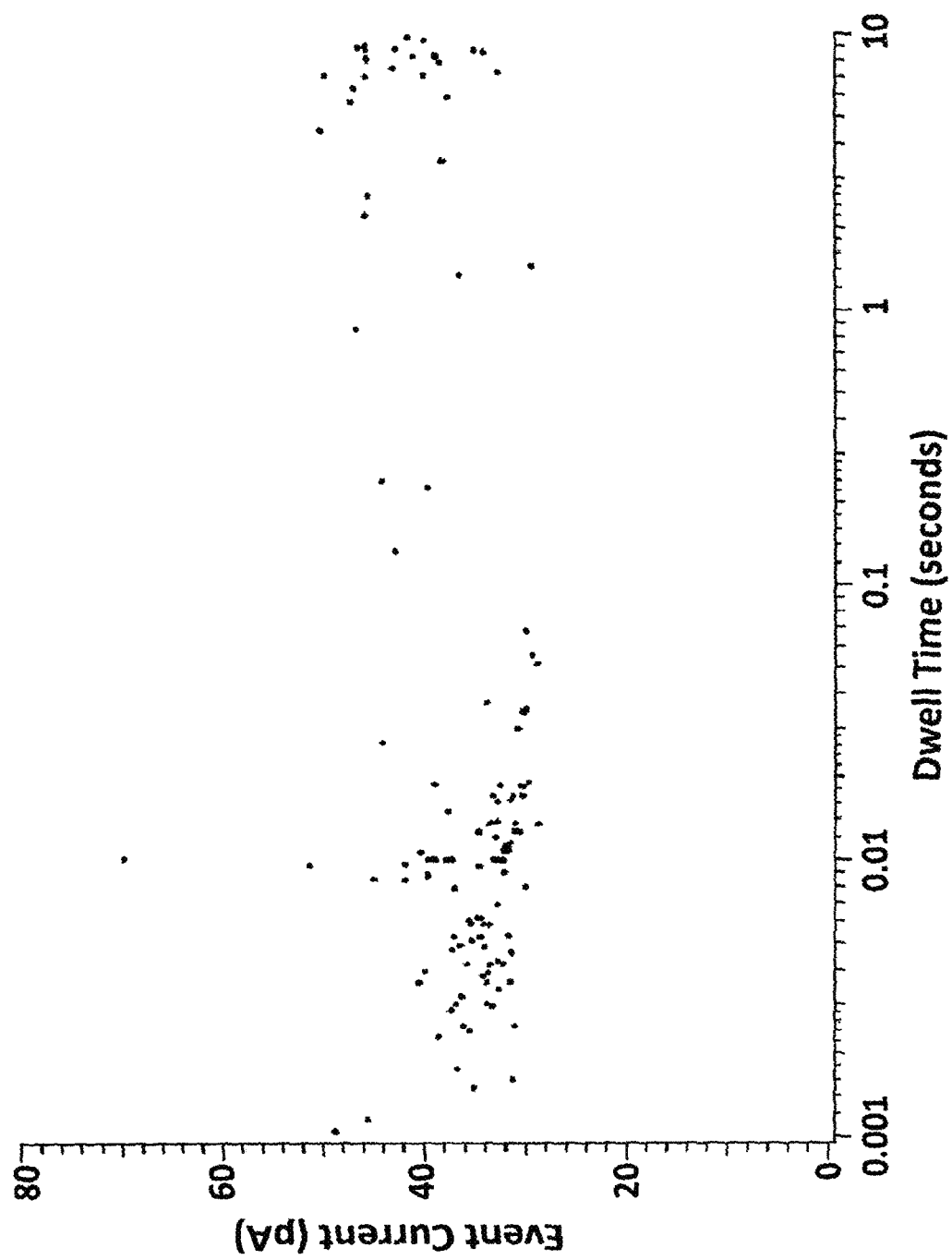
FIG. 7 shows KF binding times on the top of the nanopore for tethered analyte (DNA) in the absence of KF (DNA concentration=1 nM).
Figure 8:
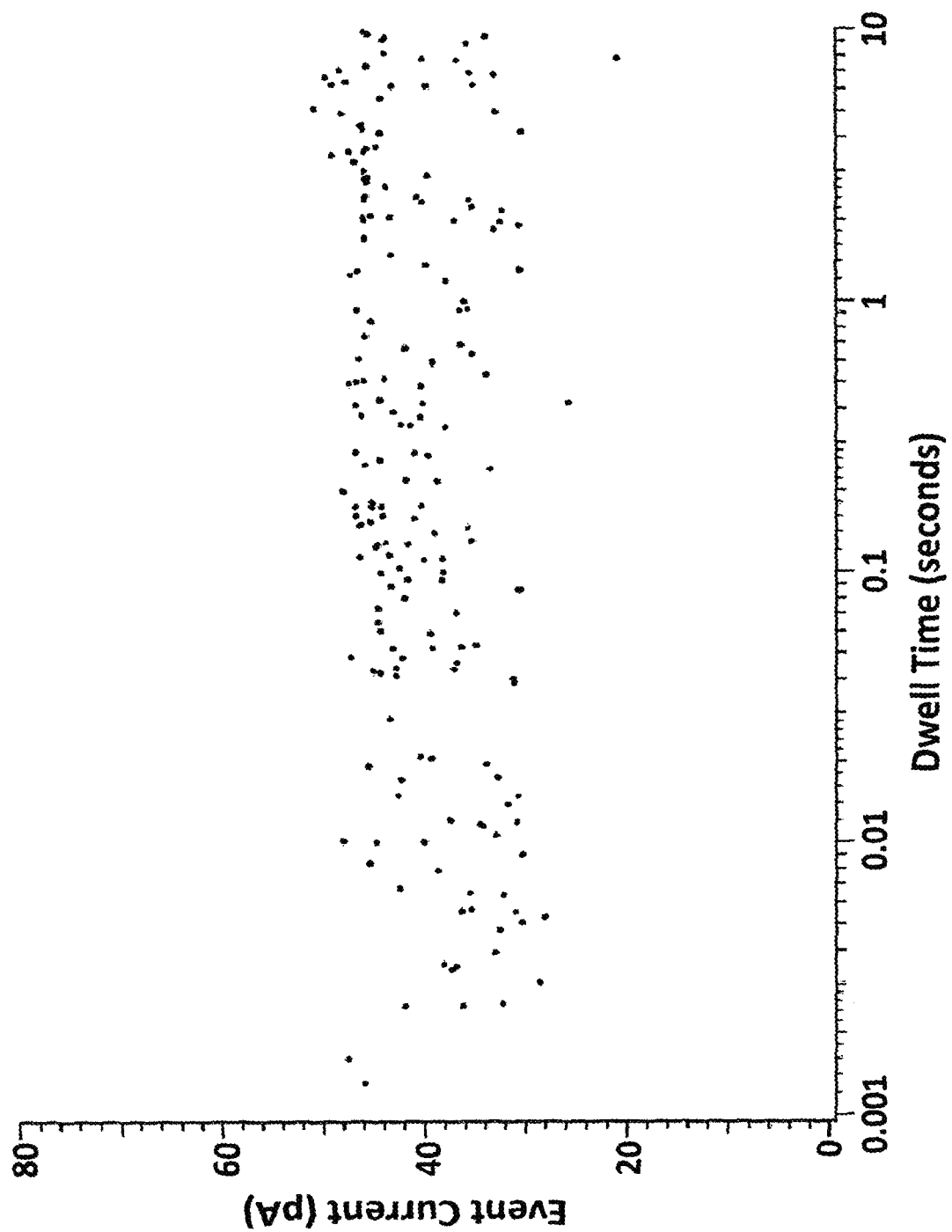
FIG. 8 shows KF binding times on top of the nanopore for tethered analyte (DNA) in the presence of KF (DNA concentration=1 nM, KF concentration=5 nM). KF binding was 0.1-10 s.

We screened the KF in a membrane tethered analyte setup as shown above (FIG. 4). When the DNA is in solution, the binding time of the KF-DNA complex is 1-100 ms (FIGS. 5 and 6) (similar to published results (ref Wilson/Akeson 2009)). This is too short to be useful for a Strand Sequencing method as a duration of 100 ms would only allow a few nucleotides to be read. However, when the DNA is tethered to the lipid membrane, the binding time increases to 0.1-10 s (FIGS. 7 and 8).

2.3 Conclusions

The duration of the enzyme-DNA complex on top of the pore is a function of the force from the applied field acting on the charged DNA strand. The ability of the protein to resist this force determines the length of time that the complex remains intact on top of the pore. The longer dwell time for the tethered DNA may be due to the mobile lipid molecules applying an additional force on the strand in the pore as it diffuses across the lipid membrane. This force negates the force applied by the applied field and the net force that the KF experiences is reduced. This setup benefits from the advantages that a high field offers (e.g. higher signal to noise, faster DNA capture), but still allows the DNA handling protein to have a long binding time on top of the pore.

The tethering approach offers another means for controlling enzyme behaviour on top of the nanopore. There are many possibilities for exploring this concept. By varying the composition of the membrane, or changing a physical parameter, such as temperature, it would be possible to change the diffusion rate of the tethered molecule in the lipid bilayer, and hence, the force that the DNA-enzyme complex experiences at the nanopore. In the embodiment of exonuclease sequencing, increasing membrane fluidity may increase availability of polynucleotide to exonuclease. Membrane fluidity can be changed by adding agents such as cholesterol. In addition, the nature of the tethering agent could be changed to control the diffusion rate of the tethered analyte to produce a similar effect. It is likely that tethering to a large species, such as a protein would yield a slower diffusion rate compared to tethering to a small molecules such as a lipid. It has been shown that the enzyme rate when it is complexed with polynucleotide and drawn into the nanopore will be affected by the field applied across the nanopore. It is likely that the diffusional force from analyte tethering will reduce the net force that the enzyme on the pore experiences. We anticipate being able to control the rate of polymer movement by combining the force from an applied potential with the diffusional force from analyte tethering. Another potential use of this effect is to control the strand speed through the pore without the use of a DNA handling protein. The force applied by the applied potential could be matched by the diffusional force of the membrane.

3. Example 3

More Strand Sequencing

In recent work, Phi29 DNA polymerase has been used to control the translocation of a DNA strand through α-hemolysin (Akeson et al., 2010, J Am Chem Soc. 2010 Dec. 22; 132(50):17961-72). Two modes of controlled movement of a DNA strand through a nanopore have been reported using Phi29 as a molecular motor, both methods relying on its action at the double/single stranded DNA juncture on a 5'-overhanging duplex. Movement can occur either by polymerisation from the priming strand that is hybridised opposite to the strand being interrogated or by an unzipping method where the priming strand is sequentially unhybridised from the strand being interrogated to reveal more and more of the targets sequence that was previously duplex DNA.

3.1 Materials and Methods

As presented for single stranded DNA, the tethering moiety can be varied to generate strands that display either a transient interaction with the bilayer or a more long duration tethering, for example with cholesterol of biotin: streptavidin respectively. For dsDNA analytes it might be considered that duplex DNA analytes which display transient binding behaviour might be more suitable for strand sequencing so as to enable the enzyme to fully unzip the analyte and clear the nanopore ready for the next.

Complementary Oligos (ONLA1346 and ONLA1347, 65 nt and 31 nt respectively) were designed that contained on the target strand (ONLA1346) a cholesterol group at the 3' and a polyC extension containing a single A at the 5'. When hybridised these Oligos give a DNA duplex of 31 bp with a 34 nt 5' overhang so that the target strand can be threaded into and captured by the nanopore 5' first. The unzipping can then be tracked by looking at the movement of the single A, in the polyC background, through the reader head of the nanopore. For comparison with non-tethered analytes a strand identical in sequence to the target strand was designed but which lacked the cholesterol group (ONLA1049).

Single channel recordings were performed using a mutant MspA-NNNRRK pore (ONLP2726) in combination with Phi29 DNA polymerase. A single channel was obtained and the cis buffer perfused with 10 ml of fresh buffer (400 mM KCl, 10 mM HEPES pH8.0) to minimise the chance of single channel insertion. After a 5 minute control section DNA was added to either 0.5 nM or 100 nM, for tethered and non-tethered experiments respectively. A number of short duration events (~10 ms) were observed after the addition of DNA that are proposed to be the duplex DNA being captured by the nanopore and the primer being stripped from the template by the force of the pore. After 5 mins Phi29 DNA polymerase was added to the cis chamber to give either 10 nM or 200 nM, again respectively for tethered and non-tethered experiments.

Oligonucleotides Used:

ONLA1346
(SEQ ID NO: 26)
CCCCCCCCCCCCCCCACCCCCCCCCCCCCCCCCCCCTATTCTGTTTATGTT
TCTTGTTTGTTAGCC-Chol

ONLA1347
(SEQ ID NO: 27)
GGCTAACAAACAAGAAACATAAACAGAATAG

ONLA1049
(SEQ ID NO: 28)
CCCCCCCCCCCCCCCACCCCCCCCCCCCCCCCCCCCTATTCTGTTTATGTT
TCTTGTTTGTTAGCC

Figure 9:
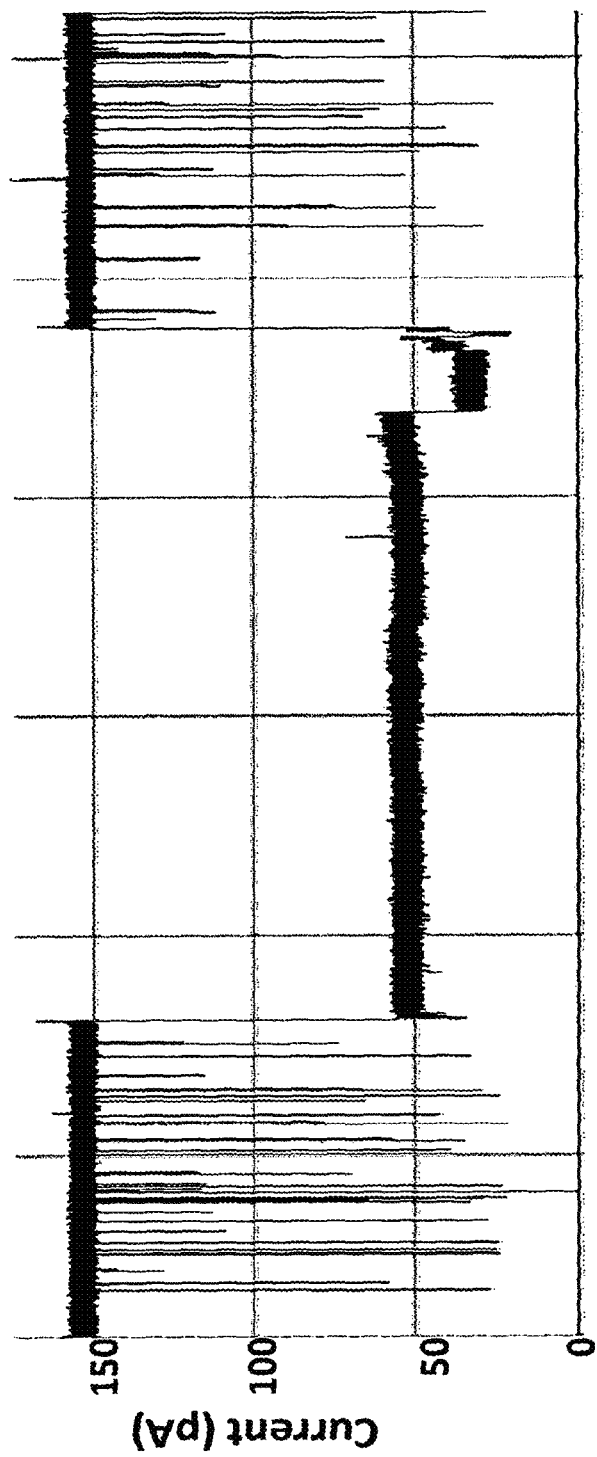
FIG. 9 shows an example of a Phi29 DNA polymerase mediated unzipping event of transiently tethered dsDNA. The drop in current from the open pore level is thought to be a blockade caused by capturing a DNA:protein complex. This captured complex resides on the nanopore for ~5 seconds giving a constant current level before rapidly changing between levels and then finally returning to the open pore level. This is thought to be a pause before unzipping is initiated and a single A moves through the reader head so giving the oscillation in current. When the duplex has been fully unzipped the target strand translocates, the primer and polymerase dissociate and so the current returns to the open pore level.
Figure 10:
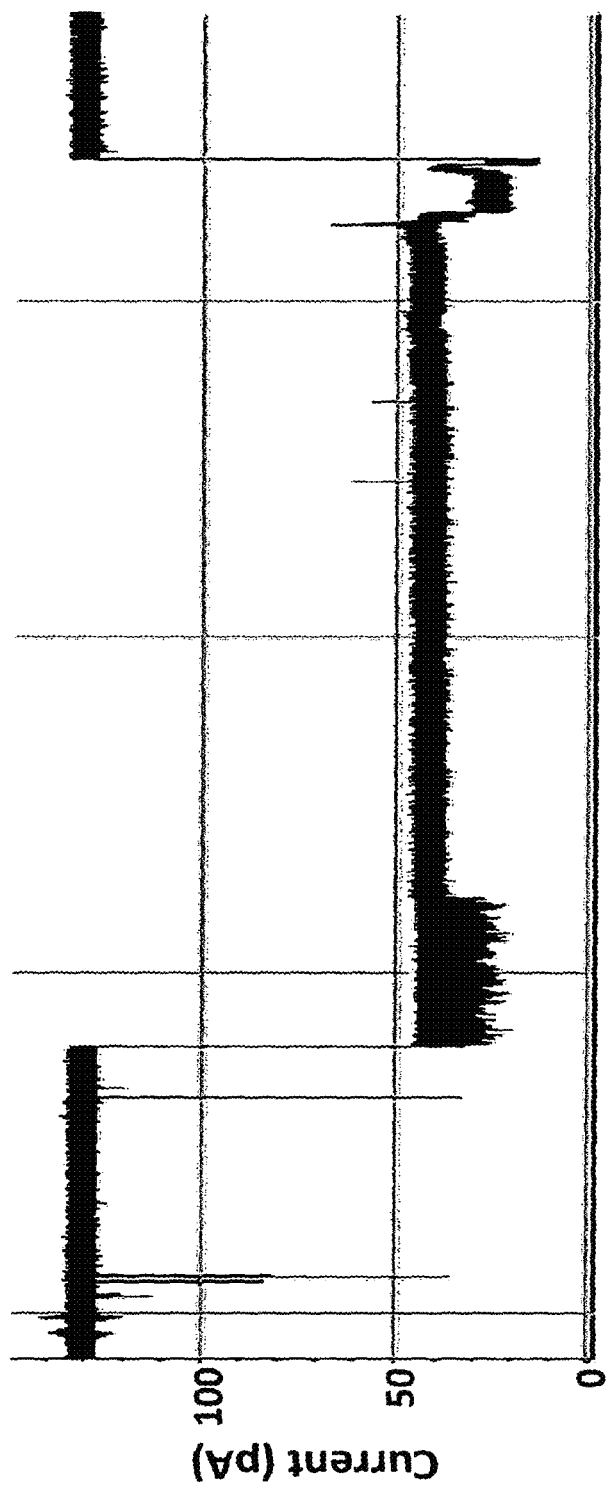
FIG. 10 shows an example of a Phi29 DNA polymerase mediated unzipping event of solution dsDNA. The drop in current from the open pore level is thought to be a blockade caused by capturing a DNA:protein complex. This captured complex resides on the nanopore for ~12 seconds giving a constant current level before rapidly changing between levels and then finally returning to the open pore level. This is thought to be a pause before unzipping is initiated and as the single A moves through the reader head so giving the oscillation in current. When the duplex has been fully unzipped the target strand translocates, the primer and polymerase dissociate and so the current returns to the open pore level.

PolyT-50 mer_XXXX_Sense
(SEQ ID NO: 29)
TTTTTTTTTTTTTTTTTTTTTTTTTTTTTTTTTTTTTTTTTTTTTTTTTT
XXXXGGTTGTTTCTGTTGGTGCTGATATTGC PhiX 235 bp Antisense
(SEQ ID NO: 30)
Chol-GTTAGACCAAACCATGAAACCAACATA PhiX 400 bp Antisense
(SEQ ID NO: 31)
Chol-GACCGCCTCCAAACAATTTAGACA -continued PhiX 822 bp Antisense
(SEQ ID NO: 32)
Chol- GGCAATCTCTTTCTGATTGTCCAG 3.2 Results After addition of the Phi29 DNA polymerase a number of long duration events were observed in both experiments that are proposed to be capture of the DNA:protein complexes. These events show a short dwell time at a constant level before oscillating between states, which are thought to occur on initiation of unzipping and the A beginning to move through the reader head of the pore. An example of this is shown in FIGS. 12 and 11 for both the tethered (FIG. 9) and non-tethered (FIG. 10) experiments.

Figure 11A:
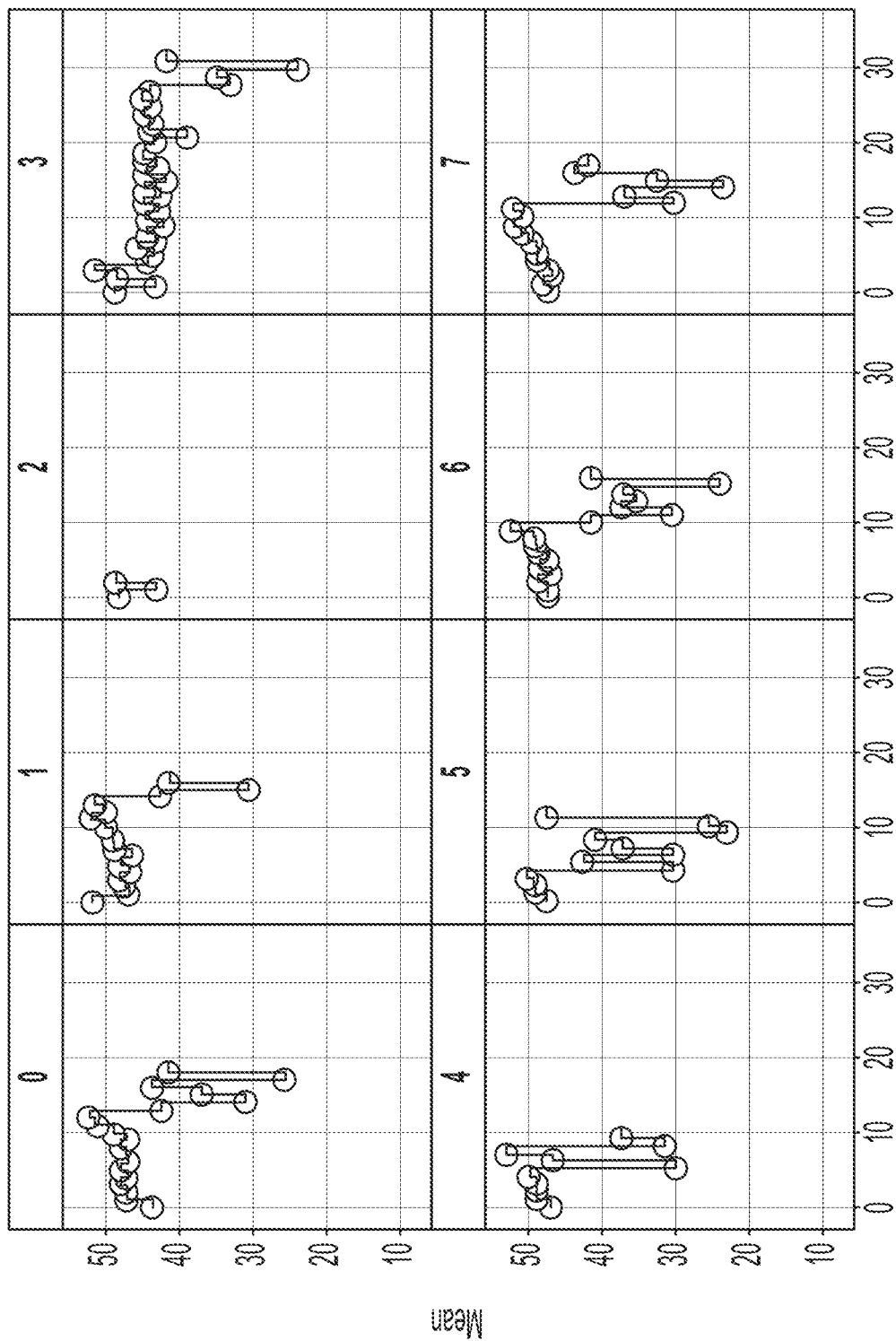
FIGS. 11A-11B show an example of event sequences from one unzipping run for non-tethered dsDNA analyte. The number of levels observed as well as the level and duration for these are broadly consistent with the tethered experiments.
Figure 11B:
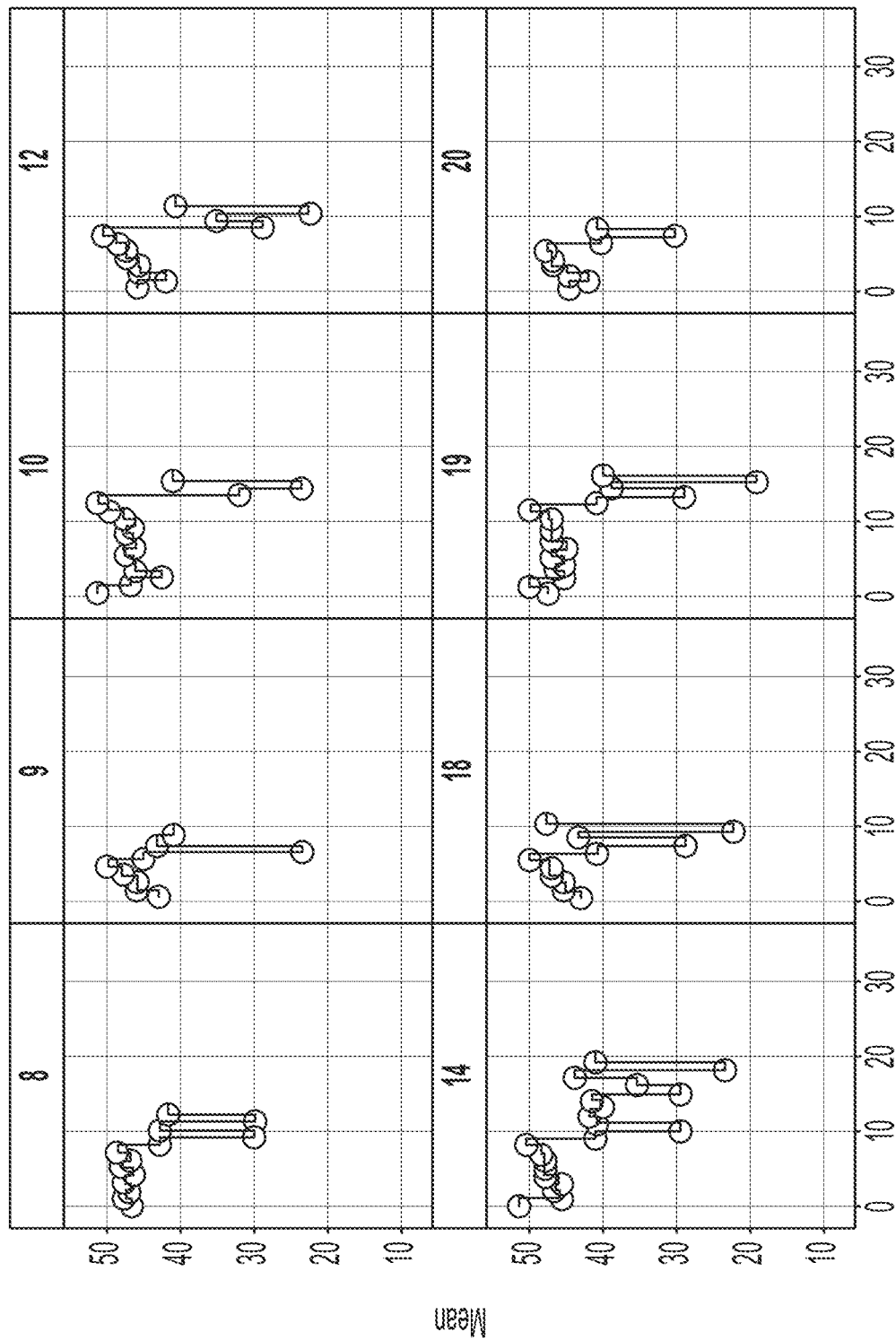
Figure 12A:
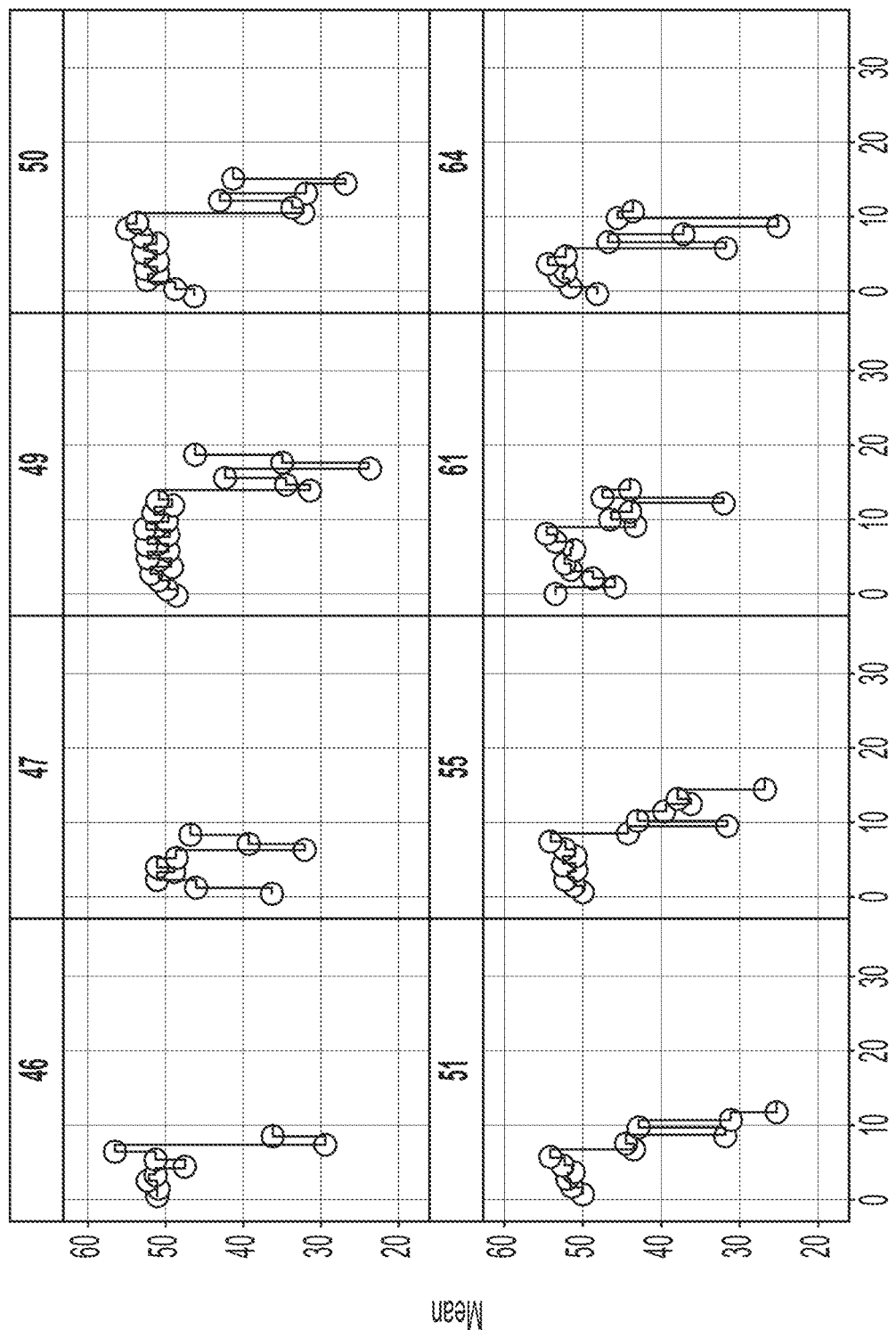
FIGS. 12A-12B show an example of event sequences from one unzipping run for tethered dsDNA analyte. The number of levels observed as well as the level and duration for these are broadly consistent with the solution (non-tethered) DNA experiments.
Figure 12B:
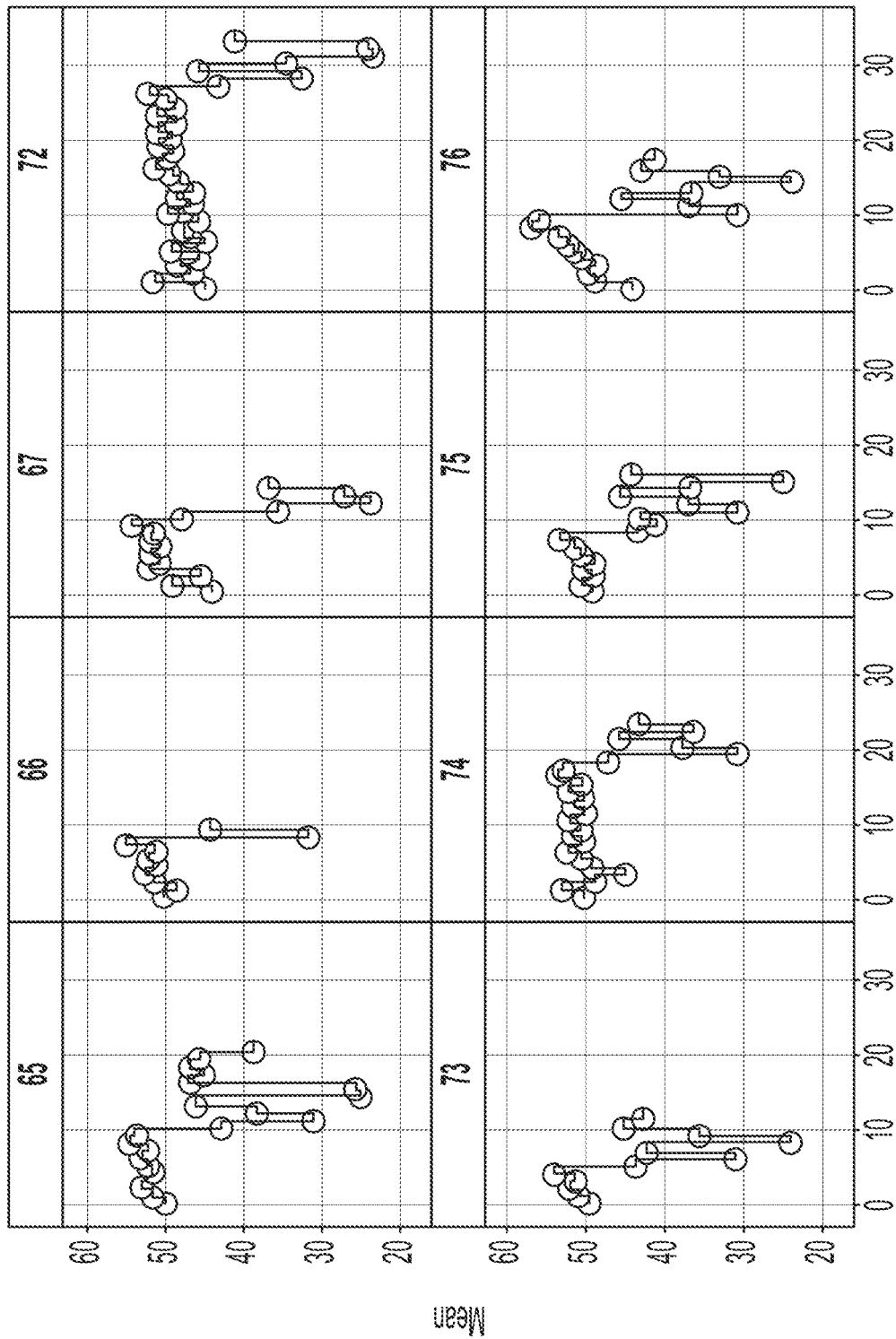

Analysis of all unzipping events for both the tethered and solution DNA events show a broadly constituent pattern for the number of observed states, the mean vs dwell time for each state and the mean vs standard deviation for each (FIG. 11 for non-tethered and FIG. 12 for tethered).

The position of the cholesterol is not set as being at the 3' of the target strand and can be varied to the 5' of either the template or primer strand or within a hairpin. Due to the requirement for the enzyme to sit at 3' of the primer strand, the juncture between single and double stranded DNA it is thought this is not a suitable site for tethering, however this has not been demonstrated experimentally.

Figure 13:
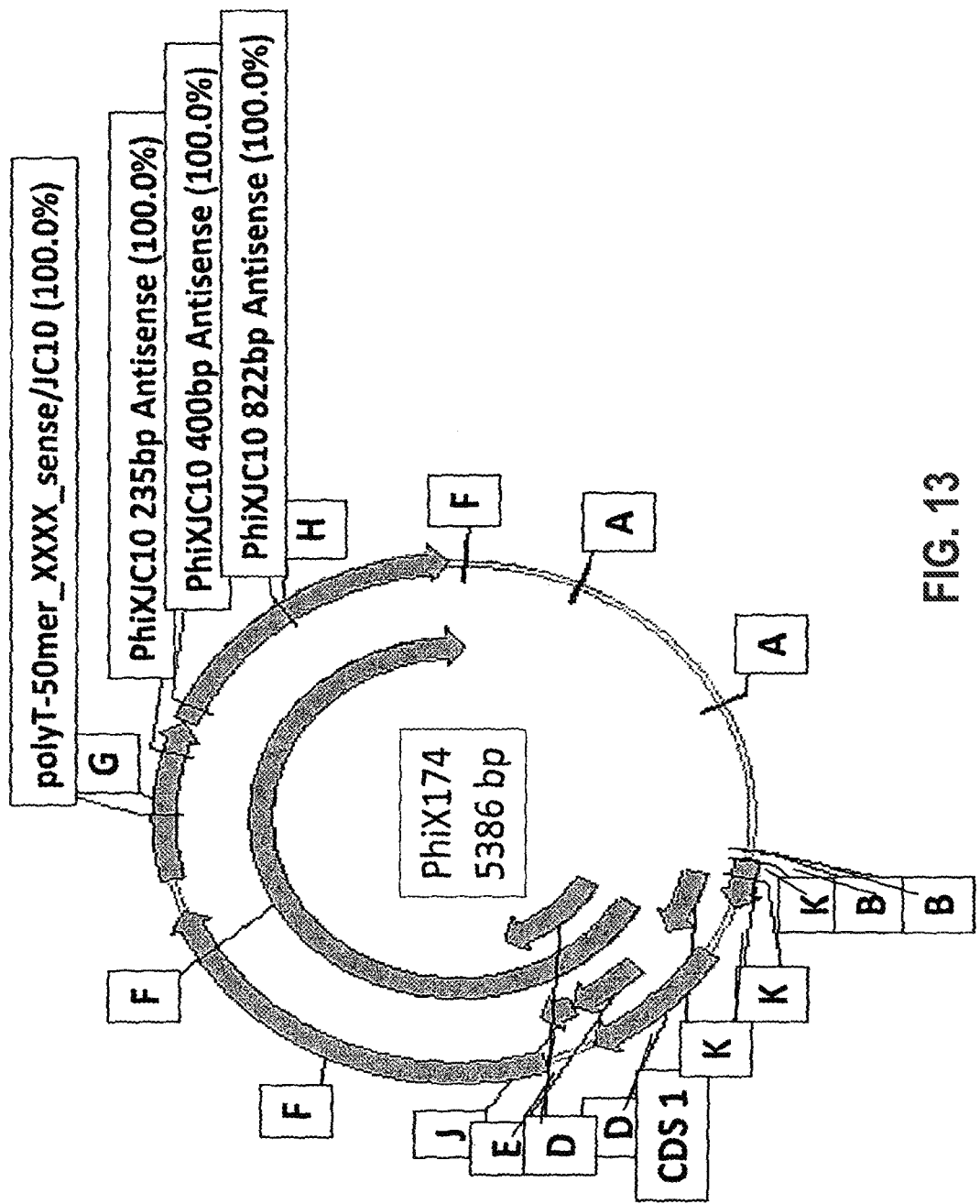
FIG. 13 shows a plasmid map of tethered strand sequencing analytes from genomic DNA. Primers were designed complementary to PhiX 174 genomic DNA. The same sense primer was used for all and contained a 5'-50polyT region followed by 4 abasic sites before the complementary region. The hybridisation sites for the antisense primers were varied according to the desired fragment size. Each antisense primer contained a 5'-cholesterol group.
Figure 14:
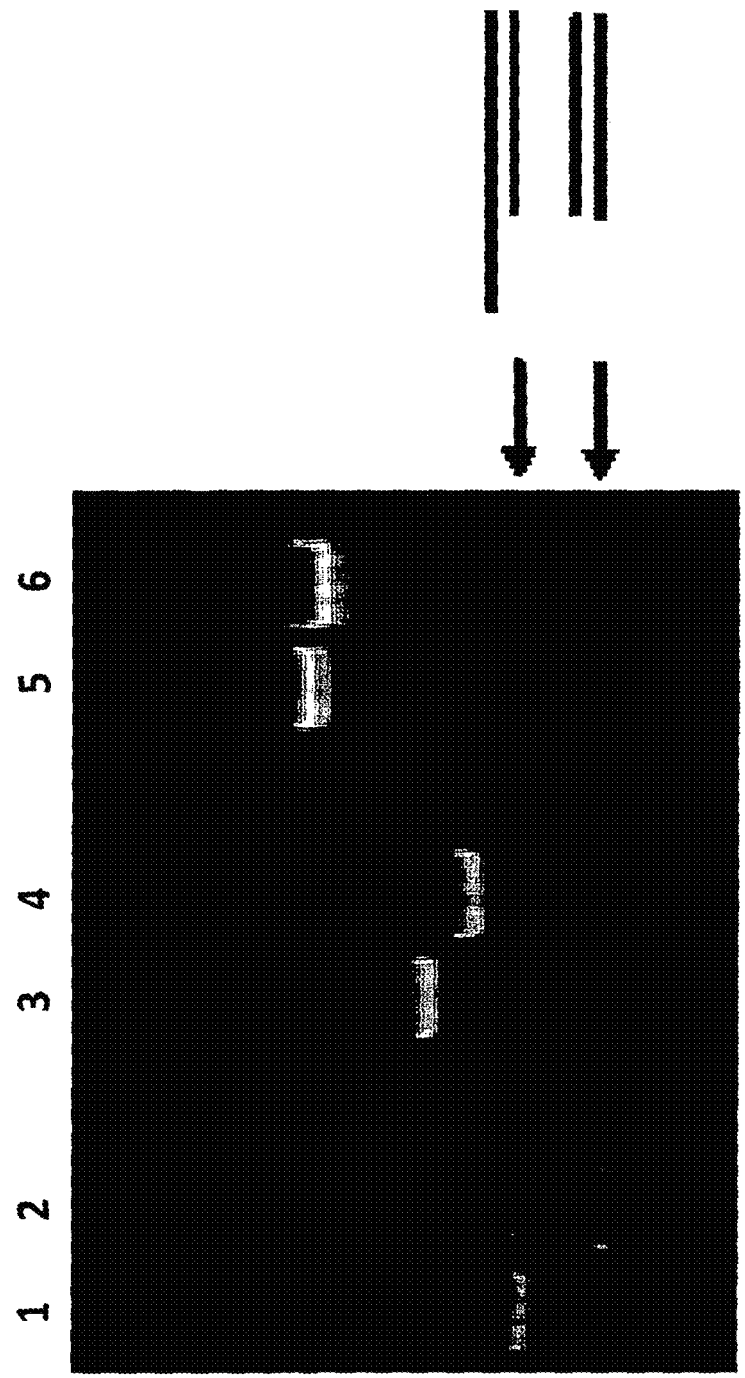
FIG. 14 shows PCR generation of tethered strand sequencing analytes from genomic DNA. Primers were designed complementary to PhiX 174 genomic DNA. The same sense primer was used for all and contained a 5'-50polyT region followed by 4 abasic sites before the complementary region. The hybridisation sites for the antisense primers were varied according to the desired fragment size. Each antisense primer contained a 5'-cholesterol group. To confirm presence of the 50polyT region to the 5' of the sense strand, fragments were digested with the 5'-3' single strand specific Reel exonuclease (NEB) and this was analysed on a gel. Lane 1 contains 50 nt ssDNA, 235 bp dsDNA only. Lane 2 contains 50 nt ssDNA, 235 bp dsDNA which has been digested with the 5'-3' single strand specific Reel exonuclease (NEB). Lane 3 contains 50 nt ssDNA. 400 bp dsDNA only. Lane 4 contains 50 nt ssDNA, 400 bp dsDNA which has been digested with the 5'-3' single strand specific RecJ exonuclease (NEB). Lane 5 contains 50 nt ssDNA, 835 hp dsDNA only. Lane 6 contains 50 nt ssDNA, 835 bp dsDNA which has been digested with the 5'-3' single strand specific Reel exonuclease (NEB).

Whilst the tethering method works well for synthetic strands, where the attachment chemistry can be incorporated during the chemical synthesis of the oligonucleotide, applying it to samples derived from genomic DNA is more challenging. A common technique for the amplification of sections genomic DNA is using polymerase chain reaction. Here using two synthetic oligonucleotide primers a number of copies of the same section of DNA can be generated, where for each copy the 5' of each strand in the duplex will be the synthetic oligo. By using an antisense primer that has a 5' cholesterol group each copy of the target DNA amplified will contain a cholesterol group for tethering. The only problem with analyte generated by PCR is that it is either blunt ended or contains a single 3'-A overhang, neither of which are suitable for threading into a nanopore for strand sequencing. Addition of sections of single stranded DNA to the 5' of duplex DNA is not easily possible. A chemical or enzymatic ligation can be done but neither are highly efficient and also require further downstream reactions and purification steps. A PCR method was developed using a sense primer that as is usual contained a complementary section to the start of the target region of genomic DNA but was additionally proceeded with a 50 PolyT section. To prevent the polymerase from extending the complementary strand opposite the polyT section, to create a blunt ended PCR product as is normal, four abasic sites were added between the PolyT section and the complementary priming section. These abasic sites will prevent the polymerase from extend beyond this region and so the polyT section will remain as 5' single stranded DNA on each of the amplified copies (FIGS. 13 and 14).

Whilst this PCR method is an efficient way of attaching the 5' leader polyT section, other methods for incorporating the attachment chemistry are possible however, such as using terminal transferase to add to the 3' or via T4 polynucleotide kinase and ATPγS to add a reactive thiol to the 5' for chemical coupling. However, this method allows generation of tethered analytes in a form suitable for strand sequencing where the only limitation on size, and as such read length, is that imposed by the PCR (~20 kb).

Figure 16:
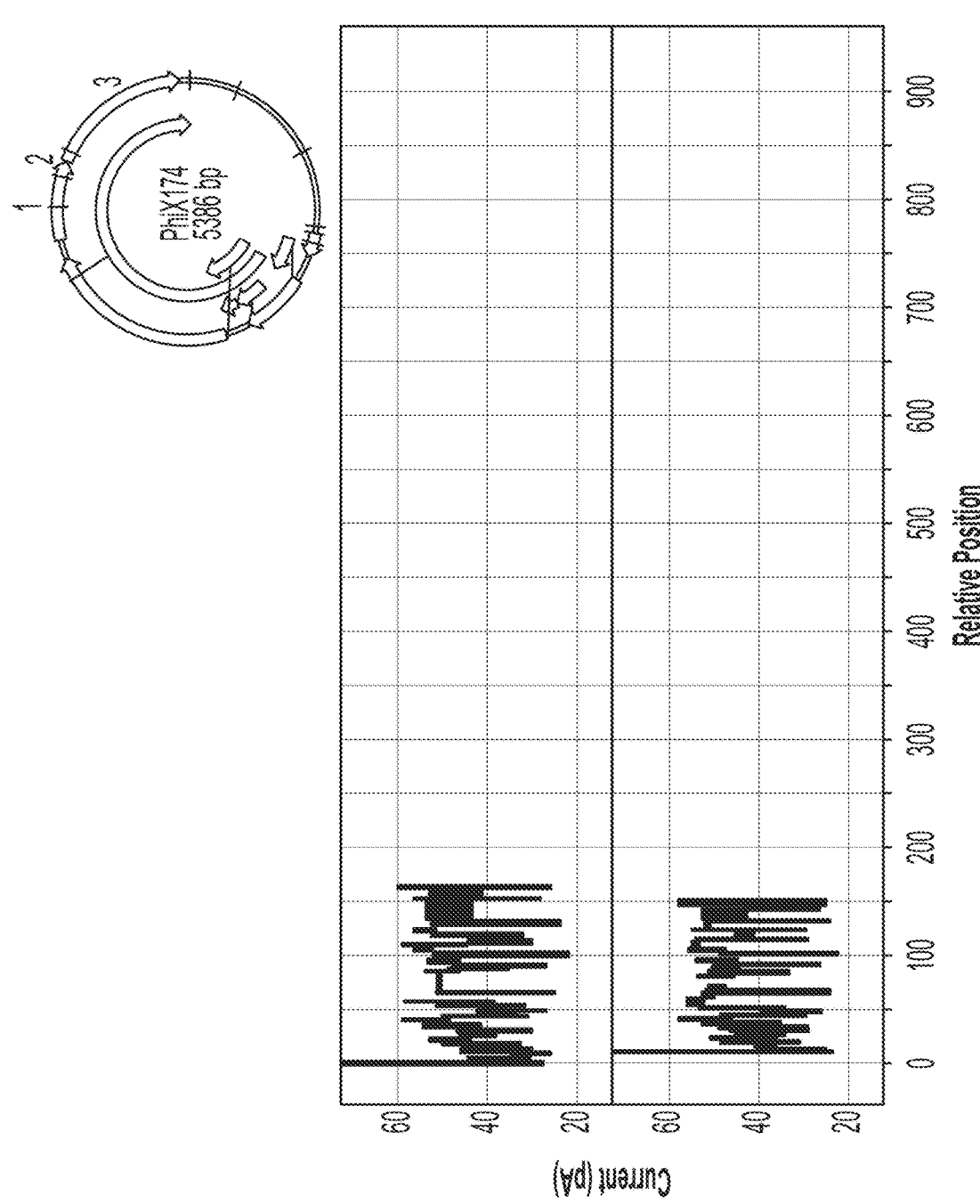
FIG. 16 shows unzipping events from the 200 bp PhiX 174 amplified fragment. This 200 bp sequence corresponds to the sequence between points 1 and 2 in the plasmid map shown. The 200 mer is aligned against the 800 mer sequences shown in FIG. 15 with zero leading and trailing gap penalties (i.e. it is free to start anywhere, but "internal" gaps are penalised). As expected, the 200 mer sections align with the front of the 800 mer.

Single channel recordings were carried out as described above but using these genomic DNA amplified fragments in order to observe any unzipping events (FIGS. 15 and 16). Several unzipping events were observed that progressed and also then exited of their own accord, so suggesting complete unzipping of the duplex DNA.

In order to observe an acceptable event rate for capturing DNA:protein complexes for strand sequencing from solution then 100 nM DNA and 200 nM Phi29 DNA polymerase is required. For the 800 bp fragment this is equivalent to ~50 ug of dsDNA per experiment, assuming the 1 ml chamber volume as used above. Using tethered dsDNA analytes the same acceptable event rate can be satisfied and exceeded using 0.1 nM DNA and 10 nM Phi29 DNA polymerase. For the 800 bp fragment this is equivalent to ~50 ng of dsDNA per experiment, assuming the 1 ml chamber volume as used above.

4. Example 4

Solid State Sequencing

The advantages demonstrated above for tethering to a lipid membrane can also be extended to solid state nanopore experiments. Nanopores can be produced in solids state materials and utilised in a similar manner to biological nanopores. Their use and fabrication has been well documented elsewhere (WO 00/79257: WO 00/78668; Dekker C, Nat Nanotechnol. 2007 April; 2(4):209-15; and Schloss J A, et al., Nat Biotechnol. 2008 October; 26(10):1146-53).

Nanopores in solid state materials, such as silicon nitride offer advantages over the biological channels as the pores. Solid state materials are far less fragile than lipid membranes. Nanopores in solid state material can be formed in a factory and have a long shelf life, unlike biological membranes which are often formed in situ. Recent advances with solid state nanopores also allow very thin materials such as graphene to be used which have unique properties (Golovchenko J, et al., Nature. 2010 Sep. 9; 467(7312):190-3; DrndićM, et al., Nano Lett. 2010 Aug. 11; 10(8):2915-21; and Dekker C, et al., Nano Lett. 2010 Aug. 11; 10(8):3163-7). Nanogaps in graphene have also been proposed (Postma, 2008. Rapid Sequencing of Individual DNA Molecules in Graphene Nanogaps).

A further embodiment of solid state membranes is to use a tunnelling current between two or more electrodes embedded in the nanopore. As an analyte passes through the pore (driven by a trans membrane potential), the analyte facilitates a tunnelling current between electrode. This current can be used to detect the identity of the analyte (Schloss supra; U.S. Pat. No. 7,253,434; and WO 2008/092760).

An alternative method to nanopores is to use nanogaps in solid state materials as sensors (Chen et al., Materials Today, 2010, 13(11): 28-41).

Solid state nanopore experiments can benefit from the advantages described above for lipid membranes. A key difference between the two membrane types is that amphiphilic membranes often are naturally mobile, essentially acting as a two dimensional fluid with lipid diffusion rates of $~10^{-8}$ cm s$^{-1}$, while membranes in materials like silicon nitride are solid. Although there may be advantages to tethering an analyte to a surface in a static fashion, it is desirable for the analyte to be able to move across with membrane so that multiple analyte molecules can interact with the detector.

There are a number of schemes that could be employed to tether an analyte to a solid state membrane (FIG. 17). The first approach would be to rely on the natural interaction of the analyte with an unmodified membrane, such as $Si_3N_4$. However, this provides very little control over the diffusion rate of the analyte on the surface. It is therefore preferable to modify the surface, the analyte, or both the surface and the analyte to provide the desired interaction.

Methods for chemically modifying solid state materials are well known in the art. Solid state nanopores have also been chemically modified, either through self-assembly in solution or by driving the reactive species through the nanopore under an applied potential (WO 2009/020682).

Figure 17A:
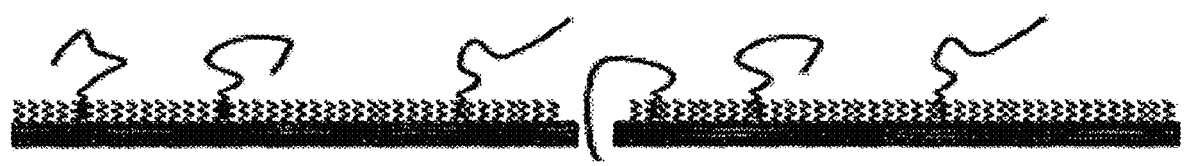
FIGS. 17A-17D show analyte tethering schemes for solid state nanopores.
Figure 17B:
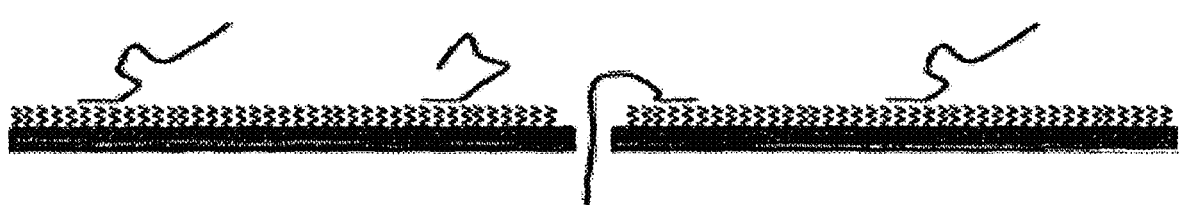

The first two schemes use a chemically modified membrane to produce a surface where the analyte can transiently interact with the layer (FIG. 17A, B).

In the first scheme, the tethering group of the analyte embeds itself into the modified layer (FIG. 17A). A long chain alkane could be attached to the surface and a tethering group such as cholesterol or an alkane would be used. The surface modification could be achieved by using a chloro-hexadecyl-dimethylsilane (or similar) and the methods described in WO 2009/020682.

In the second scheme, the tethering analyte does not embed into the layer, but resides on the surface. This could be achieved using hydrophobic as in the first scheme. In addition, similar methods could also be envisaged where the binding of the analyte to the surface is mediated by electrostatic, hydrogen bonding or Van der Waals interactions.

Figure 17C:
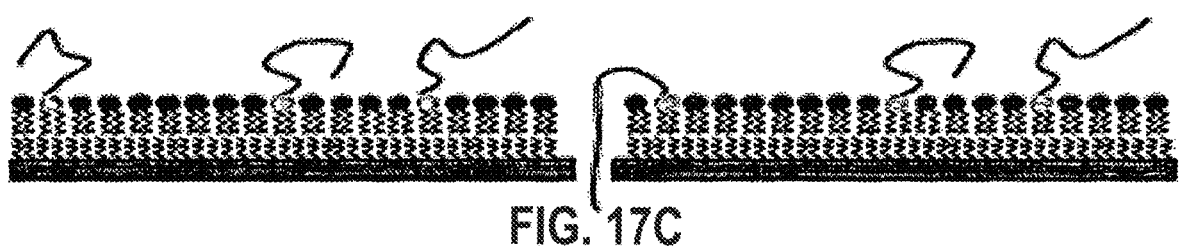

The third scheme is the most similar to the membranes used with protein nanopores. In this embodiment, the solid state membrane is modified to support a lipid monolayer (FIG. 17C). This approach has all the benefits of the examples presented above for lipid membrane tethering. Tethering can be achieved by using a cholesterol anchor or attaching, via the lipid headgroups, or through a receptor in the membrane. Methods for forming bilayers or monolayers on solid surfaces are well known in the art (Duran R S. et al., Langmuir. 2007 Mar. 13; 23(6):2924-7; and Cremer P S, et al., Surface Science Reports. 2006; 61:429444). When the surface is made hydrophobic, a lipid monolayer can be formed spontaneously from lipid vesicles in solution. The surface can be made hydrophobic in a number of ways, including plasma treatments (such as $CH_4$) or chemical methods, such as chloro-silane chemistry (WO 2009/020682), and gold-thiol coupling (Duran supra; and Cremer supra).

Figure 17D:
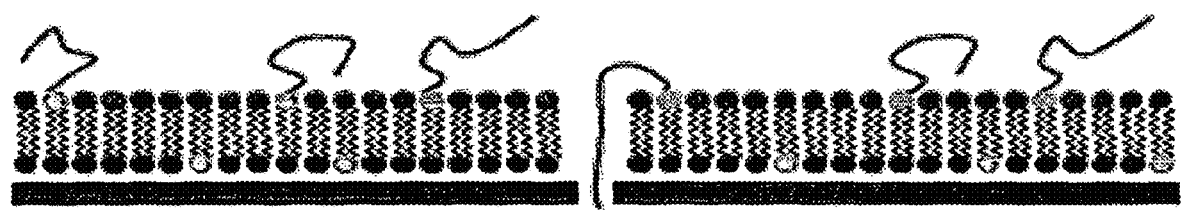
Figure 20A:
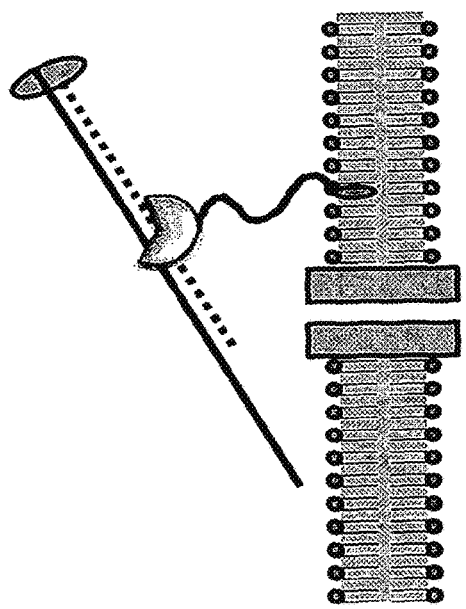
FIGS. 20A-20D show a schematic of one way of using a polynucleotide binding protein to control DNA movement through a nanopore employing a dsDNA binding protein to couple the DNA to the membrane.
Figure 20B:
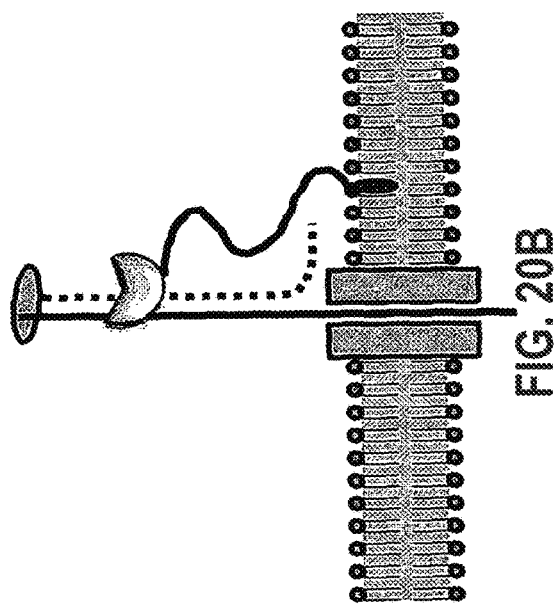
Figure 20C:
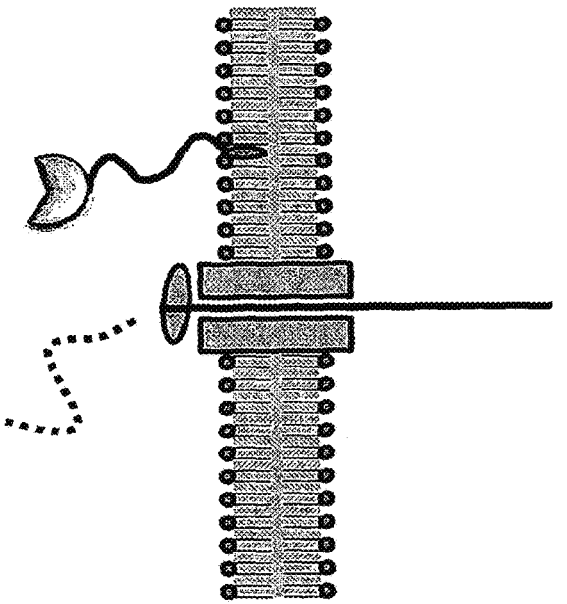
Figure 20D:
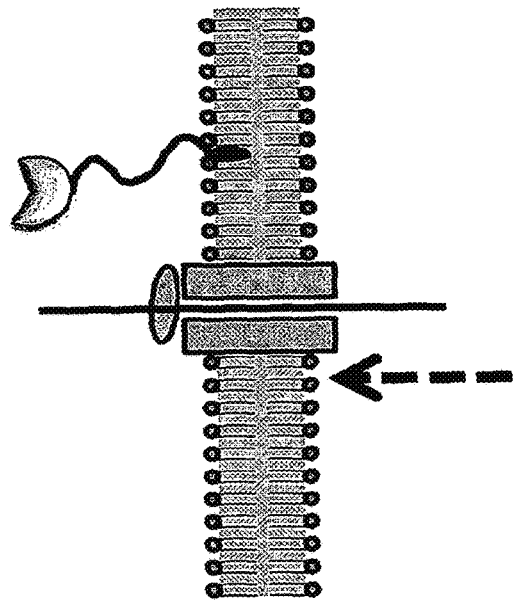
Figure 21A:
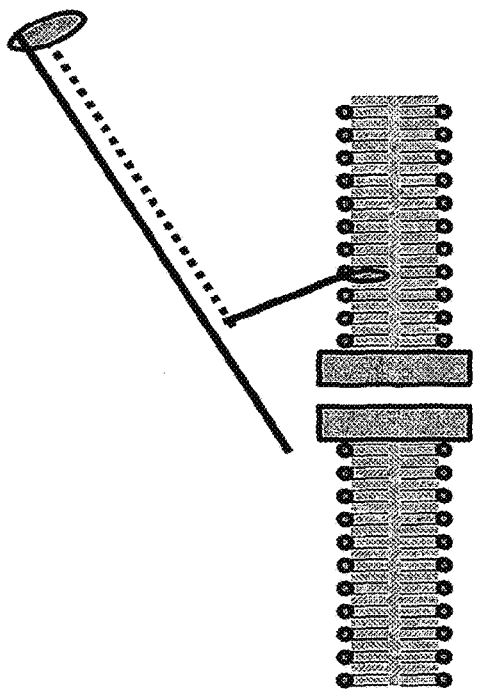
FIGS. 21A-21D show a schematic of one way of using a polynucleotide binding protein to control DNA movement through a nanopore employing a hybridised tether.
Figure 21B:
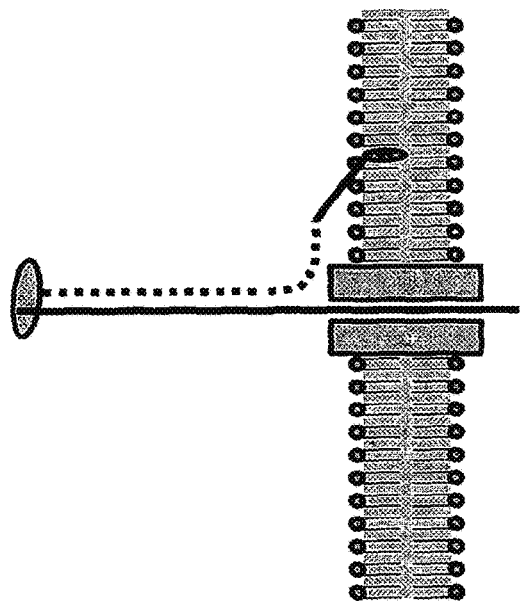
Figure 21C:
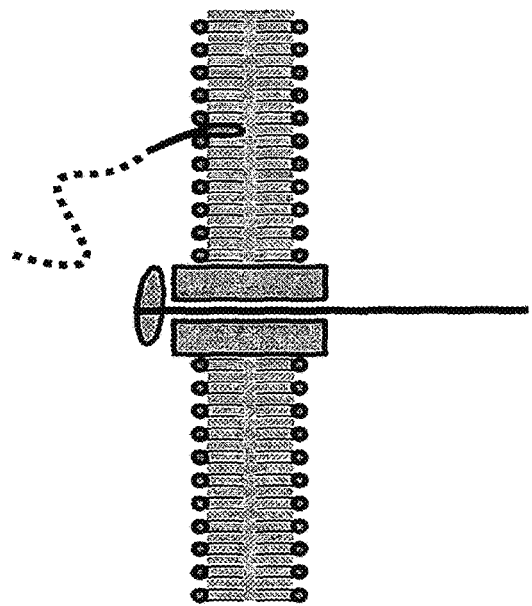
Figure 21D:
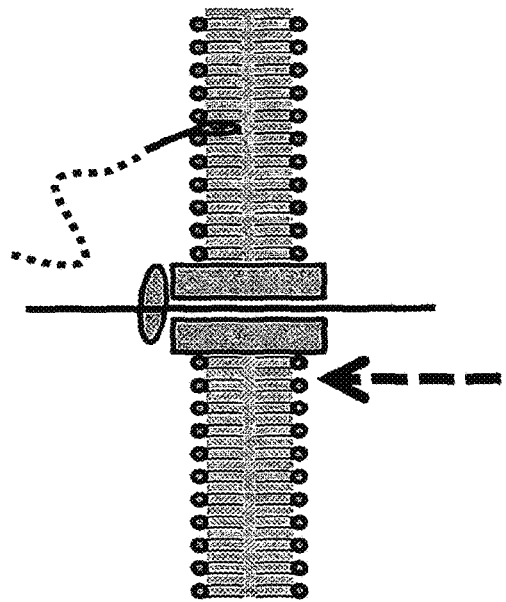
Figure 22A:
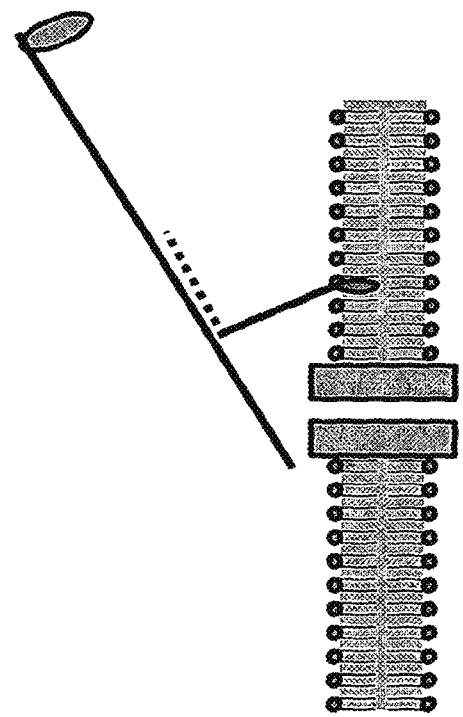
FIGS. 22A-22D show a schematic of one way of using a polynucleotide binding protein to control DNA movement through a nanopore employing a hybridised tether.
Figure 22B:
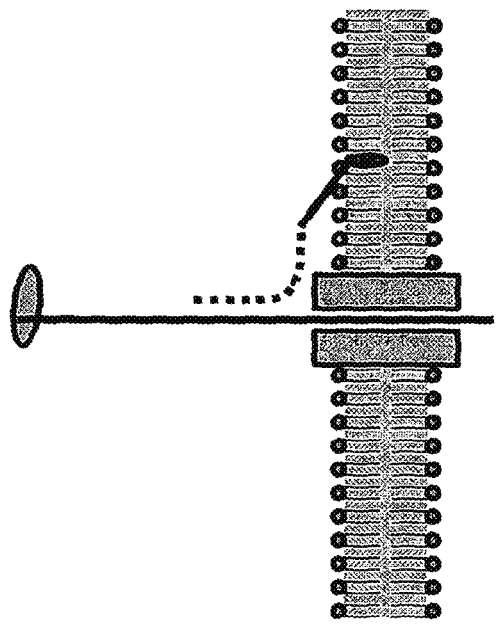
Figure 22C:
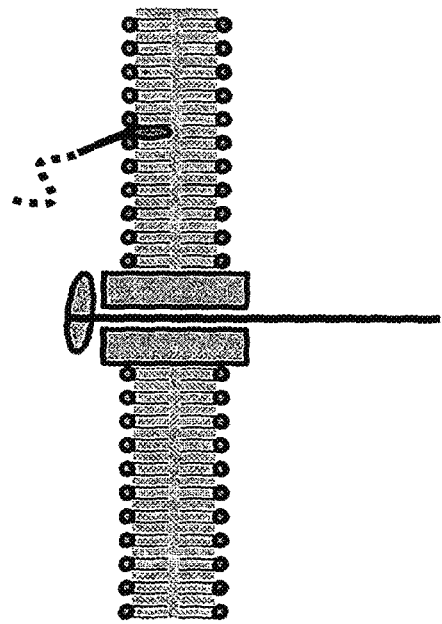
Figure 22D:
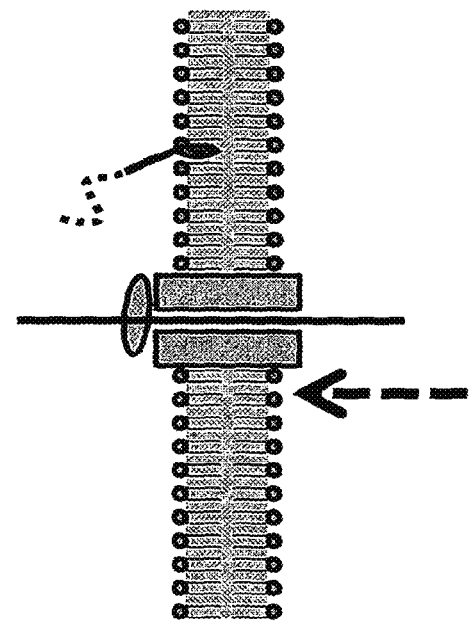

A fourth scheme for tethering analytes to membranes is to use a solid state membrane as a support for a lipid bilayer (FIG. 17D). In this embodiment, the detector element is the nanopore in the solid state membrane. This approach has all the benefits of the examples presented above for lipid membrane tethering. If the surface is rendered hydrophilic, lipid bilayers will self assemble on the surface—an effect which is common for bilayers formed on glass surfaces (Cremer supra). For all the examples above, the solid state nanopore can be combined with a polynucleotide binding protein to form the detector.

Example 5

This Example describes how helicase-controlled DNA movement was not observed for non-tethered DNA when exposed to an MspA nanopore embedded in a tri-block co-polymer. The chip has 128 wells with platinum electrodes and an aperture of 30 μm with a platinum common electrode attached to the cap.

The monolayers were formed with a solution mixture of 50 mg/ml tri-block co-polymer (TBCP 6-33-6, OH-PMOXA-(PEG linker)-PDMS-(PEG Linker)-PMOXA-OH, Polymer Source Product ID: P3691B-MOXZDMS-MOXZ) in oil. The nanopore (MS-(G75S/G77S/L88N/D90N/D91N/D93N/D118R/Q126R/D134R/E139K)8) was then added to the chip in the buffer. Reagents were only added across the top of the chip (cis side) once the chip was formed.

The experiment were carried out with 625 mM sodium chloride, 25 mM potassium ferricyanide, 75 mM potassium ferrocyanide, 100 mM HEPES, pH 8.0 (buffer 1). The MspA mutant used was MS-(G75S/G77S/L88N/D90N/D91N/D93N/D118R/Q126R/D134R/E139K)8. The DNA sequence used in this experiment was a double-stranded 400 mer strand (SEQ ID NO: 39 shows the sequence of the sense strand).

```
                                      SEQ ID NO: 39
TTTTTTTTTTTTTTTTTTTTTTTTTTTTTTTTTTTTTTTTTTTTTTTT

GGTTGTTTCTGTTGGTGCTGATATTGCGCTCCACTAAAGGGCCGATTGAC

CCGGTGGTACCTTGGTTTCTGTTGGTGCTGATATTGCTTTTGATGCCGAC

CCTAAATTTTTGCCTGTTTGGTTCGCTTTGAGTCTTCTTCGGTTCCGAC

TACCCTCCCGACTGCCTATGATGTTTATCCTTTGGATGGTCGCCATGATG

GTGGTTATTATACCGTCAAGGACTGTGTGACTATTGACGTCCTTCCCCGT

ACGCCGGGCAATAATGTTTATGTTGGTTTCATGGTTTGGTCTAACTTTAC

CGCTACTAAATGCCGCGGATTGGTTTCGCTGAATCAGGTTATTAAAGAGA

TTATTTGTCTCCAGCCACTTAAGTGAGGTGATTTATGTTTGGTGCTATTG

CTGGCGGTATTGCTTCTGCTCTTGCTGGTGGCGCCATGTCTAAATTGTTT

GGAGGCGGTCGAGCT
```

The monolayer was formed with 50 mg/nil tri-block co-polymer (TBCP 6-33-6, OH-PMOXA-(PEG linker)-PDMS-(PEG Linker)-PMOXA-OH, Polymer Source Product ID: P3691B-MOXZDMSMOXZ) in oil and nanopores (MS-(G75S/G77S/L88N/D90N/D91N/D93N/D118R/Q126R/D134R/E139K)8) pre-inserted on the chip. The chip was then inserted into the blade and the solution manually removed by pipette and re-inserted. Next 1.5 nM DNA (sense strand sequence SEQ ID NO: 39). 500 nM helicase, 10 mM $MgCl_2$ and 1 mM ATP was added to 150 ul of buffer 1. The solution was then pipetted across the chip through the chimney in the cap and left to diffuse to the nanopore. Data was recorded for 1 hour at +120 mV, with a potential flip to 0 mV and then −50 mV every 5 minutes, to obtain helicase events in the nanopore.

Helicase-controlled DNA movement for non-tethered DNA (sense strand sequence SEQ ID NO: 39) through a MS-(G75S/G77S/L88N/D90N/D91N/D93N/D118R/Q126R/D134R/E139K)8 nanopore inserted in a tri-block co-polymer (TBCP 6-33-6, OH-PMOXA-(PEG linker)-PDMS-(PEG Linker)-PMOXA-OH, Polymer Source Product ID: P3691B-MOXZDMSMOXZ) was not detected. The pore was observed to block under the conditions tested but no helicase-controlled DNA movement was noted.

Example 6

This Example describes how helicase-controlled DNA movement wits observed for tethered DNA when exposed to an MspA nanopore embedded in a tri-block co-polymer. The chip has 128 wells with platinum electrodes and an aperture of 30 μm with a platinum common electrode attached to the cap.

The monolayers were formed with a solution mixture of 50 mg/ml tri-block co-polymer (TBCP 6-33-6, OH-PMOXA-(PEG linker)-PDMS-(PEG Linker)-PMOXA-OH, Polymer Source Product ID: P3691B-MOXZDMS-MOXZ) in oil. The nanopore (MS-(G75S/G77S/L88N/D90N/D91N/D93N/D118R/Q126R/D134R/E139K)8) was then added to the chip in the buffer. Reagents were only added across the top of the chip (cis side) once the chip was formed.

The experiment were carried out with 625 mM sodium chloride, 25 mM potassium ferricyanide, 75 mM potassium ferrocyanide, 100 mM HEPES, pH 8.0 (buffer 1). The MspA mutant used was MS-(G75S/G77S/L88N/D90N/D91N/D93N/D118R/Q126R/D134R/E139K)8. The DNA sequence used in this experiment consists of double-stranded 400 mer DNA (SEQ ID NO: 40 shows the sequence of the sense strand) and a short complementary strand of DNA with a cholesterol attached at the 3' end (SEQ ID NO: 41) which can hybridise to a portion of SEQ ID NO: 40.

SEQ ID NO: 40
```
TTTTTTTTTTTTTTTTTTTTTTTTTTTTTTTTTTTTTTTTT
GGTTGTTTCTGTTGGTGCTGATATTGCGCTCCACTAAAGGGCCGATTGAC
GCTCCACTAAAGGGCCGATTGACCCGGTTGTTTCTGTTGGTGCTGATATT
GCTTTTGATGCCGACCCTAAATTTTTGCCTGTTTGGTTCGCTTTGAGTC
TTCTTCGGTTCCGACTACCCTCCCGACTGCCTATGATGTTTATCCTTTGG
ATGGTCGCCATGATGGTGGTTATTATACCGTCAAGGACTGTGTGACTATT
GACGTCCTTCCCCGTACGCCGGGCAATAATGTTTATGTTGGTTTCATGGT
TTGGTCTAACTTTACCGCTACTAAATGCCGCGCATTGGTTTCGCTGAATC
```

-continued
```
AGGTTATTAAAGAGATTATTTGTCTCCAGCCACTTAAGTGAGGTGATTTA
TGTTTGGTGCTATTGCTGGCGGTATTGCTTCTGCTCTTGCTGGTGGCGCC
ATCTCTAAATTGTTTGGAGGCGGTCGAGCT
```

SEQ ID NO: 41
```
AGCGACTAACAAACACAATCTGATGGCTTTTTTTTTTTTTTTTTTTTT
TTTTTTT/3 CholTEG/
```

The monolayer was formed with 50 mg/ml tri-block co-polymer (TBCP 6-33-6, OH-PMOXA-(PEG linker)-PDMS-(PEG Linker)-PMOXA-OH, Polymer Source Product ID: P3691B-MOXZDMSMOXZ) in oil and nanopores pre-inserted on the chip. The chip was then inserted into the blade and the solution manually removed by pipette and re-inserted. Next 1.5 nM DNA (sense strand sequence of SEQ ID NO: 40 and short complementary tether strand SEQ ID NO: 41), 500 nM helicase, 10 mM MgCl₂ and 1 mM ATP was added to 150 ul of buffer 1. The solution was then pipetted across the chip through the chimney in the cap and left to diffuse to the nanopore. Data was recorded for 1 hour at +120 mV, with a potential flip to 0 mV and then −50 mV every 5 minutes, to obtain helicase controlled DNA movement through the nanopore.

Helicase-controlled translocation of tethered DNA (sense strand sequence of SEQ ID NO: 40 and short complementary tether strand SEQ ID NO: 41) through a MS-(G75S/G77S/L88N/D90N/D91N/D93N/D118R/Q126R/D134R/E139K)8 nanopore inserted in a tri-block co-polymer (TBCP 6-33-6. OH-PMOXA-(PEG linker)-PDMS-(PEG Linker)-PMOXA-OH, Polymer Source Product ID: P3691B-MOXZDMSMOXZ) was detected. Twelve helicase-controlled DNA movements were detected during the course of 1, 5 minute positive cycle. The median time between helicase-controlled DNA movements was 0.5 seconds. Therefore, by tethering the DNA to the tri-block co-polymer it is possible to observe helicase-controlled DNA movement which was not detected in a similar experiment using non-tethered DNA (example 5).

The invention claimed is:

1. A method of preparing a double-stranded target polynucleotide for nanopore sequencing, the method comprising:
   (a) obtaining a target polynucleotide;
   (b) hybridizing a primer with a single stranded leader to the target polynucleotide, extending the primer using a polymerase to copy the target polynucleotide;
   (c) providing a membrane in which is present a nanopore that provides a channel through the membrane;
   (d) applying a potential difference across the membrane, wherein the polynucleotide is captured by the nanopore via the leader; and
   (e) measuring one or more characteristics of the target polynucleotide as the target polynucleotide moves through the nanopore.

2. The method of claim 1, wherein (b) is repeated by polymerase chain reaction (PCR).

3. The method of claim 1, wherein the primer comprises a complementary section to the target polynucleotide and a homopolymer section.

4. The method of claim 3, wherein the primer prevents the polymerase from extending beyond the homopolymer section.

5. The method of claim 4, wherein the leader comprises a single-stranded polyT section.

6. The method of claim 1, wherein the membrane is an amphiphilic layer, a lipid bilayer, or a solid state layer.

7. The method of claim 1, further comprises contacting the membrane with the target polynucleotide, wherein the target polynucleotide is tethered to the membrane via an anchor.

8. The method of claim 7, wherein the anchor is a hydrophobic anchor selected from a group consisting of a lipid, a fatty acid, a sterol, a carbon nanotube, and an amino acid.

9. The method of claim 7, wherein the hydrophobic anchor is capable of embedding in the membrane.

10. The method of claim 7, wherein the polynucleotide is tethered transiently to the membrane.

11. The method of claim 1, wherein the target polynucleotide is detected based on ion flow through the nanopore that is measured via an electrical means.

12. The method of claim 1, wherein the polynucleotide is captured by the nanopore via the leader by a DNA handling protein.

13. The method of claim 12, wherein the DNA handling protein is an exonuclease or a polymerase.

14. The method of claim 1, wherein the polynucleotide is detected based on ion flow through the nanopore by measuring a current passing through the nanopore.

15. The method of claim 1, wherein the target polynucleotide is a fragment of genomic DNA.

16. A method for strand sequencing of a double-stranded target polynucleotide, the method comprising:
   (a) obtaining a target polynucleotide;
   (b) hybridizing a primer with a single stranded leader to the target polynucleotide, extending the primer using a polymerase to copy the target polynucleotide;
   (c) providing a membrane in which is present a nanopore that provides a channel through the membrane;
   (d) applying a potential difference across the membrane, wherein the polynucleotide is captured by the nanopore via the leader; and (e) measuring one or more characteristics of the target polynucleotide as the target polynucleotide moves through the nanopore.

17. The method of claim 16, further comprises contacting the membrane with the target polynucleotide, wherein the target polynucleotide is tethered to the membrane via an anchor.

\* \* \* \* \*

SEQUENCE LISTING

<160> NUMBER OF SEQ ID NOS: 41

<210> SEQ ID NO 1
<211> LENGTH: 558
<212> TYPE: DNA
<213> ORGANISM: Artificial sequence
<220> FEATURE:
<223> OTHER INFORMATION: Mycobacterium smegmatis porin A mutant
      (D90N/D91N/D93N/D118R/D134R/E139K)

<400> SEQUENCE: 1

```
atgggtctgg ataatgaact gagcctggtg gacggtcaag atcgtaccct gacggtgcaa        60
caatgggata cctttctgaa tggcgttttt ccgctggatc gtaatcgcct gacccgtgaa       120
tggtttcatt ccggtcgcgc aaaatatatc gtcgcaggcc cgggtgctga cgaattcgaa       180
ggcacgctgg aactgggtta tcagattggc tttccgtggt cactgggcgt tggtatcaac       240
ttctcgtaca ccacgccgaa tattctgatc aacaatggta acattaccgc accgccgttt       300
ggcctgaaca gcgtgattac gccgaacctg tttccgggtg ttagcatctc tgcccgtctg       360
ggcaatggtc cgggcattca agaagtggca acctttagtg tgcgcgtttc cggcgctaaa       420
ggcggtgtcg cggtgtctaa cgcccacggt accgttacgg gcgcggccgg cggtgtcctg       480
ctgcgtccgt tcgcgcgcct gattgcctct accggcgaca gcgttacgac ctatggcgaa       540
```

-continued

```
ccgtggaata tgaactaa                                                    558
```

<210> SEQ ID NO 2
<211> LENGTH: 184
<212> TYPE: PRT
<213> ORGANISM: Artificial sequence
<220> FEATURE:
<223> OTHER INFORMATION: Mycobacterium smegmatis porin A mutant
      (D90N/D91N/D93N/D118R/D134R/E139K)

<400> SEQUENCE: 2

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 3
<211> LENGTH: 882
<212> TYPE: DNA
<213> ORGANISM: Artificial sequence
<220> FEATURE:
<223> OTHER INFORMATION: alpha-hemolysin mutant (M111R)

<400> SEQUENCE: 3

```
atggcagatt ctgatattaa tattaaaacc ggtactacag atattggaag caatactaca    60
gtaaaaacag gtgatttagt cacttatgat aaagaaaatg gcatgcacaa aaaagtattt   120
tatagtttta tcgatgataa aaatcacaat aaaaaactgc tagttattag aacaaaaggt   180
accattgctg gtcaatatag agtttatagc gaagaaggtg ctaacaaaag tggtttagcc   240
tggccttcag ccctttaaggt acagttgcaa ctacctgata tgaagtagc tcaaatatct   300
gattactatc caagaaattc gattgataca aagagtata ggagtacttt aacttatgga   360
ttcaacggta atgttactgg tgatgataca ggaaaaattg gcggccttat tggtgcaaat   420
gtttcgattg tcatacact gaaatatgtt caacctgatt tcaaaacaat tttagagagc   480
ccaactgata aaaagtagg ctggaaagtg atatttaaca atatggtgaa tcaaaattgg   540
ggaccatacg atcgagattc ttggaacccg gtatatggca atcaactttt catgaaaact   600
```

```
agaaatggtt ctatgaaagc agcagataac ttccttgatc ctaacaaagc aagttctcta    660
ttatcttcag ggttttcacc agacttcgct acagttatta ctatggatag aaaagcatcc    720
aaacaacaaa caaatataga tgtaatatac gaacgagttc gtgatgatta ccaattgcat    780
tggacttcaa caaattggaa aggtaccaat actaaagata aatggacaga tcgttcttca    840
gaaagatata aaatcgattg ggaaaaagaa gaaatgacaa at                       882
```

```
<210> SEQ ID NO 4
<211> LENGTH: 293
<212> TYPE: PRT
<213> ORGANISM: Artificial sequence
<220> FEATURE:
<223> OTHER INFORMATION: alpha-hemolysin mutant (M111R)

<400> SEQUENCE: 4
```

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Arg Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```

<210> SEQ ID NO 5
<211> LENGTH: 1830
<212> TYPE: DNA
<213> ORGANISM: bacteriophage phi AR29

<400> SEQUENCE: 5

| | | | | | |
|---|---|---|---|---|---|
| atgaaacaca | tgccgcgtaa | aatgtatagc | tgcgcgtttg | aaaccacgac | caaagtggaa | 60 |
| gattgtcgcg | tttgggccta | tggctacatg | aacatcgaag | atcattctga | atacaaaatc | 120 |
| ggtaacagtc | tggatgaatt | tatggcatgg | gtgctgaaag | ttcaggcgga | tctgtacttc | 180 |
| cacaacctga | aatttgatgg | cgcattcatt | atcaactggc | tggaacgtaa | tggctttaaa | 240 |
| tggagcgcgg | atggtctgcc | gaacacgtat | aataccatta | tctctcgtat | gggccagtgg | 300 |
| tatatgattg | atatctgcct | gggctacaaa | ggtaaacgca | aaattcatac | cgtgatctat | 360 |
| gatagcctga | aaaaactgcc | gtttccggtg | aagaaaattg | cgaaagattt | caaactgacg | 420 |
| gttctgaaag | gcgatattga | ttatcacaaa | gaacgtccgg | ttggttacaa | aatcaccccg | 480 |
| gaagaatacg | catacatcaa | aaacgatatc | cagatcatcg | cagaagcgct | gctgattcag | 540 |
| tttaaacagg | cctggatccg | catgaccgcg | ggcagtgata | gcctgaaagg | tttcaaagat | 600 |
| atcatcacga | ccaaaaaatt | caaaaaagtg | ttcccgacgc | tgagcctggg | tctggataaa | 660 |
| gaagttcgtt | atgcctaccg | cggcggtttt | acctggctga | cgatcgtttc | aaagaaaaa | 720 |
| gaaattggcg | agggtatggt | gtttgatgtt | aatagtctgt | atccggcaca | gatgtacagc | 780 |
| cgcctgctgc | cgtatggcga | accgatcgtg | ttcgagggta | aatatgtttg | ggatgaagat | 840 |
| tacccgctgc | atattcagca | catccgttgt | gaatttgaac | tgaaagaagg | ctatattccg | 900 |
| accattcaga | tcaaacgtag | tcgcttctat | aagggtaacg | aatacctgaa | aagctctggc | 960 |
| ggtgaaatcg | cggatctgtg | gctgagtaac | gtggatctgg | aactgatgaa | agaacactac | 1020 |
| gatctgtaca | acgttgaata | tcatcagcgg | ctgaaattta | aagccacgac | cggtctgttc | 1080 |
| aaagatttca | tcgataaatg | gacctacatc | aaaacgacct | ctgaaggcgc | gattaaacag | 1140 |
| ctggccaaac | tgatgctgaa | cagcctgtat | ggcaaattcg | cctctaatcc | ggatgtgacc | 1200 |
| ggtaaagttc | cgtacctgaa | agaaaatggc | gcactgggtt | ttcgcctggg | cgaagaagaa | 1260 |
| acgaaagatc | cggtgtatac | cccgatgggg | gttttcatta | cggcctgggc | acgttacacg | 1320 |
| accatcaccg | cggcccaggc | atgctatgat | cgcattatct | actgtgatac | cgattctatt | 1380 |
| catctgacgg | gcaccgaaat | cccggatgtg | attaaagata | tcgttgatcc | gaaaaaactg | 1440 |
| ggttattggg | cccacgaaag | tacgtttaaa | cgtgcaaaat | acctgcgcca | gaaaacctac | 1500 |
| atccaggata | tctacatgaa | agaagtggat | ggcaaactgg | ttgaaggttc | tccggatgat | 1560 |
| tacaccgata | tcaaattcag | tgtgaaatgc | gccggcatga | cggataaaat | caaaaaagaa | 1620 |
| gtgacctttg | aaaacttcaa | agttggtttc | agccgcaaaa | tgaaaccgaa | accggtgcag | 1680 |
| gttccgggcg | gtgtggttct | ggtggatgat | acgtttacca | ttaaatctgg | cggtagtgcg | 1740 |
| tggagccatc | cgcagttcga | aaaaggcggt | ggctctggtg | gcggttctgg | cggtagtgcc | 1800 |
| tggagccacc | cgcagtttga | aaaataataa | | | | 1830 |

<210> SEQ ID NO 6
<211> LENGTH: 608
<212> TYPE: PRT
<213> ORGANISM: bacteriophage phi AR29

<400> SEQUENCE: 6

Met Lys His Met Pro Arg Lys Met Tyr Ser Cys Ala Phe Glu Thr Thr
1               5                   10                  15

```
Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
 50                  55                  60

Phe Asp Gly Ala Phe Ile Ile Asn Trp Leu Glu Arg Asn Gly Phe Lys
 65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430
```

```
Ile Thr Ala Trp Ala Arg Tyr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
                565                 570                 575

Gly Gly Ser Ala Trp Ser His Pro Gln Phe Glu Lys Gly Gly Ser
            580                 585                 590

Gly Gly Gly Ser Gly Gly Ser Ala Trp Ser His Pro Gln Phe Glu Lys
    595                 600                 605
```

<210> SEQ ID NO 7
<211> LENGTH: 1458
<212> TYPE: DNA
<213> ORGANISM: Escherichia coli

<400> SEQUENCE: 7

```
atgatgaacg atggcaaaca gcagagcacc ttcctgtttc atgattatga aaccttcggt      60
acccatccgg ccctggatcg tccggcgcag tttgcggcca ttcgcaccga tagcgaattc     120
aatgtgattg gcgaaccgga agtgttttat tgcaaaccgg ccgatgatta tctgccgcag     180
ccgggtgcgg tgctgattac cggtattacc ccgcaggaag cgcgcgcgaa aggtgaaaac     240
gaagcggcgt tgccgcgcg cattcatagc ctgtttaccg tgccgaaaac ctgcattctg     300
ggctataaca tgtgcgcttc gatgatgaa gttacccgta atatcttta tcgtaacttt      360
tatgatccgt atgcgtggag ctggcagcat gataacagcc gttgggatct gctggatgtg     420
atgcgcgcgt gctatgcgct cgcccggaa ggcattaatt ggccggaaaa cgatgatggc     480
ctgccgagct ttcgtctgga acatctgacc aaagccaacg cattgaaca tagcaatgcc     540
catgatgcga tggccgatgt ttatgcgacc attgcgatgg cgaaactggt taaaacccgt     600
cagccgcgcc tgtttgatta tctgtttacc accgtaaca aacacaaact gatggcgctg     660
attgatgttc gcagatgaa accgctggtg catgtgagcg gcatgtttgg cgcctggcgc     720
ggcaacacca gctgggtggc cccgctgccc tggcacccgg aaaatcgtaa cgccgtgatt     780
atggttgatc tggccggtga tattagcccg ctgctggaac tggatagcga taccctgcgt     840
gaacgcctgt ataccgccaa aaccgatctg gccgataatg ccgccgtgcc ggtgaaactg     900
gttcacatta caaatgccc ggtgctggcc caggcgaaca ccctgcgccc ggaagatgcg     960
gatcgtctgg gtattaatcg ccagcattgt ctggataatc tgaaaatcct gcgtgaaaac    1020
ccgcaggtgc gtgaaaaagt ggtggcgatc ttcgcggaag cggaaccgtt caccccgagc    1080
gataacgtgg atgcgcagct gtataacggc ttctttagcg atgccgatcg cgcggcgatg    1140
```

```
aaaatcgttc tggaaaccga accgcgcaat ctgccggcgc tggatattac ctttgttgat    1200
aaacgtattg aaaaactgct gtttaattat cgtgcgcgca attttccggg taccctggat    1260
tatgccgaac agcagcgttg gctggaacat cgtcgtcagg ttttcacccc ggaatttctg    1320
cagggttatg cggatgaact gcagatgctg gttcagcagt atgccgatga taaagaaaaa    1380
gtggcgctgc tgaaagcgct gtggcagtat gcggaagaaa tcgtttctgg ctctggtcac    1440
catcatcatc accactaa                                                  1458
```

```
<210> SEQ ID NO 8
<211> LENGTH: 485
<212> TYPE: PRT
<213> ORGANISM: Escherichia coli

<400> SEQUENCE: 8
```

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110

Arg Asn Ile Phe Tyr Arg Asn Phe Tyr Asp Pro Tyr Ala Trp Ser Trp
        115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Cys Pro Val Leu Ala Gln Ala Asn Thr Leu Arg Pro Glu Asp Ala
305                 310                 315                 320
```

```
Asp Arg Leu Gly Ile Asn Arg Gln His Cys Leu Asp Asn Leu Lys Ile
            325                 330                 335
Leu Arg Glu Asn Pro Gln Val Arg Glu Lys Val Val Ala Ile Phe Ala
        340                 345                 350
Glu Ala Glu Pro Phe Thr Pro Ser Asp Asn Val Asp Ala Gln Leu Tyr
    355                 360                 365
Asn Gly Phe Phe Ser Asp Ala Asp Arg Ala Ala Met Lys Ile Val Leu
370                 375                 380
Glu Thr Glu Pro Arg Asn Leu Pro Ala Leu Asp Ile Thr Phe Val Asp
385                 390                 395                 400
Lys Arg Ile Glu Lys Leu Leu Phe Asn Tyr Arg Ala Arg Asn Phe Pro
                405                 410                 415
Gly Thr Leu Asp Tyr Ala Glu Gln Gln Arg Trp Leu Glu His Arg Arg
            420                 425                 430
Gln Val Phe Thr Pro Glu Phe Leu Gly Tyr Ala Asp Glu Leu Gln
        435                 440                 445
Met Leu Val Gln Gln Tyr Ala Asp Asp Lys Glu Lys Val Ala Leu Leu
    450                 455                 460
Lys Ala Leu Trp Gln Tyr Ala Glu Glu Ile Val Ser Gly Ser Gly His
465                 470                 475                 480
His His His His His
            485

<210> SEQ ID NO 9
<211> LENGTH: 804
<212> TYPE: DNA
<213> ORGANISM: Escherichia coli

<400> SEQUENCE: 9
atgaaatttg ttagcttcaa tatcaacggc ctgcgcgcgc gcccgcatca gctggaagcg      60
attgtggaaa acatcagcc ggatgttatt ggtctgcagg aaaccaaagt tcacgatgat     120 atgttccgc tggaagaagt ggcgaaactg gctataacg tgttttatca tggccagaaa     180
ggtcattatg gcgtggccct gctgaccaaa gaaaccccga tcgcggttcg tcgtggtttt     240
ccgggtgatg atgaagaagc gcagcgtcgt attattatgg cggaaattcc gagcctgctg     300
ggcaatgtga ccgttattaa cggctatttt ccgcagggcg aaagccgtga tcatccgatt     360
aaatttccgg ccaaagcgca gttctatcag aacctgcaga actatctgga aaccgaactg     420
aaacgtgata tccgggtgct gatcatgggc gatatgaaca ttagcccgac cgatctggat     480
attggcattg gcgaagaaaa ccgtaaacgc tggctgcgta ccggtaaatg cagctttctg     540
ccggaagaac gtaatggat ggatcgcctg atgagctggg gcctggtgga tacctttcgt     600
catgcgaacc cgcagaccgc cgatcgcttt agctggtttg attatcgcag caaaggtttt     660
gatgataacc gtggcctgcg cattgatctg ctgctggcga gccagccgct ggcggaatgc     720
tgcgttgaaa ccggtattga ttatgaaatt cgcagcatgg aaaaaccgag cgatcacgcc     780
ccggtgtggg cgacctttcg ccgc                                           804

<210> SEQ ID NO 10
<211> LENGTH: 268
<212> TYPE: PRT
<213> ORGANISM: Escherichia coli

<400> SEQUENCE: 10

Met Lys Phe Val Ser Phe Asn Ile Asn Gly Leu Arg Ala Arg Pro His
```

```
           1               5                  10                 15
           Gln Leu Glu Ala Ile Val Glu Lys His Gln Pro Asp Val Ile Gly Leu
                          20                 25                 30
           Gln Glu Thr Lys Val His Asp Asp Met Phe Pro Leu Glu Glu Val Ala
                          35                 40                 45
           Lys Leu Gly Tyr Asn Val Phe Tyr His Gly Gln Lys Gly His Tyr Gly
                          50                 55                 60
           Val Ala Leu Leu Thr Lys Glu Thr Pro Ile Ala Val Arg Arg Gly Phe
           65                 70                 75                 80
           Pro Gly Asp Asp Glu Glu Ala Gln Arg Arg Ile Ile Met Ala Glu Ile
                                  85                 90                 95
           Pro Ser Leu Leu Gly Asn Val Thr Val Ile Asn Gly Tyr Phe Pro Gln
                          100                105                110
           Gly Glu Ser Arg Asp His Pro Ile Lys Phe Pro Ala Lys Ala Gln Phe
                          115                120                125
           Tyr Gln Asn Leu Gln Asn Tyr Leu Glu Thr Glu Leu Lys Arg Asp Asn
                          130                135                140
           Pro Val Leu Ile Met Gly Asp Met Asn Ile Ser Pro Thr Asp Leu Asp
           145                150                155                160
           Ile Gly Ile Gly Glu Glu Asn Arg Lys Arg Trp Leu Arg Thr Gly Lys
                                  165                170                175
           Cys Ser Phe Leu Pro Glu Glu Arg Glu Trp Met Asp Arg Leu Met Ser
                          180                185                190
           Trp Gly Leu Val Asp Thr Phe Arg His Ala Asn Pro Gln Thr Ala Asp
                          195                200                205
           Arg Phe Ser Trp Phe Asp Tyr Arg Ser Lys Gly Phe Asp Asp Asn Arg
                          210                215                220
           Gly Leu Arg Ile Asp Leu Leu Ala Ser Gln Pro Leu Ala Glu Cys
           225                230                235                240
           Cys Val Glu Thr Gly Ile Asp Tyr Glu Ile Arg Ser Met Glu Lys Pro
                                  245                250                255
           Ser Asp His Ala Pro Val Trp Ala Thr Phe Arg Arg
                          260                265

<210> SEQ ID NO 11
<211> LENGTH: 2000
<212> TYPE: DNA
<213> ORGANISM: Thermus thermophilus

<400> SEQUENCE: 11
atgcgtgatc gtgtccgctg gcgtgttctg tccctgccgc cgctggctca atggcgtgaa     60
gttatggctg ccctggaagt gggtccggaa gcggccctgg catattggca ccgcggtttt    120
cgtcgcaaag aagatctgga cccgccgctg gccctgctgc gctgaaaagg cctgcgcgaa    180
gcagctgcgc tgctggaaga agccctgcgt cagggtaaac gtattcgcgt tcatggcgat    240
tatgacgccg atggcctgac cggtaccgca attctggtcc gtggtctggc ggcactgggt    300
gccgatgtgc atccgtttat tccgcaccgc ctggaagaag ctacggtgt gctgatggaa    360 cgtgttccgg aacacctgga agcgagcgac ctgttcctga cggtggattg cggtatcacc    420
aaccatgccg aactgcgtga actgctggaa atggcgttg aagtcattgt gaccgatcat    480 cacacccccgg gtaaaacccc gtctccgggc ctggtggttc accggcgct gacgccggat    540 ctgaaagaaa aaccgaccgg cgctggtgtc gtgtttctgc tgctgtgggc actgcacgaa    600
cgtctgggtc tgccgccgcc gctggaatat gccgacctgg ctgccgttgg taccattgcc    660
```

```
gatgttgccc cgctgtgggg ttggaaccgt gcactggtga agaaggcct ggcacgtatt      720 ccggctagct cttgggttgg tctgcgtctg ctggccgaag cagtcggcta caccggtaaa     780
gcggttgaag tcgccttccg tattgcaccg cgcatcaacg ccgcatcacg cctgggtgaa     840
gcagaaaaag ctctgcgtct gctgctgacg gatgacgctg cggaagctca ggcgctggtt     900
ggcgaactgc accgcctgaa tgctcgtcgc cagaccctgg aagaagcgat gctgcgtaaa     960
ctgctgccgc aagcggaccc ggaagccaaa gcaatcgtgc tgctggatcc ggaaggccat    1020
ccgggtgtta tgggcattgt cgcttcacgc atcctggaag cgacgctgcg tccggtcttt    1080
ctggtggcgc agggtaaagg taccgtgcgc agcctggcac cgatttctgc cgttgaagcc    1140
ctgcgtagcg ccgaagacct gctgctgcgt tatggcggtc acaaagaagc cgcaggcttt    1200
gctatggatg aagcgctgtt ccggcattc aaagctcgcg ttgaagccta cgctgccgt     1260 ttcccggacc cggttcgtga agtcgcactg ctggatctgc tgccggaacc gggtctgctg    1320
ccgcaggtgt ttcgtgaact ggcgctgctg aaccgtatg gcgaaggtaa tccggaaccg    1380
ctgtttctgc tgtttggtgc accggaagaa gcacgtcgcc tgggtgaagg tcgtcacctg    1440
gcattccgcc tgaaaggtgt gcgtgttctg gcttggaaac agggtgatct ggccctgccg    1500
ccggaagttg aagtggcagg tctgctgtcc gaaaacgcat ggaatggcca tctggcctat    1560
gaagtgcaag cagttgatct gcgtaaaccg gaagcgctgg aaggcggtat tgccccgttt    1620
gcatatccgc tgccgctgct ggaagctctg gcccgtgccc gctgggcga aggtgtttat    1680 gtcccggaag acaacccgga aggtctggat tacgcacgca agctggctt ccgtctgctg    1740 ccgccggaag aagcgggtct gtggctgggt ctgccgccgc gccggtgct gggtcgtcgc    1800 gtggaagttg cactgggccg tgaagcacgt gctcgcctga gtgcaccgcc ggttctgcat    1860
accccggaag ctcgcctgaa agcgctggtg caccgtcgcc tgctgtttgc ctatgaacgt    1920
cgccatccgg gtctgttctc cgaagcgctg ctggcctact gggaagtcaa tcgtgttcag    1980
gaaccggcgg gtagtcctaa                                                2000

<210> SEQ ID NO 12
<211> LENGTH: 666
<212> TYPE: PRT
<213> ORGANISM: Thermus thermophilus

<400> SEQUENCE: 12

Met Arg Asp Arg Val Arg Trp Arg Val Leu Ser Leu Pro Pro Leu Ala
1               5                   10                  15

Gln Trp Arg Glu Val Met Ala Ala Leu Glu Val Gly Pro Glu Ala Ala
            20                  25                  30

Leu Ala Tyr Trp His Arg Gly Phe Arg Arg Lys Glu Asp Leu Asp Pro
        35                  40                  45

Pro Leu Ala Leu Leu Pro Leu Lys Gly Leu Arg Glu Ala Ala Ala Leu
    50                  55                  60

Leu Glu Glu Ala Leu Arg Gln Gly Lys Arg Ile Arg Val His Gly Asp
65                  70                  75                  80

Tyr Asp Ala Asp Gly Leu Thr Gly Thr Ala Ile Leu Val Arg Gly Leu
                85                  90                  95

Ala Ala Leu Gly Ala Asp Val His Pro Phe Ile Pro His Arg Leu Glu
            100                 105                 110

Glu Gly Tyr Gly Val Leu Met Glu Arg Val Pro Glu His Leu Glu Ala
        115                 120                 125
```

Ser Asp Leu Phe Leu Thr Val Asp Cys Gly Ile Thr Asn His Ala Glu
130                 135                 140

Leu Arg Glu Leu Leu Glu Asn Gly Val Glu Val Ile Val Thr Asp His
145                 150                 155                 160

His Thr Pro Gly Lys Thr Pro Ser Pro Gly Leu Val Val His Pro Ala
            165                 170                 175

Leu Thr Pro Asp Leu Lys Glu Lys Pro Thr Gly Ala Gly Val Val Phe
            180                 185                 190

Leu Leu Leu Trp Ala Leu His Glu Arg Leu Gly Leu Pro Pro Pro Leu
            195                 200                 205

Glu Tyr Ala Asp Leu Ala Ala Val Gly Thr Ile Ala Asp Val Ala Pro
210                 215                 220

Leu Trp Gly Trp Asn Arg Ala Leu Val Lys Glu Gly Leu Ala Arg Ile
225                 230                 235                 240

Pro Ala Ser Ser Trp Val Gly Leu Arg Leu Leu Ala Glu Ala Val Gly
                245                 250                 255

Tyr Thr Gly Lys Ala Val Glu Val Ala Phe Arg Ile Ala Pro Arg Ile
            260                 265                 270

Asn Ala Ala Ser Arg Leu Gly Glu Ala Glu Lys Ala Leu Arg Leu Leu
            275                 280                 285

Leu Thr Asp Asp Ala Ala Glu Ala Gln Ala Leu Val Gly Glu Leu His
            290                 295                 300

Arg Leu Asn Ala Arg Arg Gln Thr Leu Glu Glu Ala Met Leu Arg Lys
305                 310                 315                 320

Leu Leu Pro Gln Ala Asp Pro Glu Ala Lys Ala Ile Val Leu Leu Asp
                325                 330                 335

Pro Glu Gly His Pro Gly Val Met Gly Ile Val Ala Ser Arg Ile Leu
            340                 345                 350

Glu Ala Thr Leu Arg Pro Val Phe Leu Val Ala Gln Gly Lys Gly Thr
            355                 360                 365

Val Arg Ser Leu Ala Pro Ile Ser Ala Val Glu Ala Leu Arg Ser Ala
            370                 375                 380

Glu Asp Leu Leu Leu Arg Tyr Gly Gly His Lys Glu Ala Ala Gly Phe
385                 390                 395                 400

Ala Met Asp Glu Ala Leu Phe Pro Ala Phe Lys Ala Arg Val Glu Ala
                405                 410                 415

Tyr Ala Ala Arg Phe Pro Asp Pro Val Arg Glu Val Ala Leu Leu Asp
            420                 425                 430

Leu Leu Pro Glu Pro Gly Leu Leu Pro Gln Val Phe Arg Glu Leu Ala
            435                 440                 445

Leu Leu Glu Pro Tyr Gly Glu Gly Asn Pro Glu Pro Leu Phe Leu Leu
            450                 455                 460

Phe Gly Ala Pro Glu Glu Ala Arg Arg Leu Gly Glu Gly Arg His Leu
465                 470                 475                 480

Ala Phe Arg Leu Lys Gly Val Arg Val Leu Ala Trp Lys Gln Gly Asp
                485                 490                 495

Leu Ala Leu Pro Pro Glu Val Glu Val Ala Gly Leu Leu Ser Glu Asn
            500                 505                 510

Ala Trp Asn Gly His Leu Ala Tyr Glu Val Gln Ala Val Asp Leu Arg
            515                 520                 525

Lys Pro Glu Ala Leu Gly Gly Ile Ala Pro Phe Ala Tyr Pro Leu
            530                 535                 540

Pro Leu Leu Glu Ala Leu Ala Arg Ala Arg Leu Gly Glu Gly Val Tyr

```
                545                 550                 555                 560
Val Pro Glu Asp Asn Pro Glu Gly Leu Asp Tyr Ala Arg Lys Ala Gly
                    565                 570                 575

Phe Arg Leu Leu Pro Pro Glu Glu Ala Gly Leu Trp Leu Gly Leu Pro
                580                 585                 590

Pro Arg Pro Val Leu Gly Arg Arg Val Glu Val Ala Leu Gly Arg Glu
                    595                 600                 605

Ala Arg Ala Arg Leu Ser Ala Pro Pro Val Leu His Thr Pro Glu Ala
                610                 615                 620

Arg Leu Lys Ala Leu Val His Arg Arg Leu Leu Phe Ala Tyr Glu Arg
625                 630                 635                 640

Arg His Pro Gly Leu Phe Ser Glu Ala Leu Leu Ala Tyr Trp Glu Val
                    645                 650                 655

Asn Arg Val Gln Glu Pro Ala Gly Ser Pro
                660                 665

<210> SEQ ID NO 13
<211> LENGTH: 681
<212> TYPE: DNA
<213> ORGANISM: Bacteriophage lambda

<400> SEQUENCE: 13
atgacaccgg acattatcct gcagcgtacc gggatcgatg tgagagctgt cgaacagggg      60
gatgatgcgt ggcacaaatt acggctcggc gtcatcaccg cttcagaagt tcacaacgtg     120
atagcaaaac cccgctccgg aaagaagtgg cctgacatga aaatgtccta cttccacacc     180
ctgcttgctg aggtttgcac cggtgtggct ccggaagtta acgctaaagc actggcctgg     240
ggaaaacagt acgagaacga cgccagaacc ctgtttgaat tcacttccgg cgtgaatgtt     300
actgaatccc cgatcatcta tcgcgacgaa agtatgcgta ccgcctgctc tcccgatggt     360
ttatgcagtg acggcaacgg ccttgaactg aaatgcccgt ttacctcccg ggatttcatg     420
aagttccggc tcggtggttt cgaggccata aagtcagctt acatggccca ggtgcagtac     480
agcatgtggg tgacgcgaaa aaatgcctgg tactttgcca actatgaccc gcgtatgaag     540
cgtgaaggcc tgcattatgt cgtgattgag cgggatgaaa agtacatggc gagttttgac     600
gagatcgtgc cggagttcat cgaaaaaatg gacgaggcac tggctgaaat tggttttgta     660
tttggggagc aatggcgata a                                                681

<210> SEQ ID NO 14
<211> LENGTH: 226
<212> TYPE: PRT
<213> ORGANISM: Bacteriophage lambda

<400> SEQUENCE: 14

Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
                20                  25                  30

Thr Ala Ser Glu Val His Asn Val Ile Ala Lys Pro Arg Ser Gly Lys
            35                  40                  45

Lys Trp Pro Asp Met Lys Met Ser Tyr Phe His Thr Leu Leu Ala Glu
        50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
```

```
                    85                  90                  95
Gly Val Asn Val Thr Glu Ser Pro Ile Ile Tyr Arg Asp Glu Ser Met
                100                 105                 110
Arg Thr Ala Cys Ser Pro Asp Gly Leu Cys Ser Asp Gly Asn Gly Leu
                115                 120                 125
Glu Leu Lys Cys Pro Phe Thr Ser Arg Asp Phe Met Lys Phe Arg Leu
            130                 135                 140
Gly Gly Phe Glu Ala Ile Lys Ser Ala Tyr Met Ala Gln Val Gln Tyr
145                 150                 155                 160
Ser Met Trp Val Thr Arg Lys Asn Ala Trp Tyr Phe Ala Asn Tyr Asp
                165                 170                 175
Pro Arg Met Lys Arg Glu Gly Leu His Tyr Val Val Ile Glu Arg Asp
                180                 185                 190
Glu Lys Tyr Met Ala Ser Phe Asp Glu Ile Val Pro Glu Phe Ile Glu
                195                 200                 205
Lys Met Asp Glu Ala Leu Ala Glu Ile Gly Phe Val Phe Gly Glu Gln
            210                 215                 220
Trp Arg
225

<210> SEQ ID NO 15
<211> LENGTH: 184
<212> TYPE: PRT
<213> ORGANISM: Mycobacterium smegmatis

<400> SEQUENCE: 15

Gly Leu Asp Asn Glu Leu Ser Leu Val Asp Gly Gln Asp Arg Thr Leu
1               5                   10                  15
Thr Val Gln Gln Trp Asp Thr Phe Leu Asn Gly Val Phe Pro Leu Asp
                20                  25                  30
Arg Asn Arg Leu Thr Arg Glu Trp Phe His Ser Gly Arg Ala Lys Tyr
            35                  40                  45
Ile Val Ala Gly Pro Gly Ala Asp Glu Phe Glu Gly Thr Leu Glu Leu
        50                  55                  60
Gly Tyr Gln Ile Gly Phe Pro Trp Ser Leu Gly Val Gly Ile Asn Phe
65                  70                  75                  80
Ser Tyr Thr Thr Pro Asn Ile Leu Ile Asp Asp Gly Asp Ile Thr Ala
                85                  90                  95
Pro Pro Phe Gly Leu Asn Ser Val Ile Thr Pro Asn Leu Phe Pro Gly
                100                 105                 110
Val Ser Ile Ser Ala Asp Leu Gly Asn Gly Pro Gly Ile Gln Glu Val
                115                 120                 125
Ala Thr Phe Ser Val Asp Val Ser Gly Pro Ala Gly Gly Val Ala Val
            130                 135                 140
Ser Asn Ala His Gly Thr Val Thr Gly Ala Ala Gly Gly Val Leu Leu
145                 150                 155                 160
Arg Pro Phe Ala Arg Leu Ile Ala Ser Thr Gly Asp Ser Val Thr Thr
                165                 170                 175
Tyr Gly Glu Pro Trp Asn Met Asn
            180

<210> SEQ ID NO 16
<211> LENGTH: 184
<212> TYPE: PRT
<213> ORGANISM: Mycobacterium smegmatis
```

<400> SEQUENCE: 16

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
            115                 120                 125

Ala Thr Phe Ser Val Asp Val Ser Gly Pro Ala Gly Val Ala Val
            130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 17
<211> LENGTH: 183
<212> TYPE: PRT
<213> ORGANISM: Mycobacterium smegmatis

<400> SEQUENCE: 17

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
            115                 120                 125

Thr Phe Ser Val Asp Val Lys Gly Ala Lys Gly Ala Val Ala Val Ser
            130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
        180

<210> SEQ ID NO 18
<211> LENGTH: 70
<212> TYPE: DNA
<213> ORGANISM: Artificial sequence
<220> FEATURE:
<223> OTHER INFORMATION: Synthesised sequence used in the examples

<400> SEQUENCE: 18 ttttttttttt tttttttttt tttttttttt tttttttttt tttttttttt tttttttttt    60
tttttttttt                                                            70

<210> SEQ ID NO 19
<211> LENGTH: 70
<212> TYPE: DNA
<213> ORGANISM: Artificial Sequence
<220> FEATURE:
<223> OTHER INFORMATION: Synthesised sequence used in the examples

<400> SEQUENCE: 19
aaaaaaaaaa aaaaaaaaaa aaaaaaaaaa aaaaaaaaaa aaaaaaaaaa aaaaaaaaaa    60
aaaaaaaaaa                                                            70

<210> SEQ ID NO 20
<211> LENGTH: 70
<212> TYPE: DNA
<213> ORGANISM: Artificial Sequence
<220> FEATURE:
<223> OTHER INFORMATION: Synthesised sequence used in the examples

<400> SEQUENCE: 20
cccccccccc cccccccccc cccccccccc cccccccccc cccccccccc cccccccccc    60
cccccccccc                                                            70

<210> SEQ ID NO 21
<211> LENGTH: 70
<212> TYPE: DNA
<213> ORGANISM: Artificial Sequence
<220> FEATURE:
<223> OTHER INFORMATION: Synthesised sequence used in the examples

<400> SEQUENCE: 21
tgtgttctat gtcttattct tacttcgtta ttcttgtctc tattctgttt atgtttcttg    60
tttgttagca                                                            70

<210> SEQ ID NO 22
<211> LENGTH: 93
<212> TYPE: DNA
<213> ORGANISM: Artificial Sequence
<220> FEATURE:
<223> OTHER INFORMATION: Synthesised sequence used in the examples

<400> SEQUENCE: 22
tttttttttt tttttttttt tttttttttt tttttttttt tttttttttt tttttttttt    60
tttttttttt ggctacgacc tgcatgagaa tgc                                  93

<210> SEQ ID NO 23
<211> LENGTH: 79
<212> TYPE: DNA
<213> ORGANISM: Artificial Sequence
<220> FEATURE:

<223> OTHER INFORMATION: Synthesised sequence used in the examples

<400> SEQUENCE: 23
ctcacctatc cttccactca cccccccaaaa aaccccccaa aaaacccccc aaaaaagcat    60
tctcatgcag gtcgtagcc                                                  79

<210> SEQ ID NO 24
<211> LENGTH: 100
<212> TYPE: DNA
<213> ORGANISM: Artificial Sequence
<220> FEATURE:
<223> OTHER INFORMATION: Synthesised sequence used in the examples

<400> SEQUENCE: 24 aaccccccaaa aaccccccaaa aaccccccaaa aaccccccaaa aaccccccaaa aaccccccaaa    60 aaccccccaaa aaccccccata gagacaagaa taacgaagta                        100

<210> SEQ ID NO 25
<211> LENGTH: 23
<212> TYPE: DNA
<213> ORGANISM: Artificial Sequence
<220> FEATURE:
<223> OTHER INFORMATION: Synthesised sequence used in the examples

<400> SEQUENCE: 25
tacttcgtta ttcttgtctc tat                                            23

<210> SEQ ID NO 26
<211> LENGTH: 65
<212> TYPE: DNA
<213> ORGANISM: Artificial Sequence
<220> FEATURE:
<223> OTHER INFORMATION: Synthesised sequence used in the examples

<400> SEQUENCE: 26 ccccccccccc cccccacccc cccccccccc ccccctattc tgtttatgtt tcttgtttgt    60
tagcc                                                                65

<210> SEQ ID NO 27
<211> LENGTH: 31
<212> TYPE: DNA
<213> ORGANISM: Artificial Sequence
<220> FEATURE:
<223> OTHER INFORMATION: Synthesised sequence used in the examples

<400> SEQUENCE: 27
ggctaacaaa caagaaacat aaacagaata g                                   31

<210> SEQ ID NO 28
<211> LENGTH: 65
<212> TYPE: DNA
<213> ORGANISM: Artificial sequence
<220> FEATURE:
<223> OTHER INFORMATION: Synthesised sequence used in the examples

<400> SEQUENCE: 28 ccccccccccc cccccacccc cccccccccc ccccctattc tgtttatgtt tcttgtttgt    60
tagcc                                                                65

<210> SEQ ID NO 29

<400> SEQUENCE: 29

<210> SEQ ID NO 30
<211> LENGTH: 27
<212> TYPE: DNA
<213> ORGANISM: Artificial Sequence
<220> FEATURE:
<223> OTHER INFORMATION: Synthesised sequence used in examples

<400> SEQUENCE: 30
gttagaccaa accatgaaac caacata                                           27

<210> SEQ ID NO 31
<211> LENGTH: 24
<212> TYPE: DNA
<213> ORGANISM: Artificial Sequence
<220> FEATURE:
<223> OTHER INFORMATION: Synthesised sequence used in examples

<400> SEQUENCE: 31
gaccgcctcc aaacaattta gaca                                              24

<210> SEQ ID NO 32
<211> LENGTH: 24
<212> TYPE: DNA
<213> ORGANISM: Artificial Sequence
<220> FEATURE:
<223> OTHER INFORMATION: Synthesised sequence used in the examples

<400> SEQUENCE: 32
ggcaatctct ttctgattgt ccag                                              24

<210> SEQ ID NO 33
<211> LENGTH: 885
<212> TYPE: DNA
<213> ORGANISM: Artificial sequence
<220> FEATURE:
<223> OTHER INFORMATION: sequence for one subunit of alpha-HL-Q

<400> SEQUENCE: 33
atggcagatt ctgatattaa tattaaaacc ggtactacag atattggaag caatactaca        60
gtaaaaacag gtgatttagt cacttatgat aaagaaaatg gcatgcacaa aaaagtattt       120
tatagtttta tcgatgataa aaatcacaat aaaaaaactgc tagttattag aacaaaaggt      180
accattgctg gtcaatatag agtttatagc gaagaaggtg ctaacaaaag tggtttagcc       240
tggccttcag cctttaaggt acagttgcaa ctacctgata tgaagtagc tcaaatatct        300 gattactatc caagaaattc gattgataca aaagagtata tgagtacttt aacttatgga       360
ttcaacggta atgttactgg tgatgataca ggaaaaattg gcggccttat tggtgcacaa       420
gtttcgattg gtcatacact gaaatatgtt caacctgatt tcaaaacaat tttagagagc       480
ccaactgata aaaagtagg ctggaaagtg atatttaaca atatggtgaa tcaaaattgg        540
ggaccatacg atcgagattc ttggaacccg gtatatggca atcaactttt catgaaaact       600
agaaatggtt ctatgaaagc agcagataac ttccttgatc ctaacaaagc aagttctcta       660
ttatcttcag ggttttcacc agacttcgct acagttatta ctatggatag aaaagcatcc       720
aaacaacaaa caaatataga tgtaatatac gaacgagttc gtgatgatta ccaattgcat       780
tggacttcaa caaattggaa aggtaccaat actaaagata atggacaga tcgttcttca       840 gaaagatata aaatcgattg ggaaaaagaa gaaatgacaa attaa                       885

```
<210> SEQ ID NO 34
<211> LENGTH: 293
<212> TYPE: PRT
<213> ORGANISM: Artificial Sequence
<220> FEATURE:
<223> OTHER INFORMATION: protein sequence for one subunit of alpha-HL-Q

<400> SEQUENCE: 34

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Gln Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 35
<211> LENGTH: 957
<212> TYPE: DNA
<213> ORGANISM: Artificial Sequence
<220> FEATURE:
<223> OTHER INFORMATION: polynucleotide sequence of one subunit of
      alpha-HL-E287C-QC-D5FLAG

<400> SEQUENCE: 35
atggcagatt ctgatattaa tattaaaacc ggtactacag atattggaag caatactaca      60
```

```
gtaaaaacag gtgatttagt cacttatgat aaagaaaatg gcatgcacaa aaagtatttt    120 tatagttta tcgatgataa aaatcacaat aaaaaactgc tagttattag aacaaaaggt    180
accattgctg gtcaatatag agtttatagc gaagaaggtg ctaacaaaag tggtttagcc    240
tggccttcag cctttaaggt acagttgcaa ctacctgata atgaagtagc tcaaatatct    300
gattactatc caagaaattc gattgataca aaagagtata tgagtacttt aacttatgga    360
ttcaacggta atgttactgg tgatgataca ggaaaaattg gcggctgtat tggtgcacaa    420
gtttcgattg gtcatacact gaaatatgtt caacctgatt tcaaaacaat tttagagagc    480
ccaactgata aaaagtagg ctggaaagtg atatttaaca atatggtgaa tcaaaattgg    540
ggaccatacg atcgagattc ttggaacccg gtatatggca atcaactttt catgaaaact    600
agaaatggtt ctatgaaagc agcagataac ttccttgatc ctaacaaagc aagttctcta    660
ttatcttcag ggttttcacc agacttcgct acagttatta ctatggatag aaaagcatcc    720
aaacaacaaa caaatataga gtaatatac gaacgagttc gtgatgatta ccaattgcat    780
tggacttcaa caaattggaa aggtaccaat actaaagata aatggacaga tcgttcttca    840
gaaagatata aaatcgattg gtgcaaagaa gaaatgacaa atgatgatga tgatgatagc    900
ggcagcggtg attataaaga tgatgatgat aaagcgcacc atcatcatca ccactaa    957

<210> SEQ ID NO 36
<211> LENGTH: 317
<212> TYPE: PRT
<213> ORGANISM: Artificial Sequence
<220> FEATURE:
<223> OTHER INFORMATION: amino acid sequence of one subunit of alpha-HL-
      E287C-QC-D5FLAG

<400> SEQUENCE: 36

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Cys Ile Gly Ala Gln Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205
```

Asn Phe Leu Asp Pro Asn Lys Ala Ser Ser Leu Leu Ser Ser Gly Phe
        210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
        260                 265                 270

Lys Trp Thr Asp Arg Ser Ser Glu Arg Tyr Lys Ile Asp Trp Cys Lys
        275                 280                 285

Glu Glu Met Thr Asn Asp Asp Asp Ser Gly Ser Gly Asp Tyr
290                 295                 300

Lys Asp Asp Asp Lys Ala His His His His His His
305                 310                 315

<210> SEQ ID NO 37
<211> LENGTH: 885
<212> TYPE: DNA
<213> ORGANISM: Artificial sequence
<220> FEATURE:
<223> OTHER INFORMATION: polynucleotide sequence of one subunit of
      alpha-hemolysin-E111N/K147N

<400> SEQUENCE: 37

```
atggcagatt ctgatattaa tattaaaacc ggtactacag atattggaag caatactaca    60
gtaaaaacag gtgatttagt cacttatgat aaagaaaatg gcatgcacaa aaaagtattt   120
tatagtttta tcgatgataa aaatcacaat aaaaaactgc tagttattag aacaaaaggt   180
accattgctg gtcaatatag agtttatagc gaagaaggtg ctaacaaaag tggtttagcc   240
tggccttcag cctttaaggt acagttgcaa ctacctgata tgaagtagc tcaaatatct   300
gattactatc caagaaattc gattgataca aaaaactata tgagtacttt aacttatgga   360
ttcaacggta atgttactgg tgatgataca ggaaaaattg gcggccttat tggtgcaaat   420
gtttcgattg tcatacact gaactatgtt caacctgatt tcaaaacaat tttagagagc   480
ccaactgata aaaagtagg ctggaaagtg atatttaaca atatggtgaa tcaaaattgg   540
ggaccatacg atcgagattc ttggaacccg gtatatggca atcaactttt catgaaaact   600
agaaatggtt ctatgaaagc agcagataac ttccttgatc ctaacaaagc aagttctcta   660
ttatcttcag ggttttcacc agacttcgct acagttatta ctatggatag aaaagcatcc   720
aaacaacaaa caaatataga tgtaatatac gaacgagttc gtgatgatta ccaattgcat   780
tggacttcaa caaattggaa aggtaccaat actaaagata atggacaga tcgttcttca   840
gaaagatata aaatcgattg ggaaaaagaa gaaatgacaa attaa                   885
```

<210> SEQ ID NO 38
<211> LENGTH: 293
<212> TYPE: PRT
<213> ORGANISM: artificial sequence
<220> FEATURE:
<223> OTHER INFORMATION: amino acid sequence of one subunit of alpha-
      hemolysin-E111N/K147N

<400> SEQUENCE: 38

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

```
Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
 50                  55                  60

Tyr Arg Val Tyr Ser Glu Glu Gly Ala Asn Lys Ser Gly Leu Ala Trp
 65                  70                  75                  80

Pro Ser Ala Phe Lys Val Gln Leu Gln Leu Pro Asp Asn Glu Val Ala
                 85                  90                  95

Gln Ile Ser Asp Tyr Tyr Pro Arg Asn Ser Ile Asp Thr Lys Asn Tyr
                100                 105                 110

Met Ser Thr Leu Thr Tyr Gly Phe Asn Gly Asn Val Thr Gly Asp Asp
            115                 120                 125

Thr Gly Lys Ile Gly Gly Leu Ile Gly Ala Asn Val Ser Ile Gly His
            130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
            210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
            275                 280                 285

Glu Glu Met Thr Asn
    290

<210> SEQ ID NO 39
<211> LENGTH: 518
<212> TYPE: DNA
<213> ORGANISM: Artificial Sequence
<220> FEATURE:
<223> OTHER INFORMATION: Synthesised sequence used in the examples

<400> SEQUENCE: 39
tttttttttt tttttttttt tttttttttt tttttttttt tttttttttt ggttgtttct      60
gttggtgctg atattgcgct ccactaaagg gccgattgac ccggtggtac cttggttgtt     120
tctgttggtg ctgatattgc ttttgatgcc gaccctaaat tttttgcctg tttggttcgc     180
tttgagtctt cttcggttcc gactaccctc ccgactgcct atgatgttta tcctttggat     240
ggtcgccatg atggtggtta ttataccgtc aaggactgtg tgactattga cgtccttccc     300
cgtacgccgg gcaataatgt ttatgttggt ttcatggttt ggtctaactt taccgctact     360
aaatgccgcg gattggtttc gctgaatcag gttattaaag agattatttg tctccagcca     420
cttaagtgag gtgatttatg tttggtgcta ttgctggcgg tattgcttct gctcttgctg     480
gtggcgccat gtctaaattg tttggaggcg gtcgagct                             518
```

```
<210> SEQ ID NO 40
<211> LENGTH: 530
<212> TYPE: DNA
<213> ORGANISM: Artificial Sequence
<220> FEATURE:
<223> OTHER INFORMATION: Synthesised sequence used in the example

<400> SEQUENCE: 40
tttttttttt tttttttttt tttttttttt tttttttttt tttttttttt ggttgtttct      60
gttggtgctg atattgcgct ccactaaagg gccgattgac gctccactaa agggccgatt     120
gacccggttg tttctgttgg tgctgatatt gcttttgatg ccgaccctaa attttttgcc     180
tgtttggttc gctttgagtc ttcttcggtt ccgactaccc tcccgactgc ctatgatgtt     240
tatcctttgg atggtcgcca tgatggtggt tattataccg tcaaggactg tgtgactatt     300
gacgtccttc cccgtacgcc gggcaataat gtttatgttg gtttcatggt ttggtctaac     360
tttaccgcta ctaaatgccg cggattggtt tcgctgaatc aggttattaa agagattatt     420
tgtctccagc cacttaagtg aggtgattta tgtttggtgc tattgctggc ggtattgctt     480
ctgctcttgc tggtggcgcc atgtctaaat tgtttggagg cggtcgagct                530

<210> SEQ ID NO 41
<211> LENGTH: 57
<212> TYPE: DNA
<213> ORGANISM: Artificial Sequence
<220> FEATURE:
<223> OTHER INFORMATION: Synthesised sequence used in the examples

<400> SEQUENCE: 41
agcgactaac aaacacaatc tgatggcttt tttttttttt tttttttttt tttttt         57
```